(12) United States Patent
Rands et al.

(10) Patent No.: US 11,773,062 B2
(45) Date of Patent: Oct. 3, 2023

(54) DEUTERATED COMPOUNDS

(71) Applicant: Small Pharma Ltd., London (GB)

(72) Inventors: Peter Rands, London (GB); Ellen James, London (GB); Tiffanie Benway, London (GB)

(73) Assignee: Small Pharma Ltd, London (GB)

( * ) Notice: Subject to any disclaimer, the term of this patent is extended or adjusted under 35 U.S.C. 154(b) by 20 days.

(21) Appl. No.: 17/208,583

(22) Filed: Mar. 22, 2021

(65) Prior Publication Data

US 2022/0081396 A1   Mar. 17, 2022

(51) Int. Cl.
C07D 209/14   (2006.01)

(52) U.S. Cl.
CPC ........ C07D 209/14 (2013.01); *C07B 2200/05* (2013.01)

(58) Field of Classification Search
CPC .................................................. C07D 209/14
See application file for complete search history.

(56) References Cited

U.S. PATENT DOCUMENTS

| | | | |
|---|---|---|---|
| 4,336,378 A | 6/1982 | Brand et al. | |
| 8,268,856 B2 | 9/2012 | Hamann et al. | |
| 11,000,534 B1 | 5/2021 | Sippy et al. | |
| 11,242,318 B2 | 2/2022 | Nivorozhkin et al. | |
| 2002/0022667 A1 | 2/2002 | Pace et al. | |
| 2009/0076121 A1 | 3/2009 | Czarnik et al. | |
| 2018/0221396 A1 | 8/2018 | Chadeayne | |
| 2020/0339519 A1 | 10/2020 | Kim et al. | |
| 2020/0390746 A1 | 12/2020 | Rands et al. | |
| 2021/0363104 A1* | 11/2021 | Nivorozhkin | C07D 209/16 |
| 2021/0378969 A1 | 12/2021 | Rands et al. | |
| 2021/0395201 A1 | 12/2021 | Rands et al. | |
| 2021/0403426 A1 | 12/2021 | Rands et al. | |
| 2022/0024956 A1* | 1/2022 | Slassi | A61K 31/404 |
| 2022/0062237 A1 | 3/2022 | Layzell et al. | |
| 2022/0062238 A1 | 3/2022 | Layzell et al. | |

FOREIGN PATENT DOCUMENTS

| | | | |
|---|---|---|---|
| GB | 2585978 A | 1/2021 | |
| GB | 2586940 A | 3/2021 | |
| GB | 2596884 A | 1/2022 | |
| WO | 9300333 A1 | 1/1993 | |
| WO | WO 02-083144 A1 | 10/2002 | |
| WO | 2004085392 A1 | 10/2004 | |
| WO | WO 2008-049116 A2 | 4/2008 | |
| WO | 2008071455 A1 | 6/2008 | |
| WO | 2008151584 A1 | 12/2008 | |
| WO | 2009049030 A1 | 4/2009 | |
| WO | 2018064465 A1 | 4/2018 | |
| WO | 2018195455 A1 | 10/2018 | |
| WO | WO 2019-081764 A1 | 5/2019 | |
| WO | 2020169850 A1 | 8/2020 | |
| WO | 2020169851 A1 | 8/2020 | |
| WO | 2020-176597 A1 | 9/2020 | |
| WO | 2020-176599 A1 | 9/2020 | |
| WO | WO 2020-245133 A1 | 12/2020 | |
| WO | WO 2021-089872 A1 | 5/2021 | |
| WO | WO 2021-089873 A1 | 5/2021 | |
| WO | 2021116503 A2 | 6/2021 | |
| WO | 2021155470 A1 | 8/2021 | |
| WO | 2021234608 A1 | 11/2021 | |
| WO | 2022031566 A1 | 2/2022 | |
| WO | 2022043227 A1 | 3/2022 | |
| WO | 2022069690 A2 | 4/2022 | |

OTHER PUBLICATIONS

Reiff, et al. Am. J. Psychiatry 2020:177:391-410.*
No new references.*
Chemieliva Pharmaceutical Product List, Order No. Cat. CC0034145.
Chemieliva Pharmaceutical Product List, Order No. Cat. CC0034141.
Brito-Da-Costa et al. "Toxicokinetics and Toxicodynamics of Ayahuasca Alkaloids N,N-Dimethyltryptamine (DMT), Harmine, Harmaline and Tetrahydroharmine: Clinical and Forensic Impact", Pharmaceuticals, vol. 13, No. 334, 36 pages. Oct. 23, 2020.
Barker et al., "Comparison of the brain levels of N N-Dimethyltryptamine and xxB B-Tetradeutero N, N-Dimethyltryptamine Following Intraperitoneal Injection", Biochemical Pharmacology, vol. 31, No. 15, Jan. 20, 1982, 5 pages.
Beaton et al., "A Comparison of the Behavioral Eeffects of Proteo- and Deurero-N, N-Dimethrltryptamine", Pharmacology, Biochemistry, vol. 16, No. 5, Sep. 8, 1981, 5 pages.

(Continued)

*Primary Examiner* — Shawquia Jackson
(74) *Attorney, Agent, or Firm* — Heslin Rothenberg & Farley & Mesiti, P.C.

(57) ABSTRACT

Described herein are compounds of formula (I) as defined herein, which comprise a greater proportion of deuterium to protium than naturally found in hydrogen; and compositions, including pharmaceutical compositions, comprising these compounds and optionally analogous compounds of formula (I), which are not deuterium-enriched. These compounds and compositions are of use in therapy, in particular in the treatment of psychiatric or neurological disorders. Varying the amounts of the different compounds within the compositions of the invention allows tailoring of the compositions' therapeutic effects. A particularly efficient synthetic method which enables compounds of formula (I) and related compounds of formula (I') is also provided.

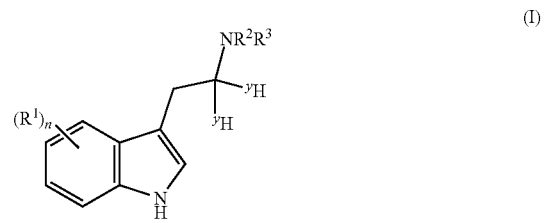

7 Claims, 2 Drawing Sheets

(56) References Cited

OTHER PUBLICATIONS

Brandt et al., "Microwave-accelerated synthesis of psychoactive deuterated N, N-dialkylated-tryptamines", Journal of Labelled Compounds and Radiopharmaceuticals, vol. 51, No. 14, 2008, 7 pages.
Morris Philip E Jr et a.l, "Indolealkylamine Metabolism: Synthesis of Deuterated Indolealkylamines as Metabolic Probes", Journal of Labelled Compounds and Radiopharmaceuticals, John Wiley & Sons Ltd, vol. 33, No. 6, Jan. 11, 1993, 12 pages.
Rands et al., Unpublished U.S. Appl. No. 17/616,345, filed Dec. 3, 2021.
Rands et al., Unpublished U.S. Appl. No. 17/469,063, filed Sep. 8, 2021.
Rands et al., Unpublished U.S. Appl. No. 17/574,424, filed Jan. 12, 2022.
Rands et al., Unpublished U.S. Appl. No. 17/680,411, filed Feb. 25, 2022.
Ambinter Screening Library, Publication Date Mar. 26, 2020, Order No. Cat. Amb33838664.
Aurora Building Blocks 2, Publication Date Feb. 27, 2020, Order No. Cat A17.921.638.
MuseChem Product List, Publication Date Apr. 21, 2020, Order No. Cat. R055190.
Barker, Steven A., "N, N-Dimethyltryptamine (DMT), an Endogenous Hallucinogen: Past, Present, and Future Research to Determine Its Role and Function", Frontiers in Neuroscience, vol. 12, Article 536, Aug. 6, 2018, pp. 1-17.
Cameron, et al., "Effects of N,N-Dimethyltryptamine on Rat Behaviors Relevant to Anxiety and Depression", Cameron, et el., "Effects of N,N-Dimethyltryptamine on Rat Behaviors Relevant to Anxiety and Depression", ACS Chemical Neuroscience, 2018, 18 pages. 2018.
Celik, et al., "Binding of Serotonin to the Human Serotonin Transporter. Molecular Modeling and Experimental Validation", Journal of the American Chemical Society, Mar. 2008, 13 pages.
Celik, et al., "Supplementary Information to Binding of Serotonin to the Human Serotonin Transporter. Molecular Modeling and Experimental Validation", Journal of the American Chemical Society, Mar. 2008, 14 pages.
Dunlap, et al., "Identification of Psychoplastogentic N,N-Dimethylaminoisotryptamine (isoDMT) Analogues through Structure—Activity Relationship Studies", Journal of Medicinal Chemistry, 2020, 14 pages.
Dyck, et al., "Effect of Deuterium Substitution on the Disposition of Intraperitoneal Tryptamine", Biochemical Pharmacology, vol. 35, No. 17, 1986, pp. 2893-2896.
Gaujac, et al., "Investigations into the polymorphic properties of N,N-dimethyltryptamine by X-ray diffraction and differential scanning calorimetr", Microchemical Journal, 2013, 26 pages.
Ghosal, et al., "Indole Bases of Desmodium Gyrans", Phytochemistry (Elsevier), vol. 11, No. 5, 1972, 2 pages.
Grina, et al., "Old and New Alkaloids From Zanthoxylum Arborescens", Journal of Organic Chemistry, vol. 47, No. 13, 1982, pp. 2648-2651.
Halberstadt, et al., "Behavorial effects of x,x,B,B-tetradeutero-5-MeO-DMT in rats: comparison with 5-MeO-DMT administered in combination with a monoamine oxidase inhibitor", Psychopharmacology, Jan. 6, 2012.
Ibrahim, et al., "Marine inspired 2-(5-Halo-1H-indol-3-yl)-N,N-dimethylethanamines as Modulators of Serotonin Receptors: An Example Illustrating the Power of Bromine as Part of the Uniquely Marine Chemical Space", Marine drugs, 2017, 14 pages.
Mcilhenny, et al., "Direct Analysis of Psychoactive Tryptamine and Harmala Alkaloids in the Amazonian Botanical Medicine Ayahuasca by Liquid", Journal of Chromatography A, vol. 1216, No. 51, 2009, 9 pages.
Queiroz, et al., "Chemical Composition of the Ark of Tetrapterys Mucronate and Identification of Acetrylcholinesterase Inhibitory Constituents", Journal of Natural Products, vol. 77, No. 3, 2014, 7 pages.
Riga, et al., "Theserotonin hallucinogen 5-MeO-DMT alters corticothalamic activity in freely moving mice: Regionally-selective involvement of 5-HT1A and 5-HT2A receptors", Neuropharmacology, 2017, 12 pages, 2017.
Sard, et al., "SAR of psilocybin analogs: Discovery of a selective 5-HT2c agonist", Sard, et al., "SAR of psilocybin analogs: Discovery of a selective 5-HT2c agonist", Bioorganic & Medicinal Chemistry Letters 15, Aug. 2005, 5 pages.
Servillo, et al., "Citrus Genus Plants Contain N-Methylated Tryptamine Derivatives and Their 5-Hydroxylated Forms", Journal of Agricultural and Food Chemistry, vol. 61, No. 21, 2013, pp. 5156-5162.
Strassman, , "Dose-Response Study of N, N-Dimethyltryptamine in Humans: II. Subjective Effects and Preliminary Results of a New Rating Scale", Strassman, et al., "Dose-Response Study of N, N-Dimethyltryptamine in Humans: II. Subjective Effects and Preliminary Results of a New Rating Scale", Archives of General Psychiatry, Chicago, IL, Feb. 1994, 18 pages, 1994.
Tearavarich, et al., "Microwave-Accelerated Preparation and Analytical Characterization of 5-ethoxy-N,N-dialkyl-[$\alpha,\alpha,\beta,\beta$-H(4) ]- and [$\alpha,\alpha,\beta,\beta$-D(4) ]-tryptamines", Drug Testing and Analysis, vol. 3, No. 9, Dec. 2010, pp. 597-608.
Timmins, Graham S. , "Expert Opin ther Pat.", HHS Public Access, Oct. 2014, 19 Pages.
Walker, et al., "Gas Chromatographic-Mass Spectrometric Isotope Dilution Assay for N,N-Dimethyltryptamine in Human Plasma", Biochemical Medicine, vol. 8, Aug. 1972, pp. 105-113.
Blair et al., "Effect of Ring Fluorination on the Pharmacology of Hallucinogenic Tryptamines", J. Med. Chem., vol. 43, pp. 4701-4710. 2000.
Dunlap et al., "Reaction of N,N-Dimethyltryptamine with Dichloromethane Under Common Experimental Conditions", ACS Omega, vol. 3, pp. 4968-4973. 2018.
Tombari et al., "Ex Vivo Analysis of Tryptophan Metabolism Using 19F NMR", ACS Chem. Biol., vol. 14, pp. 1866-1873. 2019.
Yingxiang, "Drug Synthesis Reactions", (New World Era, 2nd edition), Beijing: China Press of Traditional Chinese Medicine, Aug. 2017, p. 134.
Roseman et al., "Quality of Acute Psychedelic Experience Predicts Therapeutic Efficacy of Psilocybin for Treatment-Resistant Depression", Frontiers in Pharmacology, vol. 8, Article 974, 10 pages. Jan. 2018.
ATZRODT et al. Deuterium- and Tritium-Labelled Compounds: Application in the Life Sciences, Angew. Chem. Int. Ed., vol. 57, pp. 1758-1784, 2018.

\* cited by examiner

DEUTERATED COMPOUNDS

BACKGROUND

Classical psychedelics have shown preclinical and clinical promise in treating psychiatric disorders (Carhart-Harris and Goodwin, *Neuropsychopharmacology* 42, 2105-2113 (2017)). In particular, psilocybin has demonstrated significant improvement in a range of depression and anxiety rating scales in randomised double blind studies (Griffiths et al. *Journal of Psychopharmacology*, 30(12), 1181-1197 (2016)). Efficacy of psilocybin has been shown in depression (R. L. Carhart-Harris et al., *Psychopharmacology*, 2018, 235, 399-408), end of life anxiety (R. R. Griffiths et al., *J. Psychopharmacol.*, 2016, 30, 12, 1181-1197) and addiction (M. W. Johnson, A. Garcia-Romeu and R. R. Griffiths, *Am. J. Drug Alcohol Abuse*, 2017, 43, 1, 55-60), and is currently being investigated for several other mental health disorders that are rooted in psychologically destructive patterns of thought processing (Anorexia Nervosa: NCT #NCT04052568).

5-methoxy-N,N-dimethyltryptamine (5-MeO-DMT) is an endogenous tryptamine found in human blood, urine, and spinal fluid (S. A. Barker, E. H. McIlhenny and R. Strassman, *Drug Test. Anal.*, 2012, 4, 7-8, 617-635; F. Benington, R. D. Morin and L. C. Clark, *J. Med. Sci.*, 1965, 2, 397-403; F. Franzen, and H. Gross, *Nature*, 206, 1052; R. B. Guchhait, *J. Neurochem.*, 1976, 26, 1, 187-190), and has been shown to exhibit protective and therapeutically relevant effects. Antidepressant properties have been shown in rodents administered 5-MeO-DMT (M. S. Riga et al., *Neuropharmacology*, 2017, 113, A, 148-155). In addition, a high number of users of 5-MeO-DMT, having administered it in different forms, reported therapeutic effects attributed to its use, including improved post-traumatic stress disorder, depression and anxiety (A. K. Davis et al., *J. Psychopharmacol.*, 2018, 32, 7, 779-792). 5-MeO-DMT has also exhibited the potential to treat substance abuse disorders (V. Dakic et al., *Sci. Rep.*, 2017, 7, 12863).

N,N-dimethyltryptamine (DMT) is also understood to hold therapeutic value as a short-acting psychedelic. A review of research into the biosynthesis and metabolism of DMT in the brain and peripheral tissues, methods and results for DMT detection in body fluids and the brain, new sites of action for DMT, and new data regarding the possible physiological and therapeutic roles of DMT is provided by S. A. Barker in *Front. Neurosci.*, 12, 536, 1-17 (2018). In this review, DMT is described as having a possible therapeutic role in the treatment of depression, obsessive-compulsive disorder, and substance abuse disorders.

N-Methyltryptamine (NMT) is often extracted together with DMT and 5-MeO-DMT from the bark, shoots and leaves of several plant genera. NMT is reported to have psychedelic properties: smoking NMT gives "visuals" at 50-100 mg, with a duration of 15-30 seconds (Shulgin, A. and Shulgin, A., 2002, *THIKAL: the continuation*, Transform Press).

The duration of action of DMT (under 20 minutes) is so short as to limit effective therapy. Whilst administration protocols have been developed to extend the immersive psychedelic experience of DMT (Gallimore and Strassman (2016), *A model for the application of target-controlled intravenous infusion for a prolonged immersive DMT psychedelic experience*, Frontiers in Pharmacology, 7:211), these protocols may carry risk of toxic build-up in patients who are poor metabolisers of DMT (for further discussion see Strassman et al (1994), *Dose response study of N,N-dimethyltryptamine in humans*, Arch Gen Psychiatry 51, 85).

DMT and its substituted analogues, such as 5-MeO-DMT, are understood to be primarily inactivated through a deamination pathway mediated by monoamine oxidases (MAOs). MAO-mediated metabolism of DMT affords indole-3-acetic acid (IAA) via oxidative deamination (O. Suzuki et al. *Inhibition of type A and type B monoamine oxidases by naturally occurring xanthones*, Planta Med., 42: 17-21 (1981) and J. Riba, et al., *Metabolism and urinary disposition of N,N-dimethyltryptamine after oral and smoked administration: a comparative study*, Drug Test. Anal., 7(5): 401-406 (2015)).

DMT-N-oxide (DMT-NO) is the second most abundant metabolite of DMT formed via N-oxidation. Further minor metabolites have also been identified including N-methyltryptamine (NMT), 2-methyl-1,2,3,4-tetrahydro-beta-carboline (MTHBC) and THBC (see Barker (2018), supra, for a review). The production of alternative metabolites such as DMT-NO and NMT are believed to be independent of MAO activity (S. A. Barker et al., *In vivo metabolism of α,α,β,β-tetradeutero-N,N-dimethyltryptamine in rodent brain*, Biochem. Pharmacol, 33(9): 1395-400 (1984)). It appears unclear as to the responsible enzyme involved in for the formation of the N-oxide and other metabolites.

In the light of the prominent role understood to be played by MAOs in the metabolic inactivation by DMT and its substituted analogues, such as 5-MeO-DMT, DMT and substituted analogues such as 5-MeO-DMT are often administered with MAO inhibitors (MAOIs) to prevent inactivation of the compounds before they have reached their target site in the body, allowing for a prolonged and increased exposure to the compound. However, since MAOIs can cause high blood pressure when taken with certain foods or medications, the use of MAOIs by a patient typically requires the patient to restrict their diet and avoiding some other medications.

Naturally occurring hydrogen contains about 0.02 molar percent deuterium and 99.98% protium. Physical chemical properties between protium and deuterium are small but measurable. Deuterium is slightly less lipophilic than protium, has a smaller molar volume and carbon-deuterium bonds are shorter than carbon-protium bonds. Deuterium keeps the 3D surface, shape and steric flexibility unaltered compared to H.

These properties indicate that the incorporation of deuterium into DMT is expected to progressively reduce lipophilicity and increase basicity in a non-additive manner, dependent upon stereochemical position, whilst also retaining the biochemical potency and selectivity of the parent compound. Moreover, the enrichment of DMT's hydrogen atoms with deuterium is expected to cause a shift in the compound stability, measured as the deuterium kinetic isotope effect (DKIE).

The difference in stability of isotopically substituted molecules is referred to as the primary kinetic isotopic effect (KIE), which for deuterium can be defined as the deuterium kinetic isotope effect (DKIE). DKIE is quantified as the ratio of the rate constants for the reaction (kH/kD) and typically ranges from 1 (where deuterium has no effect on reaction) to 7, with the theoretical limit being 9.

As enzyme-catalysed transformations are multistep, in order to observe high DKIE, it is necessary that the C—H cleavage step is at least partially rate-limiting. Other kinetic models such as quantum-mechanical tunnelling is invoked to explain a secondary DKIE. While this is usually much smaller in magnitude than the primary effect (typically 1.1-1.2), this mechanism can nonetheless lead to significantly larger effects.

Deuterium substitution of hydrogen atoms at the α and β-positions of the ethylamine side chain of DMT (α,α,β,β-tetradeuterio-DMT, D$_4$DMT) was demonstrated by Barker et al. to have a KIE in vivo (S. A. Barker et al., 1982, *Comparison of the brain levels of N,N-dimethyltryptamine and α,α,β,β-tetradeutero-N,N-dimethyltryptamine following intraperitoneal injection, Biochemical Pharmacology,* 31(15), 2513-2516 (1982)). D$_4$DMT was found to have a shorter time to onset and potentiation of behaviour disrupting effects when compared to equal doses of DMT. However, no kinetic data was reported to quantify the DKIE (S. A. Barker et al., supra, (1982); S. A. Barker et al., supra (1984); and J. M. Beaton et al., *A Comparison of the Behavioral Effects of Proteo- and Deutero-N,N-Dimethyltryptamine. Pharmacol. Biochem. Behav,* 1982. 16(5): 811-4 (1982)).

The synthesis of α,α,-bis-deuterium-DMT (D$_2$DMT) has been reported in the literature (P. E. Morris and C. Chiao (*Journal of Labelled Compounds And Radiopharmaceuticals*, Vol. XXXIII, No. 6, 455-465 (1993)). However, no biological or metabolism data has been published.

In WO 2020/245133 A1 (Small Pharma Ltd), knowledge of the kinetic isotope effect exhibited by α,α,β,β-tetradeutero-N,N-dimethyltryptamine is used in order to modify, controllably, the pharmacokinetic profile of N,N-dimethyltryptamine, thereby permitting more flexible therapeutic application.

The use of N,N-(dimethyl-d$_6$)-tryptamine (d$_6$-DMT) as an internal standard in the bioanalysis of plasma samples of DMT is described by G. N. Rossi et al., *J. Pschedelic Stud.,* 3(1), 1-6 (2019); G. de Oliveira Silveria et al., *Molecules*, 25, 2072, 1-11 (2020); and C. D. R. Oliveira et al., *Bioanalysis,* 2012, 4(14), 1731-1738). However, there is no mention of the possibility of using d$_6$-DMT itself as a therapeutically active substance.

In light of the therapeutic potential of DMT and substituted analogues, there remains a need in the art for alternative compounds, for example compounds with improved bioavailability, extended and/or modified pharmacokinetics and/or modified pharmacodynamics, for use in psychotherapy, in particular for the development of clinically applicable psychedelic drug substances to assist psychotherapy. The present invention addresses this need.

SUMMARY

DMT is metabolised very quickly in the human body. Using modelled data from Timmerman (C. Timmermann et al., *DMT Models the Near-Death Experience, Front. Psychol* 9: 1424 (2018) and C. Timmermann et al., *Neural correlates of the DMT experience assessed with multivariate EEG*, Sci. Rep. 9: 16324 (2019)), we have calculated that DMT has have a half-life of approximately 5 minutes and clearance rate of 24483 ml/min, which equates to 350 ml/min/kg based on a 70 kg person. This clearance rate is much greater than average human liver blood flow, which is 20 ml/min/kg with a cardiac output of 71 ml/min/kg. Based on these calculations, we reasoned that DMT is largely metabolised before reaching the human liver.

In research described herein, we have demonstrated that intrinsic clearance and half-life values of deuterated DMT compounds in human liver mitochondrial fractions, which contain high quantities of MAOs, are different to the values in hepatocytes such as human liver microsomes and whole cell hepatocytes. Moreover, these pharmacodynamic parameters vary additionally depending on whether there is deuterium substitution at the carbon atom adjacent to the dimethylamino moiety of DMT (α-deuteration) or on the carbon atoms of the methyl groups (methyl group deuteration).

Specifically, we found that α-deuteration gives rise to an increase in metabolic stability (in comparison with the parent compound: undeuterated DMT) in human hepatocytes whereas methyl group deuteration has a minimal effect on metabolic stability in such a system. On the other hand, significantly greater increases in metabolic stability in mitochondrial fractions were found with a representative deuterated DMT having complete methyl group deuteration in comparison with a corresponding compound with no methyl group deuteration.

The liver contains both phase I and phase II drug metabolising enzymes, which are present in the intact cell, making hepatocytes a valuable in vitro model for the study of drug metabolism, in order to predict in vivo clearance. However, hepatic fractions such as human liver microsomes and whole cell hepatocytes contain significant quantities of cytochrome P450 enzymes, the predominant location of cytochrome P450 enzymes in the body being in the liver. Human liver mitochondrial fractions, although being liver-derived, contain less cytochrome P450 enzymes than whole cell hepatocytes but, as already noted, significant quantities of MAOs. Whilst whole cell hepatocytes also contain significant quantities of MAOs, MAO is more homogeneously distributed throughout the body (more homogeneously than cytochrome P450 enzymes that is), being found in most cell types.

The enhancement in metabolic stability in human liver mitochondrial fractions conferred by methyl group deuteration is suggestive of a greater stability towards metabolism by mitochondrial enzymes, and thus of greater metabolic stability in vivo, in comparison with undeuterated or alpha-only deuterated DMT.

Accordingly, and viewed from a first aspect, the invention provides a compound of formula (I):

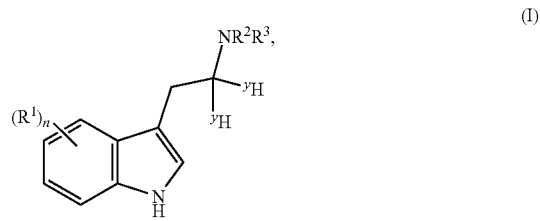

wherein:
R$^1$ is independently selected from —R$^4$, —OH, —OR$^4$, —O(CO)R$^4$, monohydrogen phosphate, —F, —Cl, —Br and —I;
n is selected from 0, 1, 2, 3 or 4;
R$^2$ is C($^x$H)$_3$;
R$^3$ is C($^x$H)$_3$ or H;
each R$^4$ is independently selected from C$_1$-C$_4$alkyl; and
each $^x$H and $^y$H is independently protium or deuterium, wherein a ratio of deuterium:protium in a C($^x$H)$_3$ moiety in the compound is greater than that found naturally in hydrogen,
or a pharmaceutically acceptable salt thereof,
for use in therapy.

It is understood that the only DMT compound with methyl group deuteration described hitherto is N,N-di(trideuteromethyl)tryptamine (i.e. $d_6$-DMT) with no suggestion in the art of the utility of methyl group deuteration in providing therapeutically active DMTs. Accordingly, viewed from a second aspect, the invention provides a compound or pharmaceutically acceptable salt is defined in accordance with the first aspect of the invention, which is not N,N-di(trideuteromethyl)tryptamine, but which may, for example, be a pharmaceutically acceptable salt of N,N-di(trideuteromethyl)tryptamine.

Viewed from a third aspect, the invention provides a composition comprising a first compound, which is a compound or pharmaceutically acceptable salt thereof as defined in accordance with the first aspect of the invention, and a second compound, which is either (i) a compound or pharmaceutically acceptable salt thereof as defined in accordance with the first aspect of the invention, but which differs from the first compound through the identity of $^yH$ and/or the identity of $R^3$; or (ii) a compound or pharmaceutically acceptable salt thereof as defined in accordance with the first aspect of the invention, except that each $^xH$ and $^yH$ represent hydrogen.

Viewed from a fourth aspect, the invention provides a pharmaceutical composition comprising a compound defined in accordance with the first or second aspects of the invention or composition in accordance with the third aspect of the invention, in combination with a pharmaceutically acceptable excipient.

Viewed from a fifth aspect, the invention provides a compound defined in accordance with the first or second aspects of the invention or composition in accordance with the third or fourth aspects of the invention for use in a method of treating a psychiatric or neurological disorder in a patient.

Viewed from a sixth aspect, the invention provides a method of treatment comprising administering to a patient in need thereof a compound defined in accordance with the first or second aspects of the invention or composition in accordance with the third or fourth aspects of the invention.

Viewed from a seventh aspect, the invention provides a method comprising synthesising a compound of formula (I'):

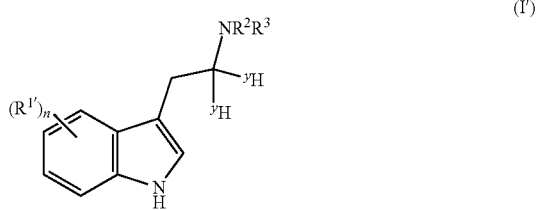

(I')

or a pharmaceutically acceptable salt thereof, comprising reacting a compound of formula (II):

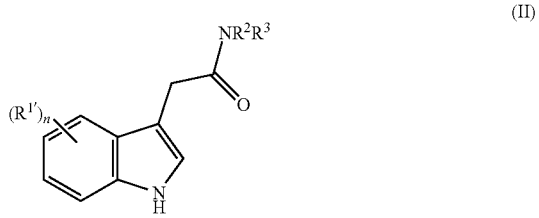

(II)

with LiAlH$_4$ and/or LiAlD$_4$, wherein:
$R^{1'}$ is independently selected from —$R^4$, —OPR, —OR$^4$, —F, —Cl, —Br and —I;
PR is a protecting group,
n is selected from 0, 1, 2, 3 or 4;
$R^2$ is C($^xH$)$_3$;
$R^3$ is C($^xH$)$_3$ or H;
each $R^4$ is independently selected from C$_1$-C$_4$alkyl; and
each $^xH$ and $^yH$ is independently protium or deuterium,
wherein a ratio of deuterium:protium in a C($^xH$)$_3$ moiety in the compound of formula (I') is greater than that found naturally in hydrogen,
or a pharmaceutically acceptable salt thereof.

Optionally, compounds of formula (I') in which $R^{1'}$ is —OPR are converted to compounds of formula (I) using chemistry at the disposal of the skilled person.

Further aspects and embodiments of the present invention will be evident from the discussion that follows below.

DETAILED DESCRIPTION

Figure 1:
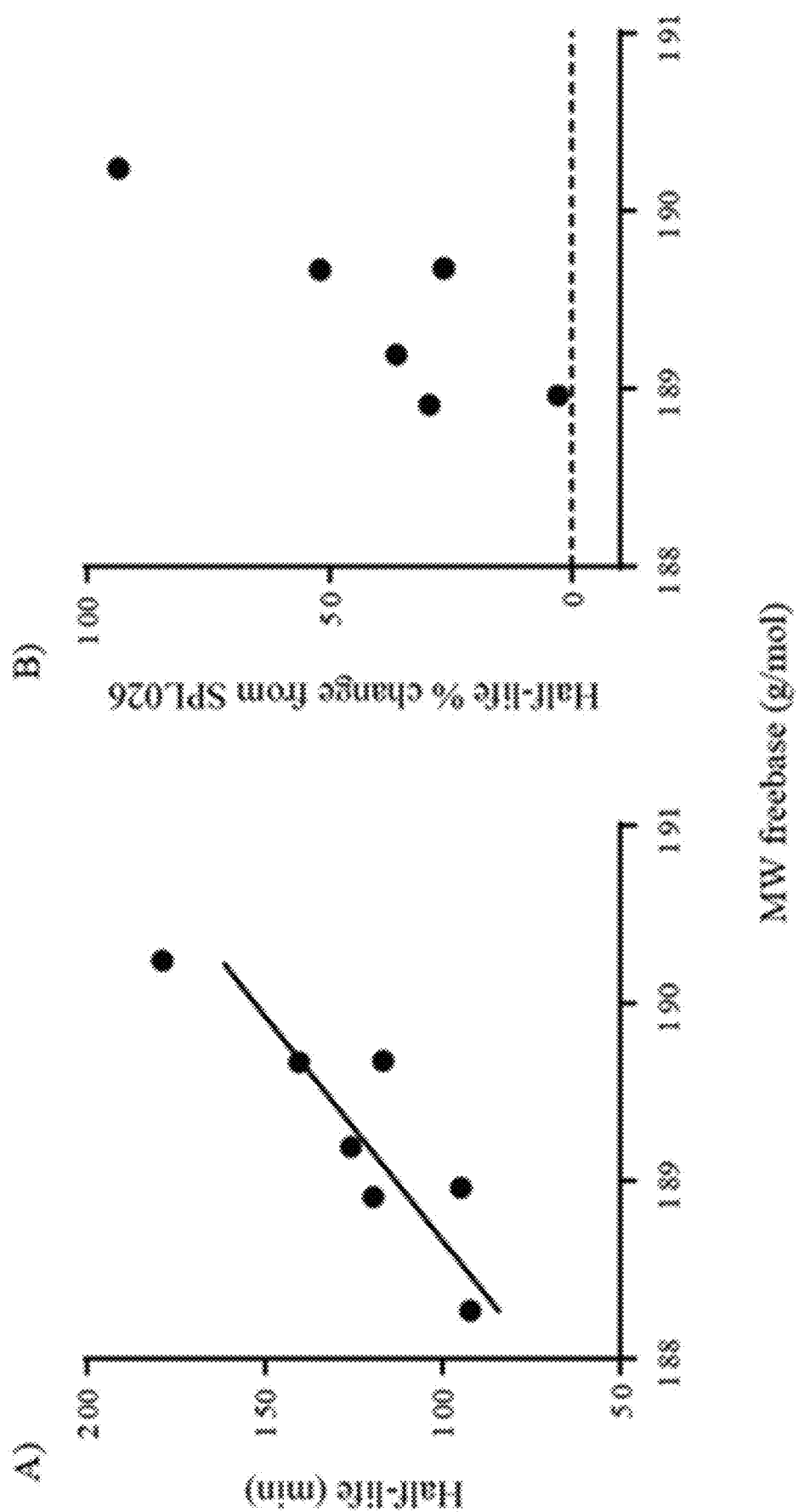
FIG. 1: calculated in vitro half-life for DMT and 6 deuterium-containing compositions, as described in the Examples section, below. A) Linear regression analysis. The $r^2$ value for half-life is 0.754; where the slope was found to be significantly different to zero, p=0.01. B) Half-life of deuterated analogues as a percent change from (undeuterated) DMT (dashed line).

Throughout this specification, one or more aspects of the invention may be combined with one or more features described in the specification to define distinct embodiments of the invention.

In the discussion that follows, reference is made to a number of terms, which are to be understood to have the meanings provided below, unless a context expressly indicates to the contrary. The nomenclature used herein for defining compounds, in particular the compounds described herein, is intended to be in accordance with the rules of the International Union of Pure and Applied Chemistry (IUPAC) for chemical compounds, specifically the "IUPAC Compendium of Chemical Terminology (Gold Book)" (see A. D. Jenkins et al., Pure & Appl. Chem., 1996, 68, 2287-2311). For the avoidance of doubt, if a rule of the IUPAC organisation is contrary to a definition provided herein, the definition herein is to prevail.

References herein to a singular of a noun encompass the plural of the noun, and vice-versa, unless the context implies otherwise. For example, "a compound of formula (I)" refers to one or more compounds of formula (I).

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps. The term "comprising" includes within its ambit the term "consisting".

The term "consisting" or variants thereof is to be understood to imply the inclusion of a stated element, integer or step, or group of elements, integers or steps, and the exclusion of any other element, integer or step or group of elements, integers or steps.

The term "about" herein, when qualifying a number or value, is used to refer to values that lie within ±5% of the value specified. For example, if a temperature range of about 15 to about 25° C. is referred to, temperatures of 14.25 to 26.25° C. are encompassed.

The term "hydrocarbyl" defines univalent groups derived from hydrocarbons by removal of a hydrogen atom from any carbon atom, wherein the term "hydrocarbon" refers to compounds consisting of hydrogen and carbon only. Where a hydrocarbyl is disclosed as optionally comprising one or more heteroatoms, any carbon or hydrogen atom on the hydrocarbyl may be substituted with a heteroatom or a functional group comprising a heteroatom, provided that valency is satisfied. One or more heteroatoms may be selected from the group consisting of nitrogen, sulfur and oxygen.

Oxygen and sulfur heteroatoms or functional groups comprising these heteroatoms may replace —H or —CH$_2$— of a hydrocarbyl, provided that, when —H is replaced, oxygen or the functional group comprising oxygen binds to the carbon originally bound to the —H as either =O (replacing two —H) or —OH (replacing one —H), and sulfur or the functional group comprising sulfur binds to the carbon atom originally bound to the —H as either =S (replacing two —H) or —SH (replacing one —H). When methylene (—CH$_2$—) is replaced, oxygen binds to the carbon atoms originally bound to —CH$_2$— as —O— and sulfur binds to the carbon atoms originally bound to —CH$_2$— as —S—.

Nitrogen heteroatoms or functional groups comprising nitrogen heteroatoms may replace —H, —CH$_2$—, or —CH=, provided that, when —H is replaced, nitrogen or the functional group comprising nitrogen binds to the carbon originally bound to the —H as ≡N (replacing three —H), =NH (replacing two —H) or —NH$_2$ (replacing one —H); when —CH$_2$— is replaced, nitrogen or the functional group comprising nitrogen binds to the carbon atoms originally bound to —CH$_2$— as —NH—; and when —CH= is replaced, nitrogen binds to the carbon atoms originally bound to —CH= as —N=.

The term "alkyl" is well known in the art and defines univalent groups derived from alkanes by removal of a hydrogen atom from any carbon atom, wherein the term "alkane" is intended to define acyclic branched or unbranched hydrocarbons having the general formula $C_nH_{2n+2}$, wherein n is an integer ≥1. $C_1$-$C_4$alkyl refers to any one selected from the group consisting of methyl, ethyl, n-propyl, iso-propyl, n-butyl, sec-butyl, iso-butyl and tert-butyl.

The term "cycloalkyl" defines all univalent groups derived from cycloalkanes by removal of a hydrogen atom from a ring carbon atom. The term "cycloalkane" defines saturated monocyclic and polycyclic branched or unbranched hydrocarbons, where monocyclic cycloalkanes have the general formula $C_nH_{2n}$, wherein n is an integer ≥3. Typically, the cycloalkyl is a $C_5$-$C_6$cycloalkyl, such as cyclopentyl or cyclohexyl.

The term "alkylamino" refers to alkyl groups in which any one hydrogen atom is substituted with a primary (—NH$_2$), secondary (—NRH) or tertiary (—NR$_2$) amino groups, where R is, or each R is independently, a hydrocarbyl group. Typically, any one hydrogen atom is substituted with a tertiary amino group wherein each R is independently a $C_1$-$C_4$alkyl.

The term "acetoxy" (often abbreviated to OAc) defines a univalent group derived from acetic acid by removal of a hydrogen atom from the OH moiety. The term "methoxy" (often abbreviated to OMe) defines a univalent group derived from methanol by removal of a hydrogen atom from the OH moiety. The term monhydrogen phosphate defines a divalent group of formula HPO$_4$, derived from phosphoric acid by removal of a proton from two of the three OH moieties, and thus denotes a substituent of formula —OP(O)(OH)O$^-$.

By hydrogen is meant herein that, in a plurality of like compounds, the isotopes of such denoted hydrogen are present in their natural abundances unless a context explicitly dictates to the contrary. For example, where $^x$H and $^y$H in a particular compound are stated to represent hydrogen, the isotopes of hydrogen in $^x$H and $^y$H in a plurality of such compounds are present in their natural abundances.

Where a compound, for example of formula (I), is substituted with monohydrogen phosphate (i.e. where $R^1$ is monohydrogen phosphate), it is understood that "monohydrogen phosphate" also encompasses protonated or unprotonated analogues, i.e. dihydrogen phosphate and phosphate are also included. This is to reflect that psilocybin (also known as [3-(2-Dimethylaminoethyl)-1H-indol-4-yl] dihydrogen phosphate), and analogues such as [3-(2-methylaminoethyl)-1H-indol-4-yl] dihydrogen phosphate, in water generally comprise monohydrogen phosphate, this generally being understood to be the predominant form owing to the pKa values of the two terminal phosphate oxygen atoms being estimated as 1.3 and 6.5. It is further understood that the monohydrogen phosphate-containing form of psilocybin and analogues exists as a zwitterion (i.e. an internal salt) in which the nitrogen atom of the dimethylamino (or monomethylamino) moiety is protonated. For the avoidance of doubt, zwitterions are considered separately to salts, i.e. the pharmaceutically acceptable salts of the invention refer to salts comprising compounds of formula (I) of the invention and an acid. For example, a salt may be of psilocybin and fumaric acid.

The compounds of formula (I) described herein, for example within the compositions in accordance with the third and fourth aspects of the invention, are useful in therapy and may be administered to a patient in need thereof. As used herein, the term 'patient' preferably refers to a mammal. Typically, the mammal is a human, but may also refer to a domestic mammal. The term does not encompass laboratory mammals.

The terms "treatment" and "therapy" define the therapeutic treatment of a patient, in order to reduce or halt the rate of progression of a disorder, or to ameliorate or cure the disorder. Prophylaxis of a disorder as a result of treatment or therapy is also included. References to prophylaxis are intended herein not to require complete prevention of a disorder: its development may instead be hindered through treatment or therapy in accordance with the invention. Typically, treatment or therapy is not prophylactic, and the compounds or compositions are administered to a patient having a diagnosed or suspected disorder.

Psychedelic-assisted psychotherapy means the treatment of a mental disorder by psychological means, which are enhanced by one or more protocols in which a patient is subjected to a psychedelic experience. A psychedelic experience is characterized by the striking perception of aspects of one's mind previously unknown, and may include one or more changes of perception with respect to hallucinations, synesthesia, altered states of awareness or focused consciousness, variation in thought patterns, trance or hypnotic states, and mystical states.

As is understood in the art, psychocognitive, psychiatric or neurological disorders are disorders which may be associated with one or more cognitive impairment. As used herein, the term 'psychiatric disorder' is a clinically significant behavioural or psychological syndrome or pattern that occurs in an individual and that is associated with present distress (e.g., a painful symptom) or disability (i.e., impairment in one or more important areas of functioning) or with a significantly increased risk of suffering death, pain, disability, or an important loss of freedom.

Diagnostic criteria for psychiatric or neurological disorders referred to herein are provided in the Diagnostic and Statistical Manual of Mental Disorders, Fifth Edition, (DSM-5).

As used herein the term 'obsessive-compulsive disorder' (OCD) is defined by the presence of either obsessions or compulsions, but commonly both. The symptoms can cause significant functional impairment and/or distress. An obsession is defined as an unwanted intrusive thought, image or urge that repeatedly enters the person's mind. Compulsions are repetitive behaviours or mental acts that the person feels driven to perform. Typically, OCD manifests as one or more obsessions, which drive adoption of a compulsion. For example, an obsession with germs may drive a compulsion to clean or an obsession with food may drive a compulsion to overeat, eat too little or throw up after eating (i.e. an obsession with food may manifest itself as an eating disorder). A compulsion can either be overt and observable by others, such as checking that a door is locked, or a covert mental act that cannot be observed, such as repeating a certain phrase in one's mind.

The term "eating disorder" includes anorexia nervosa, bulimia and binge eating disorder (BED). The symptoms of anorexia nervosa include eating too little and/or exercising too much in order to keep weight as low as possible. The symptoms of bulimia include eating a lot of food in a very short amount of time (i.e. binging) and then being deliberately sick, using laxatives, eating too little and/or exercising too much to prevent weight gain. The symptoms of BED include regularly eating large portions of food until uncomfortably full, and consequently feeling upset or guilty.

As used herein the term 'depressive disorder' includes major depressive disorder, persistent depressive disorder, bipolar disorder, bipolar depression, and depression in terminally ill patients.

As used herein the term 'major depressive disorder' (MDD, also referred to as major depression or clinical depression) is defined as the presence of five or more of the following symptoms over a period of two-weeks or more (also referred to herein as a 'major depressive episode'), most of the day, nearly every day:
   depressed mood, such as feeling sad, empty or tearful (in children and teens, depressed mood can appear as constant irritability);
   significantly reduced interest or feeling no pleasure in all or most activities;
   significant weight loss when not dieting, weight gain, or decrease or increase in appetite (in children, failure to gain weight as expected);
   insomnia or increased desire to sleep;
   either restlessness or slowed behaviour that can be observed by others;
   fatigue or loss of energy;
   feelings of worthlessness, or excessive or inappropriate guilt;
   trouble making decisions, or trouble thinking or concentrating;
   recurrent thoughts of death or suicide, or a suicide attempt.
At least one of the symptoms must be either a depressed mood or a loss of interest or pleasure.

Persistent depressive disorder, also known as dysthymia, is defined as a patient exhibiting the following two features:
   A. has depressed mood for most the time almost every day for at least two years. Children and adolescents may have irritable mood, and the time frame is at least one year.
   B. While depressed, a person experiences at least two of the following symptoms:
      Either overeating or lack of appetite.
      Sleeping too much or having difficulty sleeping.
      Fatigue, lack of energy.
      Poor self-esteem.
      Difficulty with concentration or decision-making.

As used herein the term 'treatment resistant major depressive disorder' describes MDD that fails to achieve an adequate response to an adequate treatment with standard of care therapy.

As used herein, 'bipolar disorder', also known as manic-depressive illness, is a disorder that causes unusual shifts in mood, energy, activity levels, and the ability to carry out day-to-day tasks.

There are two defined sub-categories of bipolar disorder; all of them involve clear changes in mood, energy, and activity levels. These moods range from periods of extremely "up," elated, and energised behaviour (known as manic episodes, and defined further below) to very sad, "down," or hopeless periods (known as depressive episodes). Less severe manic periods are known as hypomanic episodes.

Bipolar I Disorder—defined by manic episodes that last at least 7 days, or by manic symptoms that are so severe that the person needs immediate hospital care. Usually, depressive episodes occur as well, typically lasting at least 2 weeks. Episodes of depression with mixed features (having depression and manic symptoms at the same time) are also possible.

Bipolar II Disorder—defined by a pattern of depressive episodes and hypomanic episodes, but not the full-blown manic episodes described above.

As used herein 'bipolar depression' is defined as an individual who is experiencing depressive symptoms with a previous or coexisting episode of manic symptoms, but does not fit the clinical criteria for bipolar disorder.

As used herein, the term 'anxiety disorder' includes generalised anxiety disorder, phobia, panic disorder, social anxiety disorder, and post-traumatic stress disorder.

'Generalised anxiety disorder' (GAD) as used herein means a chronic disorder characterised by long-lasting anxiety that is not focused on any one object or situation. Those suffering from GAD experience non-specific persistent fear and worry, and become overly concerned with everyday matters. GAD is characterised by chronic excessive worry accompanied by three or more of the following symptoms: restlessness, fatigue, concentration problems, irritability, muscle tension, and sleep disturbance.

'Phobia' is defined as a persistent fear of an object or situation the affected person will go to great lengths to avoid, typically disproportional to the actual danger posed. If the feared object or situation cannot be avoided entirely, the affected person will endure it with marked distress and significant interference in social or occupational activities.

A patient suffering from a 'panic disorder' is defined as one who experiences one or more brief attack (also referred to as a panic attack) of intense terror and apprehension, often marked by trembling, shaking, confusion, dizziness, nausea, and/or difficulty breathing. A panic attack is defined as a fear or discomfort that abruptly arises and peaks in less than ten minutes.

'Social anxiety disorder' is defined as an intense fear and avoidance of negative public scrutiny, public embarrassment, humiliation, or social interaction. Social anxiety often manifests specific physical symptoms, including blushing, sweating, and difficulty speaking.

'Post-traumatic stress disorder' (PTSD) is an anxiety disorder that results from a traumatic experience. Post-traumatic stress can result from an extreme situation, such as combat, natural disaster, rape, hostage situations, child abuse, bullying, or even a serious accident. Common symptoms include hypervigilance, flashbacks, avoidant behaviours, anxiety, anger and depression.

As used herein, the term "post-partum depression" (PPD, also known as postnatal depression) is a form of depression experienced by either parent of a newborn baby. Symptoms typically develop within 4 weeks of delivery of the baby and often include extreme sadness, fatigue, anxiety, loss of interest or pleasure in hobbies and activities, irritability, and changes in sleeping or eating patterns.

As used herein, the term 'substance abuse' means a patterned use of a drug in which the user consumes the substance in amounts or with methods that are harmful to themselves or others.

As used herein, the term 'an avolition disorder' refers to a disorder that includes as a symptom the decrease in motivation to initiate and perform self-directed purposeful activities.

In its various aspects, the invention relates to compounds of formula (I). The compounds of formula (I) (and as well as each of the compounds of formulae (I'), (II) and N(H)R²R³ described herein) comprise a C($^x$H)₃ moiety (and in some embodiments two such moieties) in which the ratio of deuterium:protium is greater than its natural isotopic abundance, i.e. the compound concerned comprises a methyl group in which the percentage of deuterium amongst the hydrogen atoms in the compounds of the formula is greater than its natural isotopic abundance in hydrogen, which is about 0.02 mol %.

In the compounds of formula (I), in accordance with particular embodiments of at least the first to sixth aspects of the invention, R¹ is independently selected from —OR⁴, —O(CO)R⁴, monohydrogen phosphate and —OH. In particular embodiments of these and other embodiments, R⁴ is methyl.

Sometimes, in the compounds of formulae (I), (I') and (II) (formulae (I') and (II) being described infra), in accordance with any relevant aspect or embodiment of the invention, n is 0 or 1. According to some embodiments, n is 0.

Where n is 1, R¹ (or R¹', in compounds of formulae (I') and (II)) is at the 4- or 5-position. For the avoidance of doubt, positions 4 and 5 refer to these positions with represents to the labelled structure of DMT depicted below:

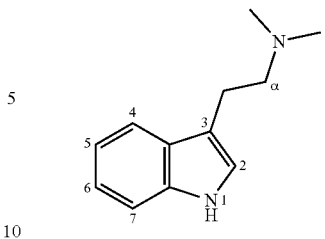

According to some embodiments, In the compounds of formula (I), in accordance with particular embodiments of at least the first to sixth aspects of the invention, n is 0, or n is 1 and R¹ is selected from 5-methoxy, 5-bromo, 4-acetoxy, 4-monohydrogen phosphate, 4-hydroxy and 5-hydroxy.

According to some embodiments of all aspects of the invention, n is 0, or n is 1 and R¹, or as appropriate R¹', is 5-methoxy.

Sometimes, in the compounds described herein having $^y$H moieties, these are deuterium (that is to say hydrogen in which the proportion of deuterium has been increased beyond its natural abundance); sometimes these $^y$H moieties are protium (that is to say hydrogen in which the proportion of deuterium has not been increased beyond its natural abundance).

For the avoidance of doubt, by a $^x$H or $^y$H being deuterium is meant that the atom concerned is enriched with deuterium, i.e. the hydrogen atoms of the resultant compound by virtue of this enrichment comprises a greater percentage of deuterium than that found naturally in hydrogen, which is about 0.02 mol %.

Where compounds described herein are indicated as being or described as substituted with deuterium, the compound concerned is enriched with deuterium by an amount that is dependent on the percentage of deuterium available in the reagents from which the compounds are derived. For example, and as described herein, the d₆-dimethylamino or d₃-monomethylamino portions of compounds of formulae (I), (I') and (II), wherein —NR²R³ is —N(CD₃)₂ and —N(H)CD₃ respectively, may be derived from dimethyl-d₇-amine, dimethyl-d₆-amine or methyl-d₃-amine (commonly available as HCl salts), which are available from chemical vendors in purities of deuterium that range from 98% to 99%. The purity of deuterium in the resultant d₆-dimethylamino or d₃-monomethylamino substituents is consequently between 98% and 99%. This means, as the skilled person will understand, that not all compounds of formula (I) (for example) will comprise d₆-dimethylamino or d₃-monomethylamino substituents—some may comprise d₀-d₅dimethylamino or d₀-d₃-monomethylamino substituents, but the average purity of deuterium is about 98% to 99%.

Sometimes, in the relevant compounds described herein, R² and R³ are both C($^x$H)₃, and in some of these embodiments both C($^x$H)₃ are the same. According to particular embodiments, both R² and R³ are CD₃.

In accordance with the second aspect of the invention, there is provided a compound of formula (I), with the proviso that this is not N,N-di(trideuteromethyl)tryptamine. The compound of the invention can, however, be a pharmaceutically acceptable salt of di(trideuteromethyl)tryptamine, for example di(trideuteromethyl)tryptamine fumarate; or other N,N-di(trideuteromethyl)tryptamines of formula (I), for example 5-methoxy,N,N-di(trideuteromethyl)tryptamine or a pharmaceutically acceptable salt thereof.

Compounds of formula (I), including the particular embodiments just described (including those in which n=0 and n=1, wherein $R^1$ is 5-methoxy) can, for example, be synthesised by following the reaction scheme set out in Scheme 1 below:

Scheme 1. Synthetic pathway for the production of examples (in which n = 0) of compounds of formula (I)

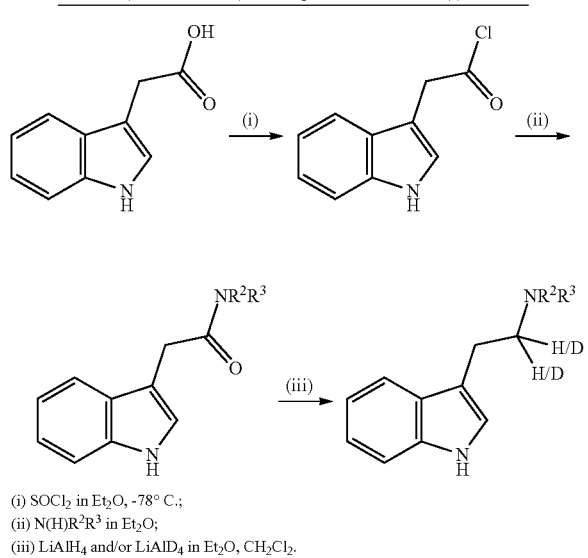

(i) $SOCl_2$ in $Et_2O$, -78° C.;
(ii) $N(H)R^2R^3$ in $Et_2O$;
(iii) $LiAlH_4$ and/or $LiAlD_4$ in $Et_2O$, $CH_2Cl_2$.

Scheme 1 depicts the synthesis of compounds of formula (I) in which n=0. Variations of the chemistry described (relevant for example to the synthesis of compounds of formula (I) in which n is other than 0) are well within the normal ability of a skilled person, using his or her common general knowledge and/or the teaching herein.

The chemistry depicted in Scheme 1 was reported by P. E. Morris and C. Chiao (supra). Deuterated compounds of or used in accordance with the various aspects of the invention, or indeed undeuterated compounds relevant to the present invention, which may be useful in embodiments of the third to sixth aspects of the invention as described herein, can also be synthesised following the chemistry depicted in Scheme 2, or variations of this chemistry.

Scheme 2. Additional synthetic pathway for the production of examples (in which n = 0) of compounds of formula (I)

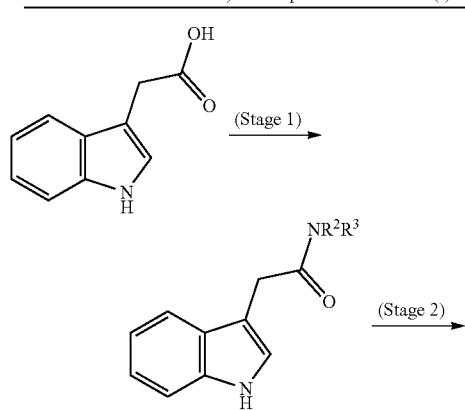

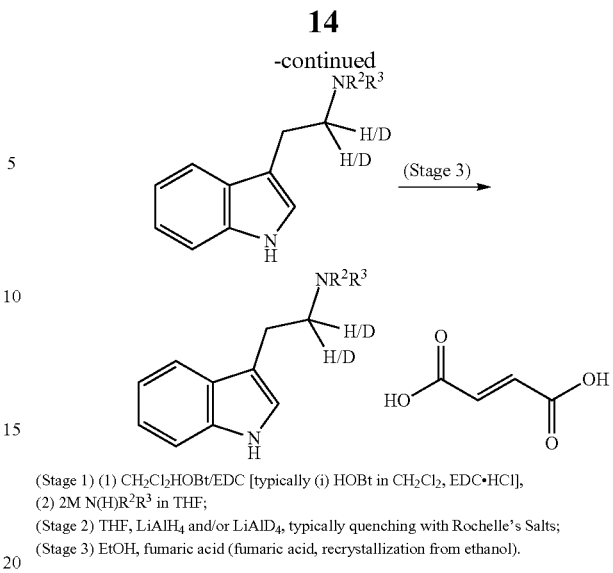

(Stage 1) (1) $CH_2Cl_2HOBt/EDC$ [typically (i) HOBt in $CH_2Cl_2$, EDC•HCl], (2) 2M $N(H)R^2R^3$ in THF;
(Stage 2) THF, $LiAlH_4$ and/or $LiAlD_4$, typically quenching with Rochelle's Salts;
(Stage 3) EtOH, fumaric acid (fumaric acid, recrystallization from ethanol).

As with Scheme 1, Scheme 2 depicts the synthesis of compounds of formula (I) in which n=0. Carrying out the chemistry described in this Scheme and variations thereof (discussed extensively below with regard to the seventh aspect of the invention) is well within the normal ability of a skilled person.

It will be understood that the formation of fumarate salts as depicted in Stage 3 of Scheme 2 may be varied to afford other pharmaceutically acceptable salts and that this salt formation step can also be carried out on the final product(s) depicted in Scheme 1.

Relative amounts of protium to deuterium as $^yH$ in the compounds synthesised may be controlled by varying the ratio of lithium aluminium hydride and lithium aluminium deuteride as the reducing agent (see for example WO 2020/245133 A1 (Small Pharma Ltd), supra). The proportion of protium and deuterium at these positions may be further varied if desired, for example to provide compositions according to the invention in a controllable way, by adding one or more of the protio or deutero compounds to the compositions described herein.

It will be seen from Scheme 1 that step (ii), and from Scheme 2 that Stage 1, serves to effect introduction of the amine moiety ($-NR^2R^3$) into the compounds. It will be understood that the synthesis of compounds of formula (I), which comprise at least one $C(^yH)_3$ moiety in which the percentage of deuterium is greater than its natural isotopic abundance in hydrogen, may be achieved through the use of appropriate deuterated monomethylamines and dimethylamines, which are commercially available. In particular, use of commercially available $d_7$-dimethylamine (i.e. $DN(CD_3)_2$), $d_6$-dimethylamine (i.e. di(trideuteromethyl)amine) and $d_3$-methylamine (i.e. trideuteromethylamine) allow access to compounds of formula (I), and in accordance with the seventh aspect of the invention, compounds of formula (I'), in which $-NR^2R^3$ is $-N(CD_3)_2$ and $-N(H)CD_3$.

Identification of the compositions resultant from the reduction step in Schemes 1 and 2 may be achieved, if desired, by chromatographic separation of the components of the mixtures by conventional means at the disposal of the skilled person, in combination with spectroscopic and/or mass spectrometric analysis.

Alternative compositions are obtainable by mixing undeuterated compounds, obtainable by Scheme 1 or Scheme 2 when the reducing agent is exclusively lithium aluminium hydride, with an α,α-dideutero compound obtainable from Scheme 1 or Scheme 2 when the reducing agent is exclusively lithium aluminium deuteride, it being understood when reference is made to reducing agents being exclusively lithium aluminium hydride or lithium aluminium deuteride that this refers to an ideal, and is ultimately subject to the purity of the reagent concerned, as discussed above.

The compositions described hereinabove may be further modified by adding one or more α-monodeutero compounds. Stocks of such compounds may be obtained, for example, from the chromatographic separation described above.

Scheme 3 depicts chemistry based on that known in the art for synthesising DMT, which may be deployed/modified to synthesise compounds of formula (I), in which substituent $R^1$ denotes hydrogen (i.e. wherein n=0) or the substituent $R^1$ as defined herein, and $R^2$ and $R^3$ are as defined herein. Whilst typically no more than one $R^1$ group will be present, pluralities of $R^1$ moieties are not excluded.

deuterium may be controlled through the use of mixtures of sodium borohydride and sodium borodeuteride or sodium borodeuteride (see, for example, the synthesis of DMT-d6 described by Oliveira et al. (supra).

Tryptamines are generally synthesised using methods adapted from Alexander Shulgin's pioneering publication TiHKAL: The Continuation (Berkeley, Calif., Transform Press, 1997). This discloses several alternative methods for synthesising DMT; the three step route starting from indole using (1) oxalyl chloride, (2) dimethylamine and (3) lithium aluminium hydride has been widely adopted (see top synthetic route depicted in Scheme 3), and analogous routes have been used to scale psilocybin under GMP controls (see, for example, WO 2019/073379 A1). Oxalyl chloride is very toxic and corrosive. It is severely irritating to eyes, skin, and the respiratory tract and reacts violently with water making it difficult to handle at scale.

The synthesis of DMT from auxin (a plant hormone and natural product, and the compound depicted first in both Schemes 1 and 2) has been reported by P. E. Morris and C.

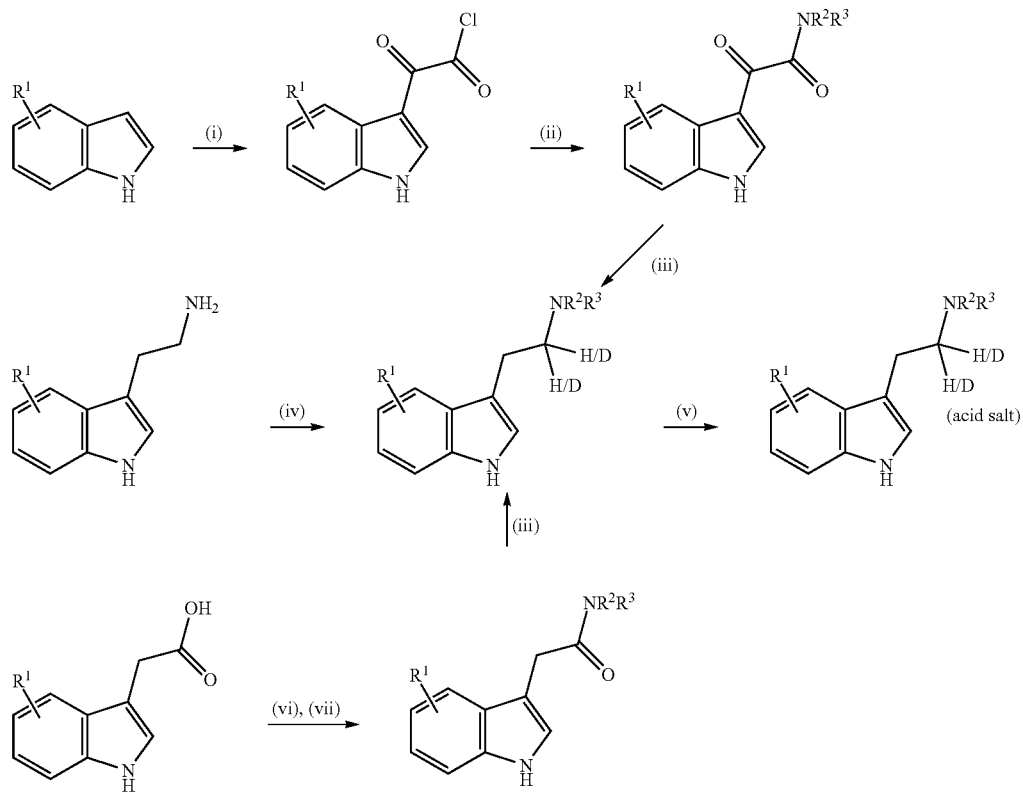

Scheme 3 Additional synthetic pathway for the production of optionally $R^1$-substituted compounds of formula (I)

(i) oxalyl chloride (ClC(O)C(O)Cl); (ii) N(H)R²R³; (iii) LiAlH₄ and/or LiAlD₄; (iv) formaldehyde, sodium cyanoborohydride; (v) additional pharmaceutical acceptable acid, for example fumaric acid to form salts of compounds or compositions of formula (I); (vi) SOCl₂, Et₂O; (vii) N(H)R₂R₃.

As with Schemes 1 and 2, Scheme 3 illustrates how the amine moiety (—NR²R³) is introduced into the compounds and how, in step (iii), relative proportions of protium to deuterium in the compounds (i.e. the constitution of substituents ʸH) may be controlled by varying the ratio of lithium aluminium hydride and lithium aluminium deuteride (see again, for example, WO 2020/245133 A1 (Small Pharma Ltd), supra). Step (iv) may be used to introduce C(³H)₃ moieties as $R^2$ and $R^3$ in which the amount of Chiao, supra (see again Scheme 1 and also the bottom synthetic route depicted in Scheme 3 (steps (vi), (vii) then (iii)). Whilst it is possible to use the oxalyl chloride route to make compounds of formula (I), an advantageous feature of the present invention is the avoidance of this and the provision of high-purity compounds of formula (I) without sacrificing yield. This is the chemistry depicted in Scheme 2, to which the seventh aspect of the invention relates, and which can be modified to provide $R^1$-containing compounds of formula (I) through the use of $R^1$-containing starting materials (or $R^{1'}$-containing starting materials), for example by modifying the chemistry described in Scheme 2 with the use of protecting groups, also described herein.

In particular, and in accordance with the seventh aspect of the invention, there is provided a method comprising synthesising a compound of formula (I'):

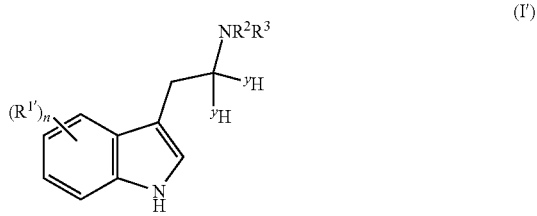

or a pharmaceutically acceptable salt thereof, comprising reacting a compound of formula (II):

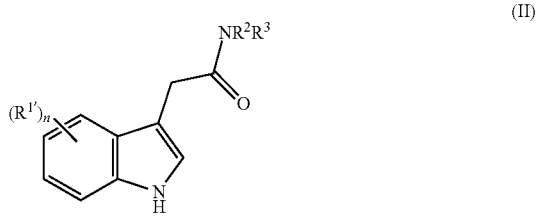

with $LiAlH_4$ and/or $LiAlD_4$, wherein:
$R^{1'}$ is independently selected from —$R^4$, —OPR, —$OR^4$, —F, —Cl, —Br and —I;
PR is a protecting group,
n is selected from 0, 1, 2, 3 or 4;
$R^2$ is $C(^xH)_3$;
$R^3$ is $C(^xH)_3$ or H;
each $R^4$ is independently selected from $C_1$-$C_4$alkyl; and
each $^xH$ and $^yH$ is independently protium or deuterium,
wherein a ratio of deuterium:protium in a $C(^xH)_3$ moiety in the compound of formula (I') is greater than that found naturally in hydrogen,
or a pharmaceutically acceptable salt thereof.

It will be understood that the reduction of the amide carbonyl group in compounds of formula (II) corresponds to Stage 2 in Scheme 2 and that optional substituent(s) $R^{1'}$ in the compounds of formulae (I') and (II) may be present.

In the compounds of formulae (I') and (II), PR is a protecting group. In other words, where an $R^{1'}$ group represents OPR, this denotes a protected hydroxyl group. The skilled person is well aware that during synthetic sequences it may be advantageous to protect sensitive or reactive groups on any of the molecules concerned. This is achieved by means of protecting groups, a concept with which the skilled person is completely familiar. Suitable protecting groups and the ways in which these may be used are described, for example, by T. W. Greene and P. G. M. Wutts in '*Protective Groups in Organic Synthesis*' 5th Edition, John Wiley and Sons, 2014.

When a compound of formula (I') is made with a —OPR group, this may be, and typically will be, removed after the reduction of the compound of formula (II) described in accordance with the method of the seventh aspect of the invention, using deprotection methods well known in the art (see again T. W. Greene and P. G. M. Wutts, supra). The hydroxyl group thereby revealed may be converted if desired into a —$OR^4$, —$O(CO)R^4$, or monohydrogen phosphate moiety (as defined herein). Such reactions represent particular embodiments of the seventh aspect of the invention.

According to such embodiments, the method of the seventh aspect of the invention further comprises, where a compound of formula (I') comprises a —OPR group, removing the protecting group and optionally (but typically) converting the resultant —OH group to a —$OR^4$, —O(CO)$R^4$, or monohydrogen phosphate moiety.

For example, to synthesise compounds of formula (I) having hydroxy, monohydrogen phosphate or acetyl substituents, a benzyloxy 2-(3-indolyl)-oxoacetamide having suitable $R^2$ and $R^3$ groups may be reduced with a desired ratio of lithium aluminium hydride and lithium aluminium deuteride to produce a benzyloxy-N,N-dimethyl tryptamine (optionally substituted once or twice at the α position with deuterium). The benzyl protecting group may then be removed, e.g. by hydrogenating with hydrogen and palladium on carbon, to form the corresponding hydroxy-tryptamine (optionally substituted at the α position with deuterium). The hydroxy group may be converted to a monohydrogen phosphate or an acetyl by reaction with either tetra-O-benzyl-pyrophosphate (followed by removal of the benzyl protecting group) or reaction with acetic anhydride (or other acid anhydride, acyl halide or other method of converting the —OH group to a —O(CO)$R^4$ moiety). See D. E. Nichols and S. Frescas, *Synthesis*, 1999, 6, 935-938 for further information on this synthetic strategy.

According to particular embodiments of the method of the seventh aspect of the invention, $R1'$ in formulae (I') and (II) is not OPR, i.e. is independently selected from —$R^4$, —$OR^4$, —F, —Cl, —Br and —I, the compounds of formula (I') according to such embodiments representing a subset of the compounds of formula (I) defined in accordance with the first aspect of the invention. According to even more specific embodiments of the method of the seventh aspect of the invention, including the embodiments described below, there is no $R^{1'}$ substituent (i.e. n=0) or $R^{1'}$ is 5-OMe.

In Scheme 2, Stage 1 comprises reacting the depicted carboxylic acid reactant with two or more coupling agents to produce an activated compound and reacting the activated compound with an amine to produce the amide depicted. Stage 2 comprises reacting the amide with $LiAlH_4$ and/or $LiAlD_4$ and corresponds to the method of the seventh aspect of the invention. Stage 3 depicts optional salt formation. Where desired/appropriate, any deprotection (removal) of a protecting group and conversion as immediately hereinbefore described will typically take place after Stage 2 and before Stage 3.

Advantageously, the method of the seventh aspect of the invention avoids the use of problematic oxalyl chloride and employs starting materials that may be derived from auxin (indole-3-acetic acid). High quality and pure auxins (derivatives of the carboxylic acid starting material depicted in Scheme 2 (comprising substituent(s) $R^{1()}$ are commercially available at scale and/or can be readily synthesised via the Fischer synthesis, Bartoli synthesis, Japp-Klingemann synthesis or Larock synthesis (see, for example, M. B. Smith and J. March, 2020, *March's Advanced Organic Chemistry*, 8th edition, Wiley, N.J.).

The method of Scheme 2, which represents an exemplary, specific embodiment of the seventh aspect of the invention is efficient, scalable, compatible with Current Good Manufacturing Practices (cGMP), and is suitable for the production of high purity compounds of formula (I). For example, the method is suitable for the production of compounds of formula (I) in batch scales ranging from 1 g to 100 kg and is suitable for the production of compounds of formula (I) with a purity of >99.9% and overall yield of 50% or more.

It will be understood from the foregoing discussion that, according to particular embodiments, the method of the seventh aspect of the invention may further comprise making the compound of formula (II) by:
(i) reacting a compound of formula (III)

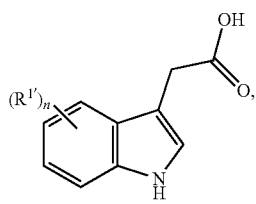

(III)

wherein $R^{1'}$ and n are as defined for formula (I'), with two or more coupling agents to produce an activated compound; and
(ii) reacting the activated compound with an amine having the formula $R^2R^3NH$ or $R^2R^3ND$, the definitions of n, $R^{1'}$, $R^2$ and $R^3$ corresponding to those in the compound of formula (II).

It will be understood that the starting material depicted in Scheme 2 is an example of a compound of formula (III) in which n=0.

Typically, n herein will be 0 or 1, often (but by no means necessarily) 0. Examples of suitable starting materials of formula (III) where n is 1 are, for example, include 4- and 5-hydroxyindole acetic acid.

For the avoidance of doubt, where a reagent is expressed herein as a number of equivalents, this is with respect to the molar equivalents of the reactant compounds of for reagents in Stages 1 to 3 of Scheme 2.

The term "coupling agent" refers to an agent which facilitates the chemical reaction between an amine and a carboxylic acid. In some embodiments, the two or more coupling agents comprise a carboxylic acid activating agent, i.e. an agent which reacts with the carboxylic acid moiety in Stage 1 (i.e. in compounds of formula (III)) to produce a compound comprising an activated moiety derived from the original carboxylic acid moiety, which is more likely to react with an amine than the original carboxylic acid moiety.

An additive coupling agent (also referred to herein as an "additive") is an agent which enhances the reactivity of a coupling agent. In some embodiments, the additive is a compound capable of reacting with the product of the reaction of the starting carboxylic acid and the coupling agent (the product being a compound comprising an activated moiety) to produce a compound comprising an even more activated moiety that is more likely to react with an amine than the original activated moiety.

Unless a context indicates otherwise, amine means secondary amine.

High-performance liquid chromatography (HPLC), is a technique in analytical chemistry used to separate, identify, and quantify each component in a mixture. For a review of HPLC, see A. M. Sabir et al., *Int. Res. J. Pharm.*, 2013, 4, 4, 39-46.

Solvents referred to herein include MeCN (acetonitrile), DCM (dichloromethane), acetone, IPA (isopropyl alcohol), iPrOAc (isopropyl acetate), TBME (t-butyl methyl ether), THF (tetrahydrofuran), 2-MeTHF (2-methyl tetrahydrofuran), EtOAc (ethyl acetate), ethanol and toluene. As used herein, the term ether solvent means a solvent containing an alkyl-O-alkyl moiety, wherein the two alkyl components may be connected. Ether solvents include diethyl ether, TBME, THF and 2-MeTHF.

A drying agent is a chemical used to remove water from an organic compound that is in solution. Examples of drying agents include calcium chloride, magnesium sulphate, and sodium sulphate. Drying agents described herein are typically magnesium sulphate.

An acidic reagent suitable for crystallising a pharmaceutically acceptable salt of a compound of formula (I) (or (I')) is an acid which forms a non-toxic acid anion. Examples include hydrochloride, hydrobromide, sulphate, phosphate or acid phosphate, acetate, maleate, fumarate, lactate, tartrate, citrate and gluconate.

Aqueous basic solution means a mild base suitable for workup, for example a 10% potassium carbonate solution.

As described above, Scheme 2 depicts advantageous methods of synthesising compounds of formula (I) (or (I')), or a pharmaceutically acceptable salts thereof, comprising Stage 1 and Stage 2. Stage 1 comprises:
(i) reacting a starting carboxylic acid (auxin or a derivative thereof) with two or more coupling agents to produce an activated compound; and
(ii) reacting the activated compound with an amine having the formula $(R^2)(R^3)NH$ to produce a compound of formula (II).

The activated compound is the product of the reaction between the auxin starting material and the two or more coupling agents. Where the two or more coupling agents comprise carboxylic acid activating agents, the activated compound comprises an activated moiety, derived from the original carboxylic acid moiety, which is more likely to react with an amine than the original carboxylic acid moiety.

In some embodiments, the two or more coupling agents comprise a carboxylic acid activating agent. In some embodiments, the two or more coupling agents comprise an additive coupling agent. In some embodiments, the additive is capable of reacting with the product of the reaction of the starting carboxylic acid and the coupling agent (the product being a compound comprising an activated moiety) to produce an activated compound comprising an even more activated moiety that is more likely to react with an amine than the original activated moiety.

Often, the two or more coupling agents comprise a carboxylic acid activating agent and an additive coupling agent.

In some embodiments, at least one of the two or more coupling agents is selected from the group consisting of carbodiimide coupling agents, phosphonium coupling agents and 3-(diethoxy-phosphoryloxy)-1,2,3-benzo[d]triazin-4(3H)-one (DEPBT), such as a carbodiimide coupling agent or a phosphonium coupling agent. In some embodiments, at least one of the two or more coupling agents is a carbodiimide coupling agent.

A carbodiimide coupling agent is a coupling agent which comprises a carbodiimide group R'—N═C═N—R", wherein R' and R" are hydrocarbyl groups optionally substituted with heteroatoms selected from nitrogen, sulfur and oxygen, typically nitrogen. Often, R' and R" are independently selected from $C_1$-$C_6$alkyl, $C_5$-$C_6$cycloalkyl, $C_1$-$C_6$alkylamino and morpholino$C_1$-$C_6$alkyl. Often, $C_1$-$C_6$alkyl is $C_3$alkyl, $C_5$-$C_6$cycloalkyl is cyclohexyl, $C_1$-$C_6$alkylamino is dimethylaminopropyl and/or morpholino$C_1$-$C_6$alkyl is morpholinoethyl.

In some embodiments, the carbodiimide coupling agent is any one selected from the group consisting of dicyclohexylcarbodiimide (DCC), diisopropylcarbodiimide (DIC), (N-(3-Dimethylaminopropyl)-N'-ethylcarbodiimide (EDC) and 1-cyclohexyl-(2-morpholinoethyl)carbodiimide metho-p-toluene sulfonate (CMCT). In some embodiments, the carbodiimide coupling agent is any one selected from the group consisting of dicyclohexylcarbodiimide (DCC), diisopropylcarbodiimide (DIC) and (N-(3-Dimethylaminopropyl)-N'-ethylcarbodiimide (EDC). Often, the carbodiimide coupling agent is N-(3-Dimethylaminopropyl)-N'-ethylcarbodiimide (EDC), typically as a hydrochloride salt (EDC·HCl). EDC or EDC·HCl are particularly preferred as they are non-toxic and are highly water soluble, facilitating their virtually complete removal in workup and wash steps of Stage 1.

A phosphonium coupling agent comprises a phosphonium cation and a counterion, typically a hexafluorophosphate anion. In some embodiments, the phosphonium cation is of formula $[PR^a{}_3R^b]^+$ wherein $R^a$ is di($C_1$-$C_6$)alkylamino or pyrrolidinyl and $R^b$ is halo or a hydrocarbyl group optionally substituted with nitrogen and/or oxygen atoms. Often, $R^b$ is bromo, benzotriazol-1-yloxy or 7-aza-benzotriazol-1-yloxy.

In some embodiments, the phosphonium coupling agent is any one selected from the group consisting of benzotriazol-1-yloxy-tris(dimethylamino)-phosphonium hexafluorophosphate (BOP), bromo-tripyrrolidino-phosphonium hexafluorophosphate (PyBrOP), benzotriazol-1-yloxy-tripyrrolidino-phosphonium hexafluorophosphate (PyBOP), 7-aza-benzotriazol-1-yloxy-tripyrrolidinophosphonium hexafluorophosphate (PyAOP) and ethyl cyano(hydroxyimino)acetato-$O_2$) tri-(1-pyrrolidinyl)-phosphonium hexafluorophosphate (PyOxim).

In some embodiments, at least one of the two or more coupling agents is an additive coupling agent selected from the group consisting of 1-hydroxybenzotriazole (HOBt), hydroxy-3,4-dihydro-4-oxo-1,2,3-benzotriazine (HOOBt), N-hydroxysuccinimide (HOSu), 1-hydroxy-7-azabenzotriazole (HOAt), ethyl 2-cyano-2-(hydroximino)acetate (Oxyma Pure), 4-(N,N-Dimethylamino)pyridine (DMAP), N-hydroxy-5-norbornene-2,3-dicarboximide (HONB), 6-chloro-1-hydroxybenzotriazole (6-Cl-HOBt), 3-hydroxy-4-oxo-3,4-dihydro-1,2,3-benzotriazine (HODhbt), 3-hydroxy-4-oxo-3,4-dihydro-5-azabenzo-1,2,3-triazene (HODhat) and 3-hydroxyl-4-oxo-3,4-dihydro-5-azepine benzo-1,3-diazines (HODhad).

In some embodiments, at least one of the two or more coupling agents is an additive coupling agent selected from the group consisting of 1-hydroxybenzotriazole (HOBt), hydroxy-3,4-dihydro-4-oxo-1,2,3-benzotriazine (HOOBt), N-hydroxysuccinimide (HOSu), 1-hydroxy-7-azabenzotriazole (HOAt), ethyl 2-cyano-2-(hydroximino)acetate (Oxyma Pure) and 4-(N,N-Dimethylamino)pyridine (DMAP).

In some embodiments, at least one of the two or more coupling agents is an additive coupling agent which is 1-hydroxybenzotriazole.

In some embodiments, the two or more coupling agents consist of a coupling agent and an additive coupling agent wherein the coupling agent and additive coupling agent may be as described in the above embodiments.

A benefit of using both a coupling agent and an additive coupling agent is an increased rate of formation of the Stage 1 product from the starting material and an amine having the formula $(R^2)(R^3)NH$. In addition, when an additive coupling agent is used together with a carbodiimide coupling agent, the likelihood of unwanted side reactions may be reduced. For example, reaction of a starting carboxylic acid with a carbodiimide coupling reagent is likely to form an O-acylisourea. This may undergo a rearrangement to form an N-acylurea, which is a stable compound unlikely to react with an amine. Additive coupling reagents may react with O-acylureas before rearrangement to N-acylureas, and produce compounds that go on to react with an amine, rather than inactive N-acylureas.

Therefore, in some embodiments, the two or more coupling agents consist of a carbodiimide coupling agent and an additive coupling agent.

In particular embodiments, the two or more coupling agents consist of N-(3-Dimethylaminopropyl)-N'-ethylcarbodiimide (EDC), typically as a hydrochloride salt (EDC·HCl), and 1-hydroxybenzotriazole (HOBt).

Often, an excess of coupling agent with respect to start a carboxylic acid is used. In some embodiments, the ratio of coupling agent:starting carboxylic acid is about 1:1 to about 3:1, typically about 1:1 to about 2:1 and most typically about 1:1 to about 1.5:1.

Often, an excess of additive coupling agent with respect to starting carboxylic acid is used. In some embodiments, the ratio of additive coupling agent:starting carboxylic acid is about 1:1 to about 3:1, typically about 1:1 to about 2:1 and most typically about 1:1 to about 1.5:1.

In some embodiments, where the two or more coupling agents comprise a coupling agent and an additive coupling agent, a ratio of coupling agent:starting carboxylic acid and additive coupling agent:starting carboxylic acid of about 1:1 to about 1.5:1 is used.

As described above, Stage 1 of Scheme 2 comprises reacting the activated compound (the product of reacting a starting carboxylic acid, for example of formula (III)) with two or more coupling agents) with an amine having the formula $(R^2)(R^3)NH$ to produce the product of Stage 1.

The ratio of amine:starting carboxylic acid employed in the method is often about ≥1:1. In some embodiments, the ratio of amine:starting carboxylic acid is about 1:1 to about 3:1, typically about 1:1 to about 2:1.

In some embodiments, Stage 1 further comprises isolating the resultant compound (the amide of formula (II)). The skilled person is aware of techniques in the art suitable for isolation of such compounds for example, such amides may be extracted into an organic solvent such as dichloromethane or ethyl acetate, washed with an aqueous solution such as an aqueous basic solution, and concentrated. To increase purity, the isolated amide may be recrystallized. The skilled person is aware of techniques that are suitable for doing this for example, the amide may be dissolved in the minimum amount of solvent at a particular temperature (e.g. at ambient temperature (e.g. about 15 to about 25° C.) or at elevated temperatures where heat is applied to the solution) and the resultant solution cooled to encourage precipitation. Alternatively, or additionally, the volume of the solution may be reduced to encourage precipitation, e.g. by simple evaporation at ambient temperature and pressure. Alternatively, or in addition, an anti-solvent may be used (in which the amide is less soluble than the solvent already present).

Isolated amides are stable and may be stored as solids at ambient temperature, e.g. at about 15 to about 25° C., in the air. They may, but need not be, stored under inert conditions, e.g. under nitrogen or argon, or at reduced temperatures, e.g. in a refrigerator or freezer.

Typically, steps (1) and (2) of Stage 1 of Scheme 2 (for example, but not necessarily (1) $CH_2Cl_2$/HOBt/EDC and (2) 2 M $N(H)R^2R^3$ in THF (the illustrative conditions mentioned in the legend to Scheme 2 above) are carried out in a suitable solvent. The skilled person is able to assess which solvents are suitable for these steps. Examples of suitable solvents include dichloromethane (DCM), acetone, isopropyl alcohol (IPA), isopropyl acetate (iPrOAc), tert-butyl methyl ether (TBME), 2-methyl tetrahydrofuran (2-MeTHF) and ethyl acetate (EtOAc). In some embodiments, steps (1) and (2) of Stage 1 are carried out in dichloromethane.

Steps (1) and (2) of Stage 1 are carried out at a suitable temperature and the skilled person is able to assess which temperatures are suitable for these steps. Often, steps (1) and (2) of Stage 1 are carried out at temperatures of about 10° C. to about 30° C. In some embodiments, steps (1) and (2) of Stage 1 are carried out at room temperature (e.g. at about 20 to about 30° C. (typically about 20° C.)).

In specific embodiments, Stage 1 of the method depicted in Scheme 2, and thus in particular embodiments of the seventh aspect of the invention (involving reaction of compounds of formula (III)) comprises the steps of:
(1) contacting a starting carboxylic acid of formula (III) and between 1 and 1.5 equivalents of an additive coupling agent, and between 1 and 1.5 equivalents of a carbodiimide coupling agent to produce a first composition; and
(2) contacting the first composition with between 1 and 2 equivalents of an amine having the formula $R^2R^3NH$ or $R^2R^3ND$ to produce a second composition.

In some embodiments, 1 g or more, such as 1 g to 100 kg or 1 g to 1 kg of a starting compound (the carboxylic acid) is employed in the method of the invention.

In some embodiments, the contacting of steps (1) and (2) is carried out in the presence of a first solvent, such as between 5 and 20 volumes of a first solvent. The first solvent may be selected from any one of dichloromethane (DCM), acetone, isopropyl alcohol (IPA), isopropyl acetate (iPrOAc), tert-butyl methyl ether (TBME), 2-methyl tetrahydrofuran (2-MeTHF) and ethyl acetate (EtOAc). Typically, the first solvent is DCM.

In some embodiments, step (1) further comprises stirring or agitating the first composition. The first composition may be stirred or agitated for at least 30 minutes, such as 30 minutes to 3 hours or 30 minutes to 2 hours, preferably at least 1 hour, for example 1 to 3 hours or 1 to 2 hours. The first composition may be maintained at a temperature of between 10° C. and 30° C.

In some embodiments, the amine of step (2) is dissolved in a solvent, such as tetrahydrofuran (THF) or ether, prior to contacting. The amine may be present in the solvent at a concentration of about 2 M. Typically, the amine of step (2) is dissolved in THF.

In some embodiments, step (2) further comprises stirring or agitating the second composition. The second composition may be stirred or agitated for at least 30 minutes, such as 30 minutes to 3 hours or 30 minutes to 2 hours, preferably at least 1 hour, for example 1 to 3 hours or 1 to 2 hours. The second composition may be maintained at a temperature of between 10° C. and 30° C.

In some embodiments, step (2) further comprises contacting the second composition with an aqueous basic solution to produce a third composition, for example contacting the second composition with between 2 and 10 volumes of an aqueous basic solution such as an aqueous solution comprising potassium carbonate.

In some embodiments, step (2) further comprises stirring or agitating the third composition. The third composition may be stirred or agitated for at least 1 minute, such as 1 to 15 minutes or 1 to 10 minutes, preferably at least 5 minutes, for example 5 to 15 minutes or 5 to 10 minutes. The third composition may be maintained at a temperature of between 10° C. and 30° C.

In some embodiments, where the third composition comprises an organic and an aqueous component, step (2) further comprises separating the organic component from the aqueous component. In some embodiment, the organic component is separated from the aqueous component within 8 hours of the contacting of step (1).

In even more specific embodiments, Stage 1 in methods of the seventh aspect of the invention comprises the steps of:
i. adding to a first vessel 1 g or more of a starting carboxylic acid of formula (III) and between 1 and 1.5 equivalents of an additive coupling agent,
ii. adding to the first vessel between 5 and 20 volumes of a first solvent selected from DCM, acetone, IPA, iPrOAc, TBME, 2-MeTHF and EtOAc,
iii. adding to the first vessel between 1 and 1.5 equivalents of a carbodiimide coupling agent,
iv. stirring the contents of the first vessel for at least 30 minutes, preferably at least 1 hour (such as 1 to 2 hours), at between 10° C. and 30° C.,
v. adding to the first vessel between 1 and 2 equivalents of an amine having the formula $R^2R^3NH$ or $R^2R^3ND$, wherein the amine is preferably dissolved in an ether solvent,
vi. further stirring the contents of the first vessel for at least 30 minutes, preferably at least 1 hour (such as 1 to 2 hours), at between 10° C. and 30° C.,
vii. adding to the first vessel between 2 and 10 volumes of an aqueous basic solution,
viii. further stirring the contents of the first vessel for at least 1 minute, preferably at least 5 minutes (such as 5 to 10 minutes), at between 10° C. and 30° C.,
ix. allowing an immiscible organic fraction to separate from an aqueous fraction, wherein the organic fraction comprises the amide product of Stage 1, and
x. removing the organic fraction comprising the amide product,
wherein steps i. to x. are carried out within a single 8 hour period.

In some embodiments, the first solvent is DCM.
In some embodiments, the amine is dimethylamine. In some embodiments, the amine is dissolved in THF, for example at a concentration of 2 M.

In some embodiments, the aqueous basic solution comprises potassium carbonate.

In even more specific embodiments, Stage 1 of the method of Scheme 2 further comprises the steps of:
xi. drying the organic fraction with a drying agent, for example a drying agent selected from calcium chloride, magnesium sulphate, and sodium sulphate,
xii. filtering the organic fraction,
xiii. concentrating the organic fraction, for example under vacuum such as under a pressure of less than 1 atmosphere,
xiv. adding the concentrated organic fraction to a second vessel,
xv. adding between 2 and 10 volumes of a second solvent to the second vessel, wherein the second solvent is selected from IPA, EtOAc, IPrOAc, acetonitrile (MeCN), TBME, THF, 2-MeTHF and toluene,
xvi. stirring the contents of the second vessel for at least 1 hour, preferably at least 2 hours (such as 2 to 3 hours), at temperatures of between 45° C. and 55° C., xvii. cooling the contents of the second vessel to temperatures of between 15° C. and 25° C., xviii. filtering contents of the second vessel to obtain a filtrate, wherein the filtrate comprises the amide product of Stage 1, and xix. drying the filtrate.

In some embodiments, the drying agent of step xi. is magnesium sulphate. In some embodiments, the solvent of step xv. is selected from TBME and IPA.

Stage 2 of the method of Scheme 2 comprises reacting the amide product of Stage 1 (the compound of formula (II)) with $LiAlH_4$ and/or $LiAlD_4$ to produce a compound of formula (I'). Optionally, as described above, it may be desired to convert certain compounds of formula (I') to compounds of formula (I) as described herein.

As described above, $LiAlH_4$, $LiAlD_4$ or mixtures of the two may be reacted with the amide. In preferred embodiments, Stage 2 of the method comprises reacting the amide with a mixture of $LiAlH_4$ and $LiAlD_4$. Such mixtures may comprise $LiAlD_4$ and comprise between 0.1 and 99.9% hydride. Mixtures of between 2% and 98% lithium aluminium hydride or between 2% and 98% lithium aluminium deuteride may be employed. Sometimes, mixtures of $LiAlH_4$ and $LiAlD_4$ consist essentially of 98% $LiAlD_4$/2% $LiAlH_4$. Sometimes, such mixtures consist essentially of 95% $LiAlD_4$/5% $LiAlH_4$, 95% $LiAlD_4$/5% $LiAlH_4$, 85% $LiAlD_4$/15% $LiAlH_4$, 80% $LiAlD_4$/20% $LiAlH_4$, 75% $LiAlD_4$/25% $LiAlH_4$, 70% $LiAlD_4$/30% $LiAlH_4$, 65% $LiAlD_4$/35% $LiAlH_4$, 60% $LiAlD_4$/40% $LiAlH_4$, 55% $LiAlD_4$/45% $LiAlH_4$, 50% $LiAlD_4$/50% $LiAlH_4$, 45% $LiAlD_4$/55% $LiAlH_4$, 40% $LiAlD_4$/60% $LiAlH_4$, 35% $LiAlD_4$/65% $LiAlH_4$, 30% $LiAlD_4$/70% $LiAlH_4$, 25% $LiAlD_4$/75% $LiAlH_4$, 20% $LiAlD_4$/80% $LiAlH_4$, 15% $LiAlD_4$/85% $LiAlH_4$, 10% $LiAlD_4$/90% $LiAlH_4$, 5% $LiAlD_4$/95% $LiAlH_4$, or 2% $LiAlD_4$/98% $LiAlH_4$.

By the mixtures of $LiAlH_4$ and $LiAlD_4$ consisting essentially of specified percentages of $LiAlH_4$ and $LiAlD_4$ is meant that the mixture may comprise additional components (other than $LiAlH_4$ and $LiAlD_4$) but that the presence of these additional components will not materially affect the essential characteristics of the mixture. In particular, mixtures consisting essentially of $LiAlH_4$ and $LiAlD_4$ will not comprise material amounts of agents that are detrimental to the reduction of amides to produce compounds of formula (I') (e.g. material amounts of agents that react with $LiAlH_4$ and $LiAlD_4$, the amide reactant and/or compounds of formula (I') in a way that inhibits the reduction of the carbonyl moiety of the amides of formula (II) to produce compounds of formula (I').

The amount of $LiAlH_4$ or $LiAlD_4$ comprised in mixtures of the two depends on the degree of α-deuteration sought in the compound of formula (I') (and (I)). For example, where compounds of formula (I(')) are sought in which one $^{J}H$ is protium and the other is deuterium, a mixture of 50% $LiAlH_4$ and 50% $LiAlD_4$ may be preferred. Alternatively, where a mixture of compounds of formula (I')) is sought, in which approximately half of the compounds comprise two deuterium atoms at the α-position (i.e. both $^{x}H$ are deuterium) and approximately half of the compounds comprise one deuterium atom and one protium atom at the α-position (i.e. one $^{J}H$ is deuterium and the other is protium), a mixture of 25% $LiAlH_4$ and 75% $LiAlD_4$ may be preferred.

The amount of $LiAlH_4$ and/or $LiAlD_4$ employed relative to the amide being reduced in Stage 2 of Scheme 2 is often ≤1:1. For the avoidance of doubt, the ratios of $LiAlH_4$ and/or $LiAlD_4$ relative to the amide refer to the total amount of $LiAlH_4$ and/or $LiAlD_4$ used with respect to the amide of formula (II). In some embodiments, the ratio of $LiAlH_4$ and/or $LiAlD_4$:compound of formula (II) is 0.5:1 to 1:1, such as 0.8:1 to 1:1. In some embodiments, the ratio of $LiAlH_4$ and/or $LiAlD_4$:compound of formula (II) is 0.9:1.

Typically, Stage 2 of Scheme 2 is carried out in a suitable solvent. The skilled person is able to assess which solvents are suitable for this. Examples of suitable solvents include ethers such as THF and diethyl ether. In some embodiments, Stage 2 is carried out in THF.

In some embodiments, the $LiAlH_4$ and/or $LiAlD_4$ is provided as a solution or suspension of $LiAlH_4$ and/or $LiAlD_4$ in a suitable solvent such as an ether, for example THF or diethyl ether, typically THF.

Stage 2 of Scheme 2 is carried out at a suitable temperature and the skilled person is able to assess which temperatures are suitable for these steps. Often, Stage 2 of Scheme 2 is carried out at temperatures of about −5° C. to about 65° C.

In some embodiments, Stage 2 of scheme 2 further comprises isolating the compound or compounds resultant from the reduction the skilled person is aware of techniques in the art suitable for doing this for example, on quenching the reaction (e.g. with an aqueous solution of a tartrate salt such as Rochelle's salts), the product resultant from Stage 3 of Scheme 2 may be extracted into an organic solvent such as an ether, e.g. THF or diethyl ether, washed with an aqueous solution such as an aqueous basic solution, and concentrated. The isolated compound from Stage 2 of Scheme 2 may be recrystallized. The skilled person is aware of techniques that are suitable for such recrystallisations. Examples of recrystallisation techniques described with respect to recrystallisation of compounds resultant from Stage 2 of Scheme 2 apply mutatis mutandis to recrystallisation of salts of these compounds (resultant from Stage 3).

In some embodiments, about 1 g or more, such as about 1 g to about 100 kg or about 1 g to about 1 kg of a compound resultant from Stage 2 of Scheme 2 is employed.

In specific embodiments, Stage 2 of Scheme 2 comprises contacting a compound resultant from Stage 1 (i.e. a compound of formula (II)) and between about 0.8 and about 1 equivalents, such as about 0.9 equivalents of $LiAlH_4$ and/or $LiAlD_4$ to produce a first composition.

In some embodiments, the contacting is carried out in the presence of a solvent such as an ether, e.g. THF or diethyl ether, typically THF.

In some embodiments, the contacting comprises dropwise addition of $LiAlH_4$ and/or $LiAlD_4$ to an amide, wherein $LiAlH_4$ and/or $LiAlD_4$ is provided as a solution or suspension of $LiAlH_4$ and/or $LiAlD_4$ in a suitable solvent, such as an ether, e.g. THF or diethyl ether. In some embodiments, $LiAlH_4$ and/or $LiAlD_4$ is provided as a 2.4 M or 2 M solution or suspension of $LiAlH_4$ and/or $LiAlD_4$ in THF. In some embodiments, the $LiAlH_4$ and/or $LiAlD_4$ is provided as a 2 M solution or suspension of $LiAlH_4$ and/or $LiAlD_4$ in THF.

In some embodiments, the contacting is carried out at temperatures of about −5° C. to about 65° C.

In some embodiments, Stage 2 further comprises stirring or agitating the first composition. The first composition may be stirred or agitated for about 1 hour to about 6 hours, typically for about 2 hours. The first composition may be stirred or agitated at a temperature of about 55° C. to about 65° C. In some embodiments, the first composition is stirred or agitated at a temperature of about 55° C. to about 65° C. and then cooled to temperatures of about 10° C. to about 30° C.

In some embodiments, the amide is contacted with about 0.9 equivalents of $LiAlH_4$ and/or $LiAlD_4$.

In specific embodiments, Stage 2 of Scheme 2 comprises the steps of:
  i. adding to a third vessel 1 g or more (such as 1 g to 1 kg) of an amide to be reduced,
  ii. adding to the third vessel between 5 and 20 volumes of an ether solvent,
  iii. adding to the third vessel, dropwise over at least 15 minutes (e.g. 15 to 30 minutes), a solution of between 0.8 and 1 equivalents of $LiAlH_4$ and/or $LiAlD_4$ in the ether solvent at a temperature of between −5° C. and 65° C.,
  iv. stirring the contents of the third vessel at between 55° C. and 65° C. for between 1 hour and 6 hours, preferably 2 hours, and
  v. cooling the contents of the third vessel to between 10° C. and 30° C.,
wherein the contents of the third vessel comprise a compound of formula (I')

In some embodiments, the ether solvent is THF. In some embodiments, 0.9 equivalents of $LiAlH_4$ and/or $LiAlD_4$ are added to the third vessel in step iii. The $LiAlH_4$ and/or $LiAlD_4$ is typically added to the third vessel as a 2.4 M or 2 M solution in THF. In some embodiments, the $LiAlH_4$ and/or $LiAlD_4$ is added to the third vessel as a 2 M solution in THF.

In even more specific embodiments, Stage 2 of Scheme 2 comprises a workup comprising the steps of:
  vi. adding between 5 and 20 volumes of an aqueous solution of a tartrate salt (such as Rochelle's salts) to a fourth vessel,
  vii. adding a composition comprising crude compound of formula (I), over at least 15 minutes (such as 15 minutes to 1 hour), preferably at least 30 minutes (such as 30 minutes to 1 hour), to the fourth vessel at between 15° C. and 25° C., and
  viii. stirring the contents of the fourth vessel at between 15° C. and 25° C. for at least 30 minutes (such as 30 minutes to 1 hour).

For the avoidance of doubt, the composition comprising crude compound of formula (I') refers to the contents of the third vessel on completion of step v. of Stage 2, described above.

In further specific embodiments, Stage 2 of Scheme 2 further comprises the steps of:
  ix. allowing an organic fraction to separate from an aqueous fraction, wherein the organic fraction comprises the compound of formula (I'),
  x. removing the aqueous fraction from the fourth vessel,
  xi. adding between 5 and 20 volumes of a brine solution to the fourth vessel,
  xii. stirring the contents of the fourth vessel at a temperature between 15° C. and 25° C. for at least 5 minutes (such as 5 to 15 minutes),
  xiii. removing the organic fraction comprising the compound of formula (I') as a freebase,
  xiv. drying the organic fraction using a drying agent, such as a drying agent selected from calcium chloride, magnesium sulphate, and sodium sulphate,
  xv. filtering the organic fraction, and
  xvi. concentrating the organic fraction, for example under vacuum such as under a pressure of less than 1 atmosphere.

Isolated compounds of formula (I') (produced via Stage 2) are stable and may be stored as solids at ambient temperature, e.g. at about 20° C., in the air. They may, but need not be, stored under inert conditions, e.g. under nitrogen or argon, or at reduced temperatures, e.g. in a refrigerator or freezer. In some embodiments, the compound of formula (I) is stored in a solvent, for example dissolved in ethanol. In some embodiments, the compound of formula (I') is stored in a solvent for more than 8 hours, typically more than 12 hours.

As described above, the method of Scheme 2 provides a method of or comprising synthesising a compound of formula (I'), or a pharmaceutically acceptable salt thereof. In some embodiments, the invention provides a method of or comprising synthesising a pharmaceutically acceptable salt of formula (I'). A pharmaceutically acceptable salt may be formed from a compound of formula (I') by reaction with a suitable acid. Thus, in some optional embodiments, the method of Scheme 2 comprises Stage 3 (as is depicted in Scheme 2), in which the compound of formula (I') is reacted with an acidic reagent to produce a pharmaceutically acceptable salt of the compound of formula (I') in some embodiments, the acidic reagent is suitable for crystallising a pharmaceutically acceptable salt of the compound of formula (I'). It will be understood that, in embodiments in which compounds of formula (I') comprise a moiety of formula OPR, the protecting group PR will typically be removed and the resultant hydroxyl group optionally manipulated as described herein prior to Stage 3 (formation of pharmaceutically acceptable salts).

Thus, in some embodiments, the invention provides a method of synthesising a compound of formula (I) or (I'), or a pharmaceutically acceptable salt thereof, comprising Stage 1, Stage 2 and Stage 3, wherein Stage 1 comprises:
  (i) reacting a carboxylic acid (for example of formula (III)) with two or more coupling agents to produce an activated compound;
  (ii) reacting the activated compound with an amine having the formula $R^2R^3NH$ or $R^2R^3ND$ to produce an amide (for example of formula (II); and
  (iii) isolating the amide;
  Stage 2 comprises reacting the amide with $LiAlH_4$ and/or $LiAlD_4$; and
  Stage 3 comprises the step of reacting the compound (for example of (I) or (I')) with an acidic reagent suitable for crystallising a pharmaceutically acceptable salt of the compound of formula (I) or (I').

In some embodiments, a ratio of acidic reagent:compound of formula (I) or (I') of ≥1:1 is used. Often, the ratio of acidic reagent:compound of formula (I(')) is 1:1.

Typically, Stage 3 of the method is carried out in a suitable solvent. The skilled person is able to assess which solvents are suitable for Stage 3. Examples of suitable solvents include ethanol, IPA, iPrOAc and MeCN. In some embodiments, Stage 3 is carried out in ethanol.

Stage 3 of the method of the invention is carried out at a suitable temperature and the skilled person is able to assess which temperatures are suitable for these steps.

In some embodiments, Stage 3 of the method comprises contacting a compound of formula (I) (or (I') and an acidic reagent to produce a first composition. Often, the contacting of Stage 3 is carried out at temperatures of 70 to 100° C., for example 70 to 90° C. or 70 to 80° C. In some embodiments, the contacting of Stage 3 is carried out at temperatures of about 75° C.

In some embodiments, Stage 3 further comprises isolating the pharmaceutically acceptable salt of formula (I) or (I'). The skilled person is aware of techniques in the art suitable for isolation of such a compound. For example, where the compound is dissolved within a suspension, it may be separated from some of the other components of the suspension via filtration, such as hot filtration. The pharmaceutically acceptable salt of formula (I) or (I') may precipitate from the filtrate. The skilled person is aware of methods to encourage precipitation of a compound from a solution, such as cooling the solution, concentrating the solution and/or adding into the solution a crystalline form of the compound to encourage nucleation and the growth of further crystals of the compound from the solution (i.e. seeding). The pharmaceutically acceptable salt of formula (I) or (I') may be recrystallized. The skilled person is aware of techniques that are suitable for recrystallisation of a pharmaceutically acceptable salt of formula (I) or (I') the examples of recrystallisation techniques described with respect to recrystallisation of the inmates resultant from Stage 2 apply mutatis mutandis to recrystallisation of a pharmaceutically acceptable salt of formula (I) or (I').

In more specific embodiments, Stage 3 of the method of the invention comprises the steps of:
i. adding to a fifth vessel at least one equivalent of an acidic reagent suitable for crystallising a pharmaceutically acceptable salt of a compound of formula (I) or (I'),
ii. dissolving a compound of formula (I) or (I') as a freebase in between 5 and 20 volumes of a solvent such as a solvent selected from ethanol, IPA, iPrOAc and MeCN and adding the solution to the fifth reaction vessel,
iii. stirring the contents of the fifth vessel at a temperature of above 72° C. (such as 72 to 90° C.),
iv. filtering the contents of the fifth vessel,
v. adding the filtrate to a sixth vessel and cooling the contents to a temperature of 67° C. to 73° C.,
vi. optionally seeding the sixth vessel with a crystalline form of the pharmaceutically acceptable salt of the compound of formula (I) or (I'),
vii. stirring the contents of the sixth vessel at a temperature of 67° C. to 73° C. for at least 30 minutes (such as 30 minutes to 1 hour),
viii. cooling the contents of the sixth vessel to a temperature of −5° C. to 5° C. at a rate of 2 to 8° C. per hour, and
ix. filtering the contents of the sixth vessel to produce a filter cake comprising a pharmaceutically acceptable salt of the compound of formula (I) or (I').

In some embodiments, the solvent of step ii. is ethanol. In some embodiments, the rate of cooling in step viii. is 5° C. per hour.

P. H. Stahl and C. G. Wermuth provide an overview of pharmaceutical salts and the acids comprised therein in *Handbook of Pharmaceutical Salts: Properties, Selection and Use*, Weinheim/Zürich: Wiley-VCH/VHCA, 2002. The acids described in this review are suitable acidic reagents in order to provide pharmaceutically acceptable salts of or for use in accordance with the various aspects of the present invention.

In some embodiments, the acidic reagent is any one selected from the group consisting of fumaric acid, tartaric acid, citric acid, hydrochloric acid, acetic acid, lactic acid, gluconic acid, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, adipic acid, ascorbic acid, aspartic acid, benzenesulfonic acid, benzoic acid, camphoric acid, camphor-10-sulfonic acid, decanoic acid, hexanoic acid, octanoic acid, carbonic acid, cinnamic acid, cyclamic acid, dodecylsulfuric acid, ethane-1,2-disulfonic acid, ethanesulfonic acid, formic acid, galactaric acid, gentisic acid, glucoheptonic acid, glucuronic acid, glutamic acid, glutaric acid, glycerophosphoric acid, glycolic acid, hippuric acid, hydrobromic acid, isobutyric acid, lactobionic acid, lauric acid, maleic acid, malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (—L), salicylic acid, sebacic acid, stearic acid, succinic acid, sulfuric acid, thiocyanic acid, toluenesulfonic acid and undecylenic acid.

Often, the acidic reagent is any one selected from fumaric acid, tartaric acid, citric acid and hydrochloric acid. In particular embodiments, the acidic reagent is fumaric acid.

The amides resultant from Stage 2 are produced on reacting a starting carboxylic acid with two or more coupling agents to produce an activated compound, and reacting the activated compound with an amine having the formula $R^2R^3NH$ or $R^2R^3ND$. For the avoidance of doubt, the $R^2$ and $R^3$ groups of the amides resultant from Stage 1 and compounds of formula (I) or (I') resultant from Stage 2 (and Stage 3) are derived from the $R^2$ and $R^3$ groups of the amine of formula $R^2R^3NH$.

The compound of formula (I') is produced on reacting the compound of formula (II) with $LiAlH_4$ and/or $LiAlD_4$. Without wishing to be bound by theory, the hydride or deuteride ions provided by $LiAlH_4$ and/or $LiAlD_4$ bind to the carbon atom of the carbonyl of formula (II), resulting in the formation of the compound of formula (I'). For the avoidance of doubt, the $^3H$ groups in formulae ((I) and (I') are derived from the hydride or deuteride ions provided by $LiAlH_4$ and/or $LiAlD_4$.

In some embodiments, at least one $^3H$ is deuterium, i.e. the compound of formula (I') is produced on reacting the compound of formula (II) with $LiAlD_4$ or a mixture of $LiAlD_4$ and $LiAlH_4$.

The method of the seventh aspect of the present invention is particularly useful in allowing access to therapeutically useful α-deuterated compounds (i.e. in which there is a greater than natural preponderance of deuterium at the alpha position in addition to in a methyl group ($R^2$ and/or $R^3$), as the method employs significantly less $LiAlD_4$ than related syntheses known in the art as the method substitutes deuterium at the alpha position but not the beta position. $LiAlD_4$ is among the most expensive and difficult to manufacture reagents in this synthesis. Moreover, optimised methods of the present invention reduce $LiAlH_4$ and/or $LiAlD_4$ requirements, for example from 2 equivalents to 0.9 equivalents which increases economic efficiency in manufacturing deuterated compounds of formula (I) and/or (I'). In view of this, compounds of formula (I') and (I') are cheaper to make, via the methods of the present invention, than other related deuterated compounds, which are typically deuterated at both the alpha and beta position.

As described above, the method of the seventh aspect invention is suitable for the production of high purity compounds of formula (I) and (I'). In some embodiments, the compound of formula (I) or (I'), or a pharmaceutically acceptable salt thereof, is produced at a purity of between 99% and 100% by HPLC, such as a purity of between 99.5% and 100% by HPLC. In some embodiments, the compound of formula (I) or (I'), or a pharmaceutically acceptable salt thereof, is produced at a purity of between 99.9% and 100% by HPLC, such as a purity of between 99.95% and 100% by HPLC.

The chemistry described in connection with the seventh aspect of the invention and Scheme 2 details chemistry that may be practised to synthesise, efficiently, pre-GMP and GMP batches of DMT-based drug substances, including compounds of formula (I). In particular, the coupling agents HOBt and EDC·HCl may be employed to increase the yield of step 1 from less than 70% to greater than 90%. This enables efficient scaling of drug substance batches under GMP standards with overall yield of 65% and above.

A series of DMT-based drug substances, each selectively enriched with deuterium in a GMP-compatible route, some in accordance with formula (I) and others nevertheless of use in the present invention (for instance in its third aspect), were prepared using modified versions of Scheme 2 as follows (with the labelling with reference to formula (I):

| $R^2, R^3$ | $C(^2H)_2$ | Mwt | Modification(s) to Scheme 2* |
|---|---|---|---|
| $(CH_3)_2$ | $CH_2$ | 188.3 | None |
| $(CH_3)_2$ | $C(H)D$ | 189.3 | Stage 2.1:1:1 $LiAlH_4$:$LiAlD_4$ (0.9 equivalents of each) in THF |
| $(CH_3)_2$ | $CD_2$ | 190.3 | Stage 2.1: $LiAlD_4$ (0.9 equivalents) in THF |
| $(CD_3)_2$ | $CH_2$ | 194.3 | Step 1.3: $ND(CD_3)_2$ ... DCI (1.5 equivalents) with DIPEA (4 equivalents) |
| $(CD_3)_2$ | $C(H)D$ | 195.3 | Stage 1.3: $ND(CD_3)_2$ ... DCI (1.5 equivalents) with DIPEA (4 equivalents) Step 2.1:1:1 $LiAlH_4$:$LiAlD_4$ (0.9 equivalents of each) in THF |
| $(CD_3)_2$ | $CD_2$ | 196.3 | Stage 1.3: $ND(CD_3)_2$ ... DCI (1.5 equivalents) with DIPEA (4 equivalents); Stage 2.1: $LiAlD_4$ (0.9 equivalents) in THF |

*and thus the synthesis of (undeuterated) DMT, described in the experimental section below Analogously, the GMP-compatible chemistry of Scheme 2 was used to make a similar series of 5-OMeDMT-based drug substances (see Scheme 4), each selectively enriched with deuterium, some in accordance with formula (I) and others nevertheless of use in the present invention (for instance in its third aspect).

Scheme 4. GMP-compatible route to 5-OMeDMT-based drug substances

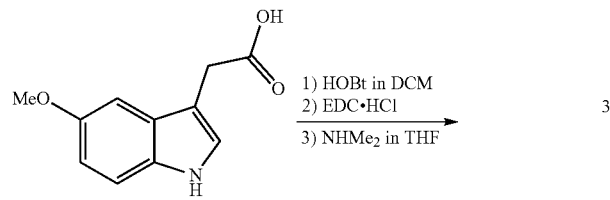

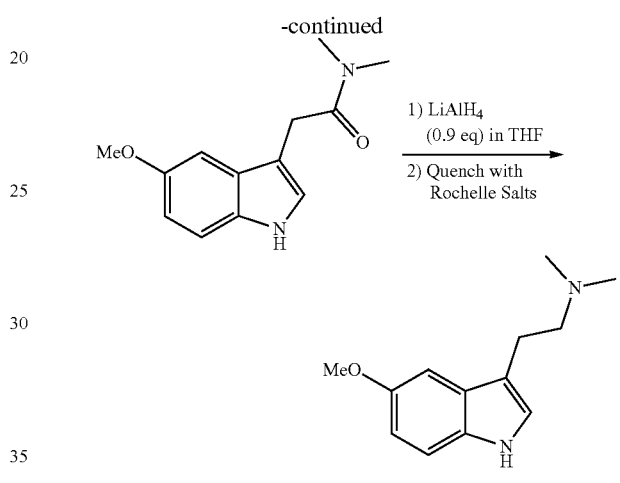

The compounds are described in the table below with the labelling again with reference to formula (I) (in all compounds described below, n=1 and $R^1$=5-OMe):

| $R^2, R^3$ | $C(^2H)_2$ | Mwt | Modification(s) to Scheme 4* |
|---|---|---|---|
| $(CH_3)_2$ | $CH_2$ | 218.3 | None |
| $(CH_3)_2$ | $C(H)D$ | 219.3 | Stage 2.1:1:1 $LiAlH_4$:$LiAlD_4$ (0.9 equivalents of each) in THF |
| $(CH_3)_2$ | $CD_2$ | 220.3 | Stage 2.1: $LiAlD_4$ (0.9 equivalents) in THF |
| $(CD_3)_2$ | $CH_2$ | 224.3 | Stage 1.3: $ND(CD_3)_2$ ... DCI (1.5 equivalents) with DIPEA (4 equivalents) |
| $(CD_3)_2$ | $C(H)D$ | 225.3 | Stage 1.3: $ND(CD_3)_2$ ... DCI (1.5 equivalents) with DIPEA (4 equivalents) Step 2.1:1:1 $LiAlH_4$:$LiAlD_4$ (0.9 equivalents of each) in THF |
| $(CD_3)_2$ | $CD_2$ | 226.3 | Stage 1.3: $ND(CD_3)_2$ ... DCI (1.5 equivalents) with DIPEA (4 equivalents) Stage 2.1: $LiAlD_4$ (0.9 equivalents) in THF |

*and thus the synthesis of (undeuterated) 5-OMeDMT, described in the experimental section below In accordance with the third aspect of the invention is provided a composition comprising a first compound, which is a compound or pharmaceutically acceptable salt thereof as defined in accordance with the first aspect of the invention, and a second compound, which is either (i) a compound or pharmaceutically acceptable salt thereof as defined in accordance with the first aspect of the invention, but which differs from the first compound through the identity of $^3$H and/or the identity of $R^3$; or (ii) a compound or pharmaceutically acceptable salt thereof as defined in accordance with the first aspect of the invention, except that each $^x$H and $^y$H represent hydrogen.

Typically the second compound differs from the first compound only through the identity of $^y$H and/or the identity of $R^3$; and/or $^x$H and $^y$H representing hydrogen.

For example, the first and second compounds may differ through the identity of $^y$H, and in embodiments only through the identity of $^y$H. As is described in WO 2020/245133 A1 (Small Pharma Ltd), a quantifiable relationship exists between the extent of α-deuteration, and by proxy the H:D ratio of input reducing agent in the synthetic methods disclosed therein, and the effect on potentiation of the metabolic half-life of DMT. Such technical information may be used to prepare compositions comprising pluralities of compounds of formula (I) described herein, in which the compounds or salts differ from each other only through the identity of $^y$H.

It will be understood from the discussion above about synthetic methodology that this may readily be achieved, in a controllable way, by using mixtures of lithium aluminium hydride and lithium aluminium deuteride when reducing a precursor amide, the carbonyl group of which is converted to the C($^y$H)$_2$ portion of formulae (I) and (I'). For example, mixtures of compounds comprising controllable proportions of compounds of formula (I), in which n=0, which differ only by virtue of α-mono- and/or α,α-di-deuteration (i.e. that differ only through the identity of $^y$H) may, if desired, be prepared by reducing 2-(3-indolyl)-acetamide having the desired $R^2$ and $R^3$ groups with a desired ratio of lithium aluminium hydride and lithium aluminium deuteride.

Alternatively or additionally, compounds (or pharmaceutically acceptable salts thereof) in the composition of the third aspect of the invention may differ from each other through the identity of $R^3$, for example only through the identity of $R^3$ and/or only through the identity of $^y$H. Varying $R^3$ may be achieved either where a compound is present in the composition in which $R^2$ is the same as $R^3$, in which case this is typically but not necessarily CD$_3$; and another compound is present in which $R^3$ is H.

The binding of dimethylamino-containing compounds of formula (I), that is to say compounds of formula (I) in which $R^3$ is not H, to serotonin receptors within the body is expected to differ in selectivity and strength to the binding of monomethylamino compounds of formula (I) i.e. in which $R^3$ is H. Varying the relative amounts of dimethylamino- and monomethylamino-containing compounds (in at least one of which the proportion of deuterium in a N-methyl group is greater than its natural isotopic abundance and hydrogen) within compositions of the invention is expected to allow modulation the pharmacodynamics and consequently the therapeutic effect of the compositions. This offers a further element of control over the metabolism of compounds of formula (I).

Alternatively or additionally (to the composition comprising compounds of formula (I) that differ through the identity of $^y$H and/or $R^3$ that is), compositions of the third aspect of the invention may comprise a compound or pharmaceutically acceptable salt thereof as defined in accordance with the first aspect of the invention, except for each $^x$H and $^y$H representing hydrogen, in other words an analogue of a compound of formula (I) or pharmaceutically acceptable salt thereof without deuterium enrichment. As is set out in detail WO 2020/245133 A1 (Small Pharma Ltd), supra, mixtures of DMT and alpha- and/or beta-deuterated analogues thereof are described, together with the clinical usefulness. In the same way, mixtures of compounds of formula (I) and on deuterated analogues thereof may be used to modify, controllably, the pharmacokinetic profile of compounds of formula (I described herein), thereby permitting more flexible therapeutic application.

Combining different compounds in these ways, whereby to provide compositions in accordance with the third aspect of the invention, provides additional variables, additional to increasing the proportion of deuterium atoms in the methyl groups of DMT or methyl group of NMT and their $R^1$-substituted derivatives that is, through which the pharmacodynamics of the parent undeuterated compounds corresponding to those of formula (I) may be modified.

In particular, varying the relative amounts of the compounds within the compositions of the invention may be expected to modulate the pharmacodynamics and consequently the therapeutic effect of the compositions. Where these comprise compounds of formula (I) in which $R^3$ is H, for example, greater concentrations of these compounds may be susceptible to administration, since greater quantities of monomethyltryptamine compounds (to their dimethyltryptamine counterparts) are generally tolerated in vivo. The relative amounts of different compounds within the compositions of the invention may be determined by a medical practitioner, based, in part on the metabolic profile of the patient to whom the composition is intended to be administered. For example, relatively greater amounts of compounds of formula (I) in which $R^3$ is H may be more suitable for a patient with a higher metabolism.

In some embodiments, the composition of the third aspect of the invention comprises compounds of formula (I) in each of which one $^y$H is H and the other is D. In some embodiments, the composition comprises compounds of formula (I) in each of which each $^y$H is H. Sometimes, the composition comprises compounds of formula (I) in each of which each $^y$H is D.

For the avoidance of doubt, the above-mentioned embodiments do not exclude the presence of further compounds of formula (I) or undeuterated analogues thereof.

In particular embodiments, the composition of the third aspect of the invention comprises two or three compounds of formula (I), which differ from one another only by the definition of $^y$H, i.e. providing a population of compounds of formula (I) in which the C($^y$H)$_2$ moiety is CH$_2$, CD$_2$ or CH. In particular embodiments of these, NR$^2$R$^3$ is N(CD$_3$)$_2$ or N(CH$_3$)(CD$_3$), often N(CD$_3$)$_2$.

Compositions and of the invention may be quantified, at least partially, by their mean molecular weight. As used herein, mean molecular weight means the weighted average of molecular weights of a compound or composition (for example a composition comprising two or compounds of formula (I) differing only from one another by the extent of deuteration), as measured by an appropriate mass spectroscopic technique, for example LC-MS SIM (selected-ion monitoring). In some embodiments, the mean molecular weight is the weighted average.

It will be understood that it will be possible to use mean molecular weights to characterise useful compounds and compositions of the invention obtainable through the teachings herein, in particular by adjusting the relative proportions of lithium aluminium hydride and lithium aluminium deuteride in the reductions exemplified. It will be further understood that the greater the extent of deuteration, the higher the mean molecular weight of the composition.

In some embodiments, the composition consists essentially of compounds of formula (I), optionally with undeuterated analogues thereof. This means that the composition does not comprise material quantities of other pharmaceutically active compounds, including other dimethyltryptamine compounds. In other specific embodiments, the composition consists essentially of compounds of formula (I). In other words, and alternatively put, the compositions according to these specific embodiments constitute a drug substance comprising a biologically active ingredient consisting essentially of a mixture of compounds of formula (I).

According to particular embodiments, compositions of the invention, and used and for use in accordance with the relevant aspects of the invention are absent material (e.g. detectable quantities of dimethyltryptamine), in particular where one or both of $R^2$ and $R^3$ are $CD_3$.

In some embodiments, the compositions of the invention have an oxygen content of less than 2 ppm, such as between 0.1 ppm and 2 ppm. The skilled person is able to determine the oxygen content of the formulation using any technique known in the art to be suitable, such as using a dissolved oxygen meter (e.g. a Jenway 970 Enterprise Dissolved Oxygen Meter, available from Keison Products: http://www.keison.co.uk/products/jenway/970.pdf. Compositions of the invention having an oxygen content of less than 2 ppm are particularly advantageous for preparing dosage forms for administration via the oral or nasal cavities, as the reduced oxygen content ameliorates formation of malodourous impurities and/or degradation products from compounds of formula (I).

The composition may be stored in any suitable container. In some embodiments, to ameliorate degradation of the composition, compositions of the invention are stored in a container adapted to prevent penetration of ultraviolet light, such as an amber glass vial. In others, the container within which the composition is stored is not so adapted (and may be, for example, made of clear glass) with protection against ultraviolet light, if desired, provided by secondary packaging (for example packaging within which the receptacle containing the formulation may be placed).

To ameliorate degradation of the composition, it may be desirable to minimise the total oxygen content within the container in which the composition is stored, the oxygen within the container equilibrating between the composition and the headspace (if any) within the container. Accordingly, it may be desirable to store the composition under an inert atmosphere for example by purging the headspace to reduce its oxygen content from about 20% typically found in air, to less than, for example, 0.5%. Often, the container is airtight and the composition is stored under an inert atmosphere, such as under nitrogen or argon, typically nitrogen. The composition may be stored at room temperature, e.g. at about 20 to about 30° C. (typically about 20° C.) or at cooler temperatures, for example at about 2 to about 8° C. Alternatively, to ameliorate degradation of the composition further, it may be stored at temperatures lower than room temperature, such as in a refrigerator or freezer.

As described above, the invention provides in its fourth aspect a pharmaceutical composition comprising a compound of formula (I), either defined in accordance with the first aspect of the invention or in accordance with the second aspect of the invention, or a composition in accordance with the third aspect of the invention, in combination with a pharmaceutically acceptable excipient.

Examples of pharmaceutically acceptable excipients that may be comprised within the pharmaceutical composition of the invention include but are not limited to those described in Gennaro et al., Remmington: *The Science and Practice of Pharmacy*, 20$^{th}$ Edition, Lippincott, Williams and Wilkins, 2000 (specifically part 5: pharmaceutical manufacturing). Suitable pharmaceutically acceptable excipients are also described in the Handbook of Pharmaceutical Excipients, 2$^{nd}$ Edition; Editors A. Wade and P. J. Weller, American Pharmaceutical Association, Washington, The Pharmaceutical Press, London, 1994. M. F. Powell, T. Nguyen and L. Baloian provide a review of excipients suitable for parenteral administration (administration other than by the mouth or alimentary canal) in PDA J. Pharm. Sci. Technol., 52, 238-311 (1998). Compositions include those suitable for oral, nasal, topical (including buccal, sublingual and transdermal), parenteral (including subcutaneous, intravenous and intramuscular) or rectal administration.

By means of pharmaceutically suitable liquids, the compositions of the invention can be prepared in the form of a solution, suspension, emulsion, or as a spray. Aqueous suspensions, isotonic saline solutions and sterile injectable solutions may be used, containing pharmaceutically acceptable dispersing agents and/or wetting agents, such as propylene glycol or butylene glycol.

The invention also provides a composition of the invention, in combination with packaging material suitable for the composition, the packaging material including instructions for the use of the composition.

According to some embodiments, the pharmaceutical compositions of the invention are suitable for parenteral administration, i.e. suitable for administration other than by the mouth or alimentary canal, for example by inhalation or nasal, topical (including buccal, sublingual and transdermal), subcutaneous, intravenous or intramuscular administration. By being suitable for (i.e. for) parenteral administration means that such compositions are in accordance with Pharmacopeial requirements of sterility, contaminants, and pyrogens (see for example The United States Pharmacopeial Convention, General Requirements/⟨ 1⟩ Injections, page 33). Sometimes, the pharmaceutical compositions contains inhibitors of the growth of microorganisms (e.g. antimicrobial preservatives) and/or anti-oxidants.

Pharmaceutical compositions suitable for injection typically have a pH of about 3 to 9 and an osmolality of about 250 to about 600 mOsm/Kg. pH values above 9 are reported by I. Usach et al. in *Adv. Ther.*, 36, 2986-2996 (2019) to relate to tissue necrosis (death of cells within the tissue), whereas values lower than 3 are reported to cause pain and phlebitis (inflammation of veins). Osmolality values greater than 600 mOsm/Kg are also reported to cause pain.

As is described herein, the compounds and compositions of the invention are anticipated to have greater oral bioavailability than a compound corresponding to one of formula (I) but without the deuterium enrichment in a methyl group corresponding to $R^2$ or $R^3$. According to particular embodiments, therefore, the pharmaceutical composition of the invention is in the form of an oral dosage form.

By "oral dosage form" is meant a particular configuration (such as a tablet or capsule, for example) comprising a particular dose of the compound or composition, wherein the configuration is suitable for oral administration. The oral dosage form may be a solid dosage form, such as a tablet, capsule, sachet, powder or granule, or a liquid or semi-solid oral dosage form such as a syrup, solution, ampoule, or dispersion. Typically, the oral dosage form is a solid dosage form, often a tablet or a capsule.

According to still further embodiments, the pharmaceutical compositions of the invention are presented in a form suitable for inhalation. Inhalable formulations preferably comprise the compound of compounds of formula (I) in freebase form.

For the avoidance of doubt, an inhalable formulation is capable of becoming airborne and entering the lungs of a patient through the action of the patient breathing in. In other words, inhalable formulations are suitable for pulmonary administration. The inhalable formulation may be inhaled in the form of a vapour, aerosol or gas. Often, the inhalable formulation is inhaled in the form of a vapour or aerosol.

By "freebase" is meant that the amine within the compound of formula (I) or undeuterated analogues thereof (for example which may be present in compositions of the invention in addition to compounds of formula (I), as discussed above) are in their unprotonated form, as opposed to the conjugate acid (protonated) form of the amine. Accordingly, salts of the compounds of formula (I) or undeuterated analogues thereof are excluded from the scope of the freebase. For the avoidance of doubt, zwitterions comprising a protonated form of the amine and a negatively charged substituent bound to the DMT (such as in the zwitterionic form of psilocybin) are excluded from the scope of the freebase.

Pharmaceutical compositions suitable for inhalation comprise a solvent in which the freebase is at least partially soluble. The solvent is typically a liquid at ambient temperature and pressure (in particular at about 20° C. and about 1 bar). In more particular embodiments, the solvent is capable of forming a vapour or aerosol comprising the freebase on the application of heat, for example the solvent may be suitable for use in an electronic vaping device (EVD). EVDs typically include a power supply section and a cartridge. The power supply section often comprises a power source such as a battery, and the cartridge often comprises a heater and a reservoir capable of holding an inhalable formulation. The heater is typically contacted with the inhalable formulation (e.g. by a wick), and is typically configured to heat the inhalable formulation to generate a vapour or aerosol.

In some embodiments, the solvent is volatile (has a boiling point of ≤100° C., such as 50 to 100° C.). Such solvents may be capable of evaporation under the airflow of a vaporiser (such as a Volcano Medic Vaporizer) at temperatures of 30 to 70° C., e.g. 55° C. Evaporation of the solvent leaves a residue of freebase, which may then be vapourised into a vapour or aerosol under the airflow of a vapouriser at higher temperatures (e.g. at temperatures of about 150 to 250° C., such as 210° C.), and inhaled.

In some embodiments, the solvent is any one or a combination of two or more selected from the group consisting of propylene glycol (propane-1,2-diol), glycerine, polyethylene glycol, water, propanediol (propane-1,3-diol), butylene glycol (butane-1,3-diol), butane-2,3,-diol, butane-1,2-diol, ethanol and triacetin.

In some embodiments, the solvent is selected from propylene glycol, glycerine and polyethylene glycol, or a mixture thereof. Typically, the solvent is a mixture of propylene glycol and glycerine in a ratio of from about 50:50 (propylene glycol:glycerine) to about 10:90 by weight, such as about 50:50 to about 20:80 or about 50:50 to about 30:70 by weight. In some embodiments, the solvent is a mixture of propylene glycol and glycerine in a ratio of from about 50:50 to about 30:70 by weight.

Often, the glycerine is vegetable glycerine, i.e. glycerine derived from plant oils.

Pharmaceutical compositions suitable for inhalation or nasal administration often comprise a taste-masking agent. The purpose of the taste-masking agent is to make the taste or smell of the formulation more appealing to the patient. In some embodiments, the pharmaceutically acceptable excipient comprises a taste-masking agent. When the pharmaceutically acceptable excipient comprises a solvent and a taste-masking agent, the taste-masking agent is typically at least partially soluble in the solvent and the solvent is often able to form a vapour or aerosol comprising the freebase and the taste-masking agent on the application of heat. Often, the taste-masking agent is suitable for vaporisation into a vapour or aerosol under the airflow of a vapouriser (e.g. at temperatures of about 150 to 250° C., such as 210° C.). The taste-masking agent is typically a liquid or a solid at ambient temperature and pressure. It is advantageous that the taste-masking agent has no adverse effect on the bioavailability of the freebase, e.g. it is advantageous that the freebase is stable when stored in the presence of the taste-masking agent.

In some embodiments, the taste-masking agent is any one or a combination of two or more selected from the group consisting of flavourings, glucose, fructose, sorbitol, mannitol, honey, saccharin, sucrose, xylitol, erythritol, maltitol, sucralose, neotame, trehalose and tagatose. In some embodiments, flavourings are menthol, vanilla, wintergreen, peppermint, maple, apricot, peach, raspberry, walnut, butterscotch, wild cherry, chocolate, anise, citrus such as orange or lemon, or liquorice flavourings.

Examples of further pharmaceutically acceptable excipients that may be comprised within the compositions suitable for inhalation or otherwise include but are not limited to those described in Gennaro et. al., Remmington: *The Science and Practice of Pharmacy*, $20^{th}$ Edition, Lippincott, Williams and Wilkins, 2000 (specifically part 5: pharmaceutical manufacturing). Suitable pharmaceutical excipients are also described in the Handbook of Pharmaceutical Excipients, $2^{nd}$ Edition; Editors A. Wade and P. J. Weller, American Pharmaceutical Association, Washington, The Pharmaceutical Press, London, 1994. M. F. Powell, T. Nguyen and L. Baloian provide a review of excipients suitable for parenteral administration in PDA J. Pharm. Sci. Technol., 52, 238-311 (1998). All soluble excipients listed in this review article are suitable excipients for use in inhalable formulations.

By means of pharmaceutically suitable liquids, the inhalable formulations can be prepared in the form of a solution, suspension, emulsion, or as a spray. Aqueous suspensions, isotonic saline solutions and sterile injectable solutions may be used, containing pharmaceutically acceptable dispersing agents and/or wetting agents, such as propylene glycol or butylene glycol.

As described in detail herein, the invention is of therapeutic utility. In some embodiments, the therapy is psychedelic-assisted psychotherapy, i.e. the therapy associated with the first aspect of the invention is treatment of a mental disorder by psychological means, which are enhanced by one or more protocols in which a patient is subjected to a psychedelic experience induced by administration of the compound of formula (I).

In its fifth aspect, the invention provides a compound as defined in the first aspect, of the second aspect or composition of the third or fourth aspects for use in a method of treating a psychiatric or neurological disorder in a patient.

In another aspect, the invention provides use of a compound as defined in the first aspect, of the second aspect or a composition of the third aspect for the manufacture of a medicament. In some embodiments of this aspect, the medicament is for use in a method of treating a psychiatric or neurological disorder in a patient, including those disorders described immediately hereinafter.

In some embodiments, the psychiatric or neurological disorder is selected from (i) an obsessive compulsive disorder, (ii) a depressive disorder, (iii) a schizophrenia disorder, (iv) a schizotypal disorder, (v) an anxiety disorder, (vi) substance abuse, and (vii) an avolition disorder. Often, the psychiatric or neurological disorder is selected from the group consisting of (i) an obsessive compulsive disorder, (ii) a depressive disorder, (iii) an anxiety disorder, (iv) substance abuse, and (v) an avolition disorder.

In some embodiments, the disorder is selected from the group consisting of major depressive disorder, treatment resistant major depressive disorder, post-partum depression, an obsessive compulsive disorder and an eating disorder such as a compulsive eating disorder.

In some embodiments, the psychiatric or neurological disorder is major depressive disorder. In some embodiments, the psychiatric or neurological disorder is treatment resistant depression.

In some embodiments, the therapy or method of treatment comprises parenteral administration, such as inhalation or pulmonary administration of the formulation.

For the avoidance of doubt, embodiments related to fifth aspect of the invention apply mutatis mutandis to the method of treatment of the sixth aspect of the invention. For example, the method may be to treat a disorder selected from the group consisting of (i) an obsessive compulsive disorder, (ii) a depressive disorder, (iii) an anxiety disorder, (iv) substance abuse, and (v) an avolition disorder.

In order to treat the disorder, an effective amount of a compound of formula (I is administered, i.e. an amount that is sufficient to reduce or halt the rate of progression of the disorder, or to ameliorate or cure the disorder and thus produce the desired therapeutic or inhibitory effect.

Each and every reference referred to herein is hereby incorporated by reference in its entirety, as if the entire content of each reference was set forth herein in its entirety.

The invention may be further understood with reference to the examples that follow.

EXAMPLES

Summary

A series of in vitro drug metabolism and pharmacokinetics (DMPK) experiments (Table 1) on N,N-dimethyltryptamine (DMT, SPL026), six different α,α,-bis-deuterium-N,N-dimethyltryptamine analogue blends ($D_2$DMT, SPL028i-SPL028vi), N,N-hexadeuterio-dimethyltryptamine ($D_6$DMT, SPL028vii) and α,α,bis-deuterio-N,N-hexadeuterio-dimethyltryptamine ($D_8$DMT, SPL028viii) were performed on human and animal tissue to investigate the metabolic profile and stability for each isotopic mixture (Table 2).

Comparisons of drug clearance in human liver hepatocyte and mitochondrial fractions indicate that deuterium enrichment of the α-carbon provides a rate limiting step in MAO-mediated oxidative deamination of DMT analogues, which progressively increases with level of α-deuteration.

CYP phenotyping indicated that SPL026 and two $D_2$-deuterated blends (SPL028i, SPL028ii) are substrates for the CYP2D6 and CYP2C19 enzymes. This result indicates an additional role of CYP-mediated metabolism of DMT analogues, which could possibly contribute to the formation of secondary metabolites via the Noxidative pathway in vivo.

Deuterium substitution of DMT's methyl groups demonstrated an additional DKIE which may be attributed to disruption of alternative metabolic pathways such as demethylation and N-oxidation, or via a secondary DKIE mechanism. Also notable is the absence of lower deuterated species $D_0$ to $D_5$ in SPL028vii and SPL028viii (see Table 2). This is advantageous for analytical method development and validation and CMC aspects of drug product development of compounds and compositions of the present invention.

Experimental

A series of in vitro experiments (see Table 1 below) were conducted on a range of deuterium-enriched DMT compounds, SPL028i-SPL028viii, in order to investigate the DKIE in human and animal tissue as a proxy of in vivo clearance.

TABLE 1

Summary of in vitro DMPK experiments with SPL026 and SPL028 deuterated analogues

| Study Description | Compounds tested |
|---|---|
| Contribution of MAO in vitro human hepatic intrinsic clearance | SPL026, 6 × SPL028 ($D_2$) |
| In vitro mouse hepatocytic intrinsic clearance | SPL026, 6 × SPL028 ($D_2$) |
| In vitro human hepatocytic intrinsic clearance | SPL026, SPL028i ($D_2$), SPL028ii ($D_2$), SPL028vii (D6), SPL028viii ($D_8$) |
| Contribution of MAO-A and MAO-B in vitro human liver mitochondrial fraction intrinsic clearance | SPL026 |
| In vitro human mitochondrial fraction intrinsic clearance | SPL026, SPL028i, SPL028iii, SPL028viii |
| In vitro human mitochondrial fraction intrinsic clearance | SPL026, SPL028i, SPL028ii, SPL028iii, SPL028vii, SPL028viii |
| CYP phenotyping against 8 human CYPs | SPL026, SPL028i ($D_2$), SPL028ii ($D_2$) |

TABLE 2

SPL026 and SPL028 deuterated analogues used in in vitro studies, detailing relative ratio of deuteration and calculated molecular weight for each compound

| Cpd Name | Weighted MW (g/mol) | $D_0$ | $D_1$ | $D_2$ | $D_4$ | $D_5$ | $D_6$ | $D_7$ | $D_8$ |
|---|---|---|---|---|---|---|---|---|---|
| SPL026 | 188.27 | 100 | 0 | 0 | 0 | 0 | 0 | 0 | 0 |
| SPL028i | 190.2398 | 0.70% | 2.70% | 96.60% | 0 | 0 | 0 | 0 | 0 |
| SPL028ii | 189.1915 | 30.00% | 48.30% | 21.70% | 0 | 0 | 0 | 0 | 0 |
| SPL028iii | 189.6685 | 16.50% | 46.80% | 36.80% | 0 | 0 | 0 | 0 | 0 |
| SPL028iv | 189.6764 | 9.30% | 41.50% | 49.20% | 0 | 0 | 0 | 0 | 0 |
| SPL028v | 188.9098 | 47.50% | 41.30% | 11.20% | 0 | 0 | 0 | 0 | 0 |
| SPL028vi | 188.9613 | 57.40% | 35.30% | 7.40% | 0 | 0 | 0 | 0 | 0 |
| SPL028vii | 194.308 | 0.00% | 0 | 0 | 0.01% | 1.20% | 98.80% | 0 | 0 |
| SPL028viii | 196.318 | 0.00% | 0 | 0 | 0 | 0 | 0.10% | 3.20% | 96.70% |

Chemistry

Synthesis of DMT (SPL026)

Stage 1: Coupling of indole-3-acetic acid and dimethylamine

To a 5 L vessel under $N_2$ was charged indole-3-acetic acid (257.0 g, 1.467 mol), Hydroxybenzotriazole (HOBt) (~20% wet) (297.3 g, 1.760 mol) and dichloromethane (DCM) (2313 mL) to give a milky white suspension. Ethylcarbodiimide hydrochloride (EDC·HCl) (337.5 g, 1.760 mol) was then charged portion-wise over 5 minutes at 16-22° C. The reaction mixture was stirred for 2 hours at ambient temperature before 2 M dimethylamine in tetrahydrofuran (THF) (1100 mL, 2.200 mol) was charged dropwise over 20 minutes at 20-30° C. The resultant solution was stirred at ambient temperature for 1 hour where HPLC indicated 1.1% indole-3-acetic acid and 98.1% stage 1. The reaction mixture was then charged with 10% $K_2CO_3$ (1285 mL) and stirred for 5 minutes. The layers were separated, and the upper aqueous layer extracted with DCM (643 mL×2). The organic extracts were combined and washed with saturated brine (643 mL). The organic extracts were then dried over $MgSO_4$, filtered and concentrated in vacuo at 45° C. This provided 303.1 g of crude stage 1 as an off-white sticky solid. The crude material was then subjected to a slurry in methyl-t-butyl ether (TBME) (2570 mL) at 50° C. for 2 hours before being cooled to ambient temperature, filtered and washed with TBME (514 mL×2). The filter-cake was then dried in vacuo at 50° C. to afford stage 1 266.2 g (yield=90%) as an off-white solid in a purity of 98.5% by HPLC and >95% by NMR.

Stage 2: Preparation of DMT

To a 5 L vessel under $N_2$ was charged stage 1 (272.5 g, 1.347 mol) and THF (1363 mL) to give an off-white suspension. 2.4 M $LiAlH_4$ in THF (505.3 mL, 1.213 mol) was then charged dropwise over 35 minutes at 20-56° C. to give an amber solution. The solution was heated to 60° C. for 2 hours where HPLC indicated stage 1 ND, stage 2 92.5%, Impurity 1 2.6%, Impurity 2 1.9%. The complete reaction mixture was cooled to ambient temperature and then charged to a solution of 25% Rochelle's salts (aq.) (2725 mL) dropwise over 30 minutes at 20-30° C. The resultant milky white suspension was allowed to stir at 20-25° C. for 1 hour after which the layers were separated and the upper organic layer washed with saturated brine (681 mL). The organic layer was then dried over $MgSO_4$, filtered and concentrated in vacuo at 45° C. The resultant crude oil was subjected to an azeotrope from ethanol (545 mL×2). This provided 234.6 g (yield=92%) of stage 2 in a purity of 95.0% by HPLC and >95% by NMR.

Stage 3a (i)-(iii): Preparation of Seed Crystals of DMT Fumarate (i) Stage 2 (100 mg) was taken up in 8 volumes of isopropyl acetate and warmed to 50° C. before charging fumaric acid (1 equivalent) as a solution in ethanol. The flask was then allowed to mature at 50° C. for 1 hour before cooling to room temperature and stirring overnight, resulting in a white suspension. The solids were isolated by filtration and dried for 4 hours at 50° C. to provide 161 mg of product (>99% yield). Purity by HPLC was determined to be 99.5% and by NMR to be >95%.

(ii) Substitution of isopropyl acetate for isopropyl alcohol in method (i) afforded a white suspension after stirring overnight. The solids were isolated by filtration and dried for 4 hours at 50° C. to provide 168 mg of product (>99% yield). Purity by HPLC was determined to be 99.8% and by NMR to be >95%.

(iii) Substitution of isopropyl acetate for tetrahydrofuran in method (i) afforded a white suspension after stirring overnight. The solids were isolated by filtration and dried for 4 hours at 50° C. to provide 161 mg of product (>99% yield). Purity by HPLC was determined to be 99.4% and by NMR to be >95%.

Analysis by x-ray powder diffraction, showed the products of each of methods 9i) to (iii) to be the same, which was labelled Pattern A.

Stage 3b: Preparation of DMT Fumarate

To a 5 L flange flask under $N_2$ was charged fumaric acid (152.7 g, 1.315 mol) and Stage 2 (248.2 g, 1.315 mol) as a solution in ethanol (2928 mL). The mixture was heated to 75° C. to give a dark brown solution. The solution was polish filtered into a preheated (80° C.) 5 L jacketed vessel. The solution was then cooled to 70° C. and seeded with Pattern A (0.1 wt %), the seed was allowed to mature for 30 minutes before cooling to 0° C. at a rate of 5° C./hour. After stirring for an additional 4 hours at 0° C., the batch was filtered and washed with cold ethanol (496 mL×2) and then dried at 50° C. overnight. This provided 312.4 g (yield=78%) of Stage 3 in a purity of 99.9% by HPLC and >95% by NMR. XRPD: Pattern A.

Synthesis of 5MeO-DMT

Stage 1: Coupling of 5-methoxyindole-3-acetic Acid and Dimethylamine

To a 100 mL 3-neck flask under $N_2$ was charged 5-methoxyindole-3-acetic acid (3.978 g, 19.385 mmol), HOBt (~20% wet) (3.927 g, 23.261 mmol) and DCM (40 mL). EDC·HCl (4.459 g, 23.261 mmol) was then charged in portions over 15 minutes at <30° C. The reaction mixture was stirred at ambient temperature for 1 hour before being charged with 2 M dimethylamine (14.54 mL, 29.078 mmol) dropwise over 15 minutes at <25° C. After stirring for 1 hour HPLC indicated no starting material (SM, i.e. 5-methoxyindole-3-acetic acid) remained. The reaction mixture was then charged with 10% $K_2CO_3$ (20 mL), stirred for 5 minutes then allowed to separate. The lower aqueous layer was removed and back extracted with DCM (10 mL×2). The organic extracts were combined, washed with saturated brine (10 mL) then dried over $MgSO_4$ and filtered. The filtrate was concentrated in vacuo at 45° C. to provide 3.898 g active (yield=87%) of product in a purity of 95.7% by HPLC.

Stage 2: Preparation of 5MeO-DMT

To a 100 mL 3-neck flask under $N_2$ was charged stage 1 methoxy derivative (3.85 g, 16.586 mmol) and THF (19.25 mL). 2.4 M $LiAlH_4$ in THF (6.22 mL, 14.927 mmol) was then charged dropwise over 30 minutes at <40° C. The reaction mixture was heated to 60° C. for 1 hour where HPLC indicated 0.1% SM (stage 1 methoxy derivative) remained. The reaction mixture was then cooled to ambient temperature and quenched into 25% Rochelle's salts (38.5 mL) dropwise over 30 minutes at <30° C. The resultant suspension was stirred for 1 hour before being allowed to separate. The lower aqueous layer was then removed, and the upper organic layer washed with saturated brine (9.6 mL). The organics were then dried over $MgSO_4$, filtered and concentrated in vacuo before being subjected to an azeotrope from EtOH (10 mL×2). This provided 3.167 g active (yield=88%) of product in a purity of 91.5% by HPLC.

Stage 3: Preparation of 5MeO-DMT Fumarate

To a 50 mL 3-neck flask under $N_2$ was charged fumaric acid (1.675 g, 14.430 mmol) and a solution of stage 2 methoxy derivative (3.15 g, 14.430 mmol) in EtOH (37.8 mL). The mixture was then heated to 75° C. for 1 hour, this did not produce a solution as expected, the mixture was further heated to reflux (78° C.) which still failed to provide a solution. The suspension was therefore cooled to 0-5° C., filtered and washed with EtOH (8 mL×2) before being dried at 50° C. overnight. This provided 3.165 g (yield=65%) of material in a purity of 99.9% by HPLC.

Synthesis of α,α-dideutero-5-Methoxydimethyltryptamine

For stage 1 (coupling of 5-methoxyindole-3-acetic acid and dimethylamine), see above.

Stage 2: Preparation of α,α-dideutero-5-Methoxydimethyltryptamine

To a 100 mL 3-neck flask under $N_2$ was charged stage 1 methoxy derivative (3.85 g, 16.586 mmol) and THF (19.25 mL). 2.4 M $LiAlD_4$ in THF (6.22 mL, 14.927 mmol) was then charged dropwise over 30 minutes at <40° C. The reaction mixture was heated to 60° C. for 1 hour where HPLC indicated 0.1% SM (stage 1 methoxy derivative) remained. The reaction mixture was then cooled to ambient temperature and quenched into 25% Rochelle's salts (38.5 mL) dropwise over 30 minutes at <30° C. The resultant suspension was stirred for 1 hour before being allowed to separate. The lower aqueous layer was then removed, and the upper organic layer washed with saturated brine (9.6 mL). The organics were then dried over $MgSO_4$, filtered and concentrated in vacuo before being subjected to an azeotrope from EtOH (10 mL×2). This provided 3.196 g active (yield=88%) of product in a purity of 91.5% by HPLC.

Stage 3: Preparation of α,α-dideutero-5-Methoxydimethyltryptamine Fumarate

To a 50 mL 3-neck flask under $N_2$ was charged fumaric acid (1.675 g, 14.430 mmol) and a solution of stage 2 methoxy derivative (3.15 g, 14.430 mmol) in EtOH (37.8 mL). The mixture was then heated to 75° C. for 1 hour, this did not produce a solution as expected, the mixture was further heated to reflux (78° C.) which still failed to provide a solution. The suspension was therefore cooled to 0-5° C., filtered and washed with EtOH (8 mL×2) before being dried at 50° C. overnight. This provided 3.165 g (yield=65%) of material in a purity of 99.9% by HPLC.

Synthesis of Deuterated Mixtures of DMT Compounds (SPL028i to SPL028vi)

A modified synthesis at stage 2 using solid $LiAlH_4$/$LiAlD_4$ mixtures was adopted, using 1.8 equivalents of $LiAlH_4$/$LiAlD_4$ versus 0.9 equivalents using the process described above for undeuterated DMT.

Six deuteration reactions were performed.

Representative Synthesis of a Deuterated Mixture (Using 1:1 $LiAlH_4$:$LiAlD_4$) of DMT Compounds To a 250 mL 3-neck flask under $N_2$ was charged $LiAlH_4$ (1.013 g, 26.7 mmol), $LiAlD_4$ (1.120 g, 26.7 mmol) and THF (100 mL). The resultant suspension was stirred for 30 minutes before stage 1 (6 g, 29.666 mmol) was charged portion-wise over 15 minutes at 20-40° C. The reaction mixture was then heated to reflux (66° C.) for 2 hours where HPLC indicated no stage 1 remained. The mixture was cooled to 0° C. and quenched with 25% Rochelle's salts (aq) (120 mL) over 30 minutes at <30° C. The resultant milky suspension was stirred for 1 hour and then allowed to separate. The lower aqueous layer was removed and the upper organic layer washed with saturated brine (30 mL). The organics were then dried over $MgSO_4$, filtered and concentrated in vacuo. This provided 4.3 g of crude material. The crude was then taken up in ethanol (52 mL) and charged with fumaric acid (2.66 g, 22.917 mmol) before heating to 75° C. The resultant solution was allowed to cool to ambient temperature overnight before further cooling to 0-5° C. for 1 hour. The solids were isolated by filtration and washed with cold ethanol (6.5 mL×2). The filter cake was dried at 50° C. overnight to provided 5.7 g (yield=63%) of product in a purity of 99.9% by HPLC and >95% by NMR.

Synthesis of $d_6$-DMT (SPL028vii)

Stage 1

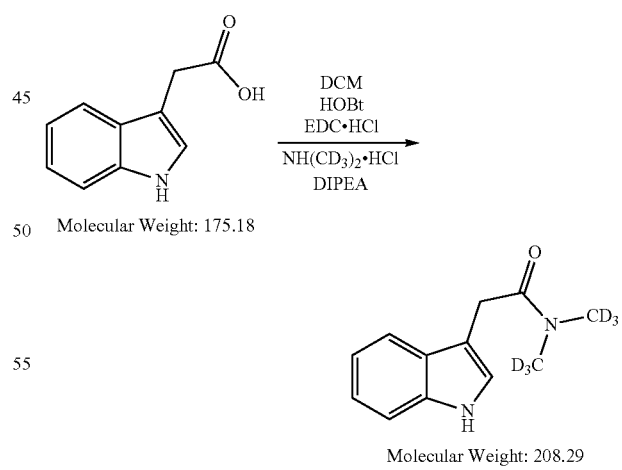

Molecular Weight: 175.18

Molecular Weight: 208.29

EDC·HCl (15.7 g, 81.90 mmol) was added to 3-indoleacetic acid (12.0 g, 68.50 mmol) and HOBt·$H_2O$ (1.16 g, 75.75 mmol) in DCM (108 mL) at room temperature. The reaction was stirred for 1 hour after which N,N-diisopropylethylamine (DIPEA) (35.6 mL, 205.75 mmol) and $d_6$-dimethylamine·HCl (9.0 g, 102.76 mmol) were added (temperature maintained below 30° C.). The reaction was stirred for 1 hour at room temperature after which analysis by HPLC indicated 65.6% product with 28.9% 3-indoleacetic acid remaining. DIPEA (11.9 mL, 68.78 mmol) was added and the reaction was stirred for 1 hour at room temperature. HPLC indicated no change in conversion. Aqueous potassium carbonate (6.0 g in 54 mL water) was added and the phases were separated. The aqueous phase was extracted with DCM (2×30 mL). The combined organics were washed with brine (2×30 mL) then aqueous citric acid (20 w/w %, 50 mL), dried over MgSO₄ and filtered. The filtrate was stripped and the resulting solids were slurried in TBME (120 mL) and isolated by filtration. Purification by flash column chromatography yielded 8.34 g of the desired product (58% yield). ¹H NMR confirmed the identity of the product.

Stage 2

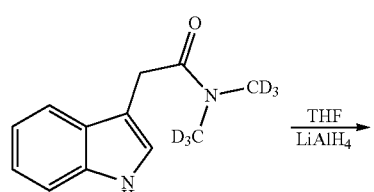

Molecular Weight: 208.29

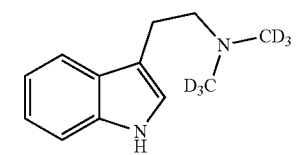

Molecular Weight: 194.31

LiAlH₄ (1 M in THF, 17.3 mL, 17.28 mmol) was added to a suspension of stage 1 (4.0 g, 19.20 mmol) in THF (10 mL) at <30° C. The resulting reaction was heated to 60-65° C. and stirred for 2 hours. HPLC analysis indicated complete consumption of stage 1 with 97.3% product formed. The reaction was cooled to room temperature and quenched into aqueous Rochelle's salts (10 g in 30 mL water) at <30° C. After stirring for 1 hour, the phases were separated. The aqueous phase was extracted with THF (20 mL). The combined organics were washed with brine (20 mL), dried over MgSO₄, filtered and stripped (azeotroped with ethanol, 20 mL) to give the desired product as an amber oil (3.97 g). ¹H NMR confirmed the identity of the product and indicated 8.5% ethanol was present (no THF) giving an active yield of 3.63 g, 97%.

Stage 3

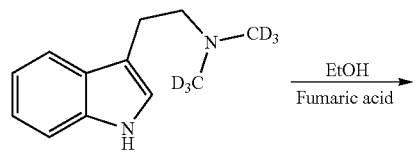

Molecular Weight: 194.31

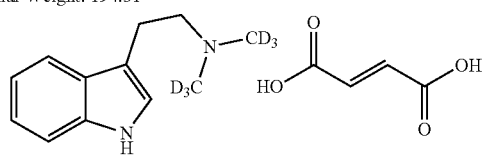

Molecular Weight: 310.38 d₆-DMT free base (3.6 g active, 18.53 mmol) was dissolved in ethanol (43 mL) at room temperature. Fumaric acid (2.15 g, 18.53 mmol) was added and the solution was heated to 75° C. (solids crystallised during heating and did not re-dissolve). The resulting suspension was cooled to 0-5° C. and stirred for 1 hour. The solids were isolated by filtration, washed with ethanol (2×7 mL) and pulled dry. Further drying in a vacuum oven at 50° C. yielded the desired d₆-DMT fumaric acid salt (4.98 g, 87%).

Synthesis of d₈-DMT (SPL028viii)

For stage 1 (coupling of 3-indoleacetic acid and d₆-dimethylamine), see above

Stage 2

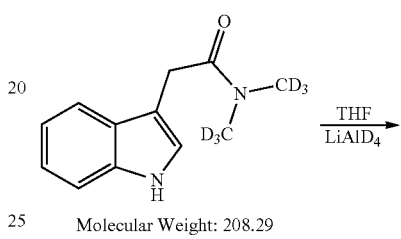

Molecular Weight: 208.29

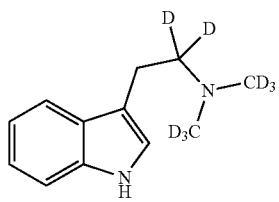

Molecular Weight: 196.32

LiAlD₄ (1 M in THF, 17.3 mL, 17.28 mmol) was added to a suspension of stage 1 (4.0 g, 19.20 mmol) in THF (10 mL) at <30° C. The resulting reaction was heated to 60-65° C. and stirred for 2 hours. HPLC analysis indicated complete consumption of the stage 1 with 97.3% product formed. The reaction was cooled to room temperature and quenched into aqueous Rochelle's salts (10 g in 30 mL water) at <30° C. After stirring for 1 hour, the phases were separated. The aqueous phase was extracted with THF (20 mL). The combined organics were washed with brine (20 mL), dried over MgSO₄, filtered and stripped (azeotroped with ethanol, 20 mL) to give the desired product as an amber oil (4.01 g). ¹H NMR confirmed the identity of the product and indicated 8.6% ethanol was present (no THF) giving an active yield of 3.66 g, 97%.

Stage 3

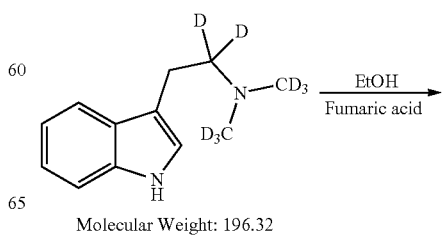

Molecular Weight: 196.32

-continued

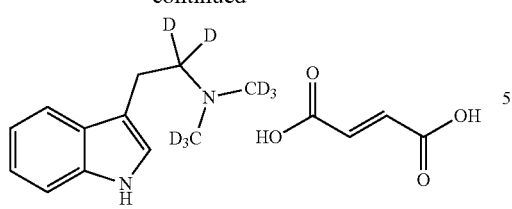

Molecular Weight: 312.39 d$_8$-DMT free base (3.6 g active, 18.53 mmol) was dissolved in ethanol (43 mL) at room temperature. Fumaric acid (2.15 g, 18.53 mmol) was added and the solution was heated to 75° C. (solids crystallised during heating and did not re-dissolve). The resulting suspension was cooled to 0-5° C. and stirred for 1 hour. The solids were isolated by filtration, washed with ethanol (2×7 mL) and pulled dry. Further drying in a vacuum oven at 50° C. yielded the desired d$_8$-DMT fumaric acid salt (4.62 g, 81%).

Assessment of Extents of Deuteration

This was achieved by LCMS-SIM (SIM=single ion monitoring), the analysis giving a separate ion count for each mass for the deuterated N,N-dimethyltryptamine compounds at the retention time for N,N-dimethyltryptamine. The percentage of each component was then calculated from these ion counts.

For example, % D0=[D0/(D0+D1+D2)]×100.

HPLC Parameters

System: Agilent 1100/1200 series liquid chromatograph or equivalent

Column: Triart Phenyl; 150×4.6 mm, 3.0 μm particle size (Ex: YMC, Part number: TPH12S03-1546PTH)

Mobile phase A: Water:Trifluoroacetic acid (100:0.05%)

Mobile phase B: Acetonitrile:Trifluoroacetic acid (100:0.05%)

| Gradient: | Time | % A | % B |
|---|---|---|---|
| | 0 | 95 | 5 |
| | 13 | 62 | 38 |
| | 26 | 5 | 95 |
| | 30.5 | 5 | 95 |
| | 31 | 95 | 5 |

| Flow rate: | 1.0 mL/min |
|---|---|
| Stop time: | 31 minutes Post runtime: 4 minutes |
| Injection volume: | 5 μL Wash vial: N/A |
| Column temperature | 30° C. combined |
| Wavelength: | 200 nm, (4 nm) Reference: N/A |

Mass Spectrometry Parameters

| System: | Agilent 6100 series Quadrupole LC-MS or equivalent | | |
|---|---|---|---|
| Drying gas flow: | 12.0 L/min | Drying gas temp.: | 350° C. |
| Nebuliser pressure: | 35 psig | | |
| Fragmentor: | 110 | Gain: | 1.00 |

| Cpd | RT | RRT | Conc | Diluent | Detection | Mass |
|---|---|---|---|---|---|---|
| D0 | 10.64 | 1.00 | 0.30 mg/ml | CH$_3$CN:H$_2$O (50:50) | (+) SIM | 189.10 m/z |
| D1 | 10.64 | 1.00 | 0.30 mg/ml | CH$_3$CN:H$_2$O (50:50) | (+) SIM | 190.10 m/z |
| D2 | 10.64 | 1.00 | 0.30 mg/ml | CH$_3$CN:H$_2$O (50:50) | (+) SIM | 191.10 m/z |

MS-SIM range is the target mass ±0.1 m/z

Human Hepatocyte Intrinsic Clearance

In vitro determination of intrinsic clearance (Clint) is a valuable model for predicting in vivo clearance. The liver contains both phase I and phase II drug metabolising enzymes, which are present in the intact cell and thereby provides a valuable model for the study of drug metabolism. In particular CLint in hepatocytes is a measure of the potential of a compound to undergo metabolism and can be related to hepatic clearance in vivo by also taking into consideration plasma protein binding and liver blood flow. Therefore, CLint may be used as an index of the relative metabolic stability of compounds and compared with other external probe substrates. Furthermore, the measurement of CLint in vitro, where hepatic metabolic clearance is known to be an issue, may be a useful means of understanding the different pharmacokinetic behaviour of compounds in vivo.

Assay Method

Human (mixed gender) hepatocytes pooled from 10 donors were used to investigate the in vitro intrinsic clearance of SPL026 and SL028 analogues in three separate experiments:

First experiment—Human (Mixed Gender) Hepatocytes; 0.545 million cells/mL. Final organic concentration 1.05% consisting of 80.74% of MeCN and 19.26% DMSO Second experiment—Human (Mixed Gender) Hepatocytes; 0.427 million cells/mL. Final organic concentration 1% consisting of 84.7% of MeCN and 15.3% DMSO.

Third experiment—Human (Mixed Gender) Hepatocytes; 0.362 million cells/mL

Mouse CD-1 (Male) Hepatocytes

Final organic concentration 1% consisting of 84.7% of MeCN and 15.3% DMSO

Assay Preparation

Hepatocyte buffer is prepared as 26.2 mM NaHCO$_3$, 9 mM Na HEPES, 2.2 mM D-Fructose and DMEM in MilliQ water.

Compound and marker stocks are prepared at 10 mM in DMSO and further diluted to 100× the assay concentration in 91:9 acetonitrile:DMSO.

Hepatocytes are thawed rapidly in a water bath at 37° C. and, once just thawed, decanted into hepatocyte buffer. Cells are centrifuged and the supernatant removed before counting and resuspension at the final assay concentration.

Assay Procedure

A concentration of 5 μM was used for all test compounds, as well as sumatriptan, serotonin, benzylamine controls with 2 replicate incubations per compound in each experiment. This concentration was chosen in order to maximise the signal-to-noise ratio, while remaining under the Michaelis constant (K$_m$) for the monoamine oxidase enzyme (MAO). Diltiazem and diclofenac controls were used at a laboratory-validated concentration of 1 μM.

Hepatocytes are added to pre-warmed incubation tubes (37° C.). Pre-prepared 100× assay compound stocks are then added to the incubation tubes and mixed carefully. Samples are taken at 7 time points (2, 4, 8, 15, 30, 45 and 60 minutes).

At each timepoint, small aliquots were withdrawn from the incubation and quenched 1:4 with ice-cold acidified methanol or acetonitrile containing internal standard.

Incubation tubes are orbitally shaken at 37° C. throughout the experiment.

Standard final incubation conditions are 1 μM compound in buffer containing nominally ~0.5 million viable cells/mL, ~0.9% (v/v) acetonitrile (MeCN) and ~0.1% (v/v) DMSO (specific assay concentrations outlined above, section 2).

Quenched samples are mixed thoroughly, and protein precipitated at −20° C. for a minimum of 12 hours. Samples are then centrifuged at 4° C. Supernatants are transferred to a fresh 96-well plate for analysis.

Liquid Chromatography-Mass Spectrometry (LC-MS/MS)

The following LC-MS/MS conditions were used for the analysis:

Instrument: Thermo TSQ Quantiva with Thermo Vanquish UPLC system
Column: Luna Omega 2.1×50 mm 2.6 μm
Solvent A: $H_2O$+0.1% formic acid
Solvent B: Acetonitrile+0.1% formic acid
Flow rate: 0.8 ml/min
Injection vol: 1 μl
Column temp: 65° C.
Gradient:

| Time (mins) | % Solvent B |
|---|---|
| 0.00 | 5.0 |
| 0.90 | 75.0 |
| 1.36 | 99.0 |
| 1.36 | 5.0 |
| 1.80 | 5.0 |

MS parameters:
Positive ion spray voltage: 4000 V
Vaporiser temperature: 450° C.
Ion transfer tube temp: 365° C.
Sheath gas: 54
Aux gas: 17
Sweep gas: 1
Dwell time 8 ms
MRM transitions:
D0=mass to charge ratio 189.136>144.179 (method determined from SPL026 analysis)
D1=mass to charge ratio 190.136>59.17 (method determined from SPL028ii analysis)
D2=mass to charge ratio 191.137>60.169 (method determined from SPL028i analysis)
D6=mass to charge ratio 195.17>64.127
D8=mass to charge ratio 197.2>146.17

The MRM transitions were determined from a preliminary analysis of DMT samples containing either no deuterium (for D0 transition), or high levels of either D1, D2, D6 or D8 deuteration (for the D1, D2, D6 and D8 transitions respectively).

The resulting concentration-time profile was then used to calculate intrinsic clearance (CLint) and half-life (t½). To do this, the MS peak area or MS peak area/IS response of each analyte is plotted on a natural log scale on the y axis versus time (min) of sampling on the X axis. The slope of this line is the elimination rate constant. This is converted to a half-life by −ln(2)/slope. Intrinsic clearance is calculated from the slope/elimination rate constant and the formula is CLint=(−1000*slope)/cell density in 1E6 cells/ml, to give units of microlitre/min/million cells.

Clearance of Six Different $D_2DMT$ Analogue Blends (SPL028i-SPL028vi) With and Without MAO Inhibitors The contribution of MAO of six different α,α,-bis-deuterium-N,N-dimethyltryptamine ($D_2DMT$) compounds was examined using an irreversible, combined MAO-A/B inhibitor (100 nM clorgyline and 100 nM Deprenyl/Selegiline added as a cassette) via the measurement of in vitro intrinsic clearance using human (mixed gender) hepatocytes from 10 donors (0.545 million cell s/mL; final organic concentration 1.05% consisting of 80.74% of MeCN and 19.26% DMSO).

Effect of Deuteration

Data were fitted with two separate linear models using linear regression analyses (one-way ANOVA), which revealed that deuterium enrichment at the α-carbon of DMT decreases intrinsic clearance linearly with increasing percentage of $D_2$-deuteration using the formula: $y=D_2*-6.04+12.9$, $r^2=0.748$ and molecular weight (MW) using the formula: $y=MW*79.5+98.8$, $r^2=0.811$.

96.6% $D_2$-DMT (SPL028i) saw the biggest change in metabolic stability, ~2-fold change in intrinsic clearance and half-life compared to SPL026 in initial hepatocyte studies (Table 3 and Table 4). The metabolic stability of intermediate blends of deuteration (SPL028ii-SPL028vi) increased in a manner which correlated with increasing level of deuteration and molecular weight (Table 3 and Table 4).

TABLE 3

In vitro Intrinsic clearance of SPL026 and 6 different $D_2$-deuterated SPL028 analogue blends in in human hepatocytes, highlighting the fold change in intrinsic clearance from SPL026 for each deuterated compound, with and without inhibitors. Compounds ordered via molecular weight.

| Cpd name | Molecular weight | Ratio of deuteration ($D_0:D_1:D_2$) | Intrinsic clearance (μL/min/million cells) | | | |
|---|---|---|---|---|---|---|
| | | | Without inhibitors | Fold change from SPL026 | With inhibitors | Fold change from SPL026 |
| SPL026 | 188.27 | 100:0:0 | 13.77 | 1.00 | 13.24 | 1.00 |
| SPL028v | 188.9098 | 48:41:11 | 10.99 | 1.25 | 9.51 | 1.39 |
| SPL028vi | 188.9613 | 57:35:7 | 13.64 | 1.01 | 10.79 | 1.23 |
| SPL028ii | 189.1915 | 30:48:22 | 10.46 | 1.32 | 8.78 | 1.51 |
| SPL028iii | 189.6685 | 17:47:37 | 9.36 | 1.47 | 6.90 | 1.92 |
| SPL028iv | 189.6764 | 9:42:49 | 11.14 | 1.24 | 7.46 | 1.77 |
| SPL028i | 190.2398 | 1:3:97 | 7.15 | 1.93 | 7.50 | 1.77 |
| Benzylamine | | | 16.70 | | <3.0 | |
| Serotonin | | | 38.60 | | 10.10 | |

TABLE 4

In vitro half-life of SPL026 and 6 different $D_2$-deuterated SPL028 analogue blends in in human hepatocytes, highlighting the fold change in intrinsic clearance from SPL026 for each deuterated compound, with and without inhibitors. Compounds ordered via molecular weight.

| Cpd name | Molecular weight | Ratio of deuteration ($D_0:D_1:D_2$) | Without inhibitors | Fold change from SPL026 | With inhibitors | Fold change from SPL026 |
|---|---|---|---|---|---|---|
| SPL026 | 188.27 | 100:0:0 | 92.39 | 1.00 | 96.06 | 1.00 |
| SPL028v | 188.9098 | 48:41:11 | 119.61 | 1.29 | 135.10 | 1.41 |
| SPL028vi | 188.9613 | 57:35:7 | 95.04 | 1.03 | 119.62 | 1.25 |
| SPL028ii | 189.1915 | 30:48:22 | 125.80 | 1.36 | 147.47 | 1.54 |
| SPL028iii | 189.6685 | 17:47:37 | 140.43 | 1.52 | 189.60 | 1.97 |
| SPL028iv | 189.6764 | 9:42:49 | 116.84 | 1.26 | 171.17 | 1.78 |
| SPL028i | 190.2398 | 1:3:97 | 178.79 | 1.94 | 169.75 | 1.77 |
| Benzylamine | | | 76.30 | | 460.00 | |
| Serotonin | | | 33.00 | | 125.70 | |

Figure 2:
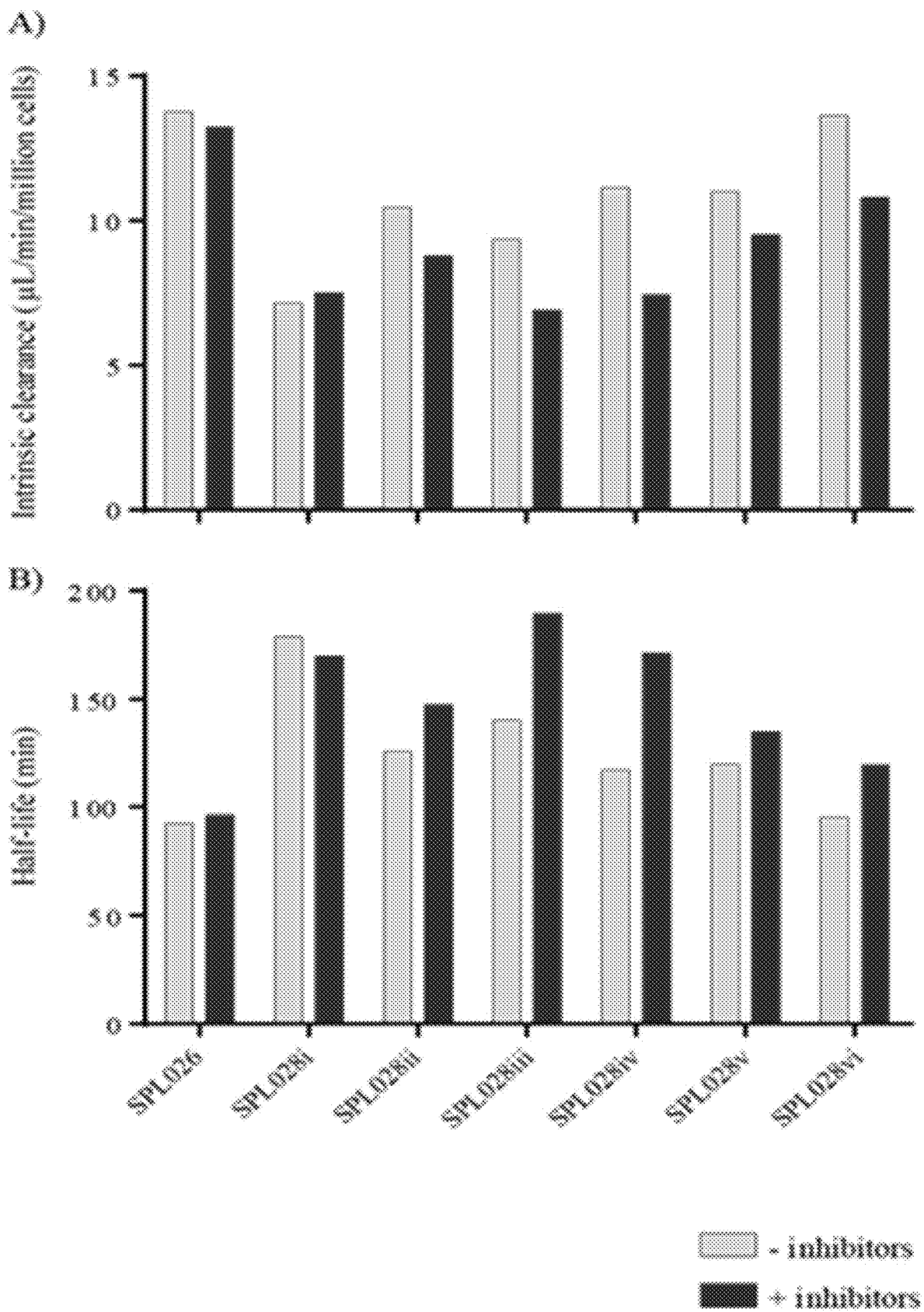
FIG. 2: In vitro intrinsic clearance (A) and half-life (B) of DMT (SPL026) and 6 different D$_2$-deuterated SPL028 analogue blends in human hepatocytes with and without MAO-A/B inhibitor combination, as described in the Example section, below.

Contribution of MAO (See Also FIG. 2)

Two-way ANOVA was carried out to determine the influence of MAO inhibitors and compound deuteration on intrinsic clearance. There was a significant effect of MAO inhibitors on intrinsic clearance $F(1, 6)=11.42$, $p=0.0149$, and deuteration on intrinsic clearance $F(1,6)=9.996$, $p=0.006$.

The inclusion of MAO inhibitors was shown to have minimal effect on the metabolism of SPL026 (DMT) resulting in ~4% slower intrinsic clearance (Table 5). MAO inhibitors were also shown to have a small effect on the 96.6% $D_2$-deuterated analogue (SPL028i) which saw a ~5% quicker intrinsic clearance in the presence of MAO inhibitors (Table 5). These results indicate that MAO enzymes do not significantly contribute to the metabolism of SPL026 and SPL028i in human liver hepatocytes.

MAO inhibitors were shown to have a greater inhibitory effect on intrinsic clearance for the remaining five $D_2$-deuterated analogue blends (SPL028ii-SPL028vi). For these five compounds, the inhibitory action of MAO inhibitors was shown to increase linearly with increasing level of deuteration and molecular weight, with the exception of SPL028vi (Table 3). 49% $D_2$-deuterated SPL028iv saw the largest change in intrinsic clearance (49%) with the inclusion of MAO inhibitors (Table 5), whereas 36.8% $D_2$-deuterated SPL028iii saw the largest change (~2 fold) in metabolic stability relative to SPL026 in cellular fractions with inhibitors (Table 3 and 4).

TABLE 5

In vitro Intrinsic clearance and half-life of SPL026 and 6 different $D_2$-deuterated SPL028 analogue blends in in human hepatocytes with and without MAO-A/B inhibitor combination. Percentage change (%) values represent the % change in metabolic stability with the inclusion of MAO inhibitors vs no inhibitors, measured by intrinsic clearance and half-life separately. Compounds are ordered by increasing molecular weight.

| Cpd Name | Mol. weight | Ratio of deuteration ($D_0:D_1:D_2$) | Intrinsic clearance (µL/min/million cells) | | | Half-life (min) | | |
|---|---|---|---|---|---|---|---|---|
| | | | Without inhibitors | With inhibitors | % change | Without inhibitors | With inhibitors | % change |
| SPL026 | 188.27 | 100:0:0 | 13.77 | 13.24 | −4.00 | 92.39 | 96.06 | 3.82 |
| SPL028v | 188.9098 | 48:41:11 | 10.99 | 9.51 | −15.56 | 119.61 | 135.1 | 11.47 |
| SPL028vi | 188.9613 | 57:35:7 | 13.64 | 10.79 | −26.41 | 95.04 | 119.62 | 20.55 |
| SPL028ii | 189.1915 | 30:48:22 | 10.46 | 8.78 | −19.13 | 125.8 | 147.47 | 14.69 |
| SPL028iii | 189.6685 | 17:47:37 | 9.36 | 6.9 | −35.65 | 140.43 | 189.6 | 25.93 |
| SPL028iv | 189.6764 | 9:42:49 | 11.14 | 7.46 | −49.33 | 116.84 | 171.17 | 31.74 |
| SPL028i | 190.2398 | 1:3:97 | 7.15 | 7.5 | 4.67 | 178.79 | 169.75 | −5.33 |
| Benzylamine | | | 16.7 | <3.0 | <−450 | 76.3 | 460 | >83.41 |
| Serotonin | | | 38.6 | 10.1 | −282.18 | 33 | 125.7 | 73.75 |

These results indicate that increasing the level of deuteration at the α-carbon of DMT decreases the MAO enzyme metabolism of the compound.

Clearance of Six $D_2$DMT Analogue Blends (SPL028i-SPL028vi) and One $D_6$-DMT (SPL028vii) Analogue Blends In vitro human hepatic intrinsic clearance of the six different α,α,-bis-deuterium-N,N-dimethyltryptamine ($D_2$DMT) compounds and one N,N-hexadeuterio-dimethyltryptamine ($D_6$DMT, SPL028vii) were measured to investigate the effects of methyl group deuteration vs α-carbon deuteration on metabolic stability in using human (mixed gender) hepatocytes from 10 donors (0.427 million cells/mL; final organic concentration 1% consisting of 84.7% of MeCN and 15.3% DMSO).

TABLE 6

In vitro intrinsic clearance and half-life of 6 different $D_2$-deuterated DMT and $D_8$-deuterated DMT analogue blends in human hepatocytes, ordered by increasing level of molecular weight

| Compound Name | Intrinsic clearance (μL/min/million cells) | Half-life (min) |
|---|---|---|
| SPL028v | 14.1 | 119 |
| SPL028vi | 13.4 | 126.8 |
| SPL028ii | 9.1 | 191.1 |
| SPL028iii | 8.2 | 213.9 |
| SPL028iv | 7.7 | 223.9 |
| SPL028i | 6.3 | 258.3 |
| SPL028vii ($D_6$) | 13.3 | 122.2 |
| Diltiazem (A) | 15.3 | 15.0 |
| Diltiazem (B) | 17.2 | 18.2 |
| Diclofenac (A) | 155.0 | 154.0 |
| Diclofenac (B) | 150.1 | 154.3 |

Data fitted with a linear regression model on the six different $D_2$-deuterated confirmed previous findings that deuterium enrichment at the α-carbon of DMT decreases intrinsic clearance linearly with increasing level of $D_2$-deuteration, $y=D_2*-8.07+12.9$, $r^2=0.690$ and molecular weight. A linear regression model was also fitted by molecular weight using formula: $y=MW*13.9+6.06$, $r^2=0.923$ revealing molecular weight is a strong predictor of intrinsic clearance for the 6 different $D_2$-deuterated SPL028 blends.

Initial hepatocyte data did not suggest a relationship between molecular weight and intrinsic clearance of $D_2$-deuterated and $D_6$-deuterated SPL028 blends, $r^2=0.0395$.

Clearance of Two $D_2$DMT (SPL028i and SPL028ii), One $D_6$DMT (SPL028vii) and One $D_8$-DMT (SPL028viii) Analogue Blends Further human hepatocyte assays were conducted with two $D_2$-deuterated SLP028 analogue blends and two additional deuterated analogues: $D_6$DMT and $D_8$DMT to measure in vitro intrinsic clearance using human (mixed gender) hepatocytes from 10 donors (0.362 million cells/mL).

TABLE 7

In vitro intrinsic clearance and half-life of two different $D_2$-deuterated DMT, $D_6$-deuterated DMT and $D_8$-deuterated DMT analogue blends in human hepatocytes, ordered by increasing level of molecular weight

| Compound Name | Intrinsic Clearance (μL/min/million cells) | Fold change from SPL026 | Half-life (min) | Fold change from SPL026 |
|---|---|---|---|---|
| SPL026 | 19.4 | 1.0 | 98.9 | 1.0 |
| SPL028ii | 11.7 | 1.7 | 170.9 | 1.7 |
| SPL028i | 8.3 | 2.3 | 233.1 | 2.4 |
| SPL028vii | 17.1 | 1.1 | 112.1 | 1.1 |
| SPL028viii | 9.3 | 2.1 | 206.9 | 2.1 |
| Diltiazem | 22.0 |  | 87.3 |  |
| Diclofenac | 92.5 |  | 20.7 |  |

A linear regression model did not support a predictive relationship between molecular weight and intrinsic clearance for SPL026, SPL028i, SPL028ii, SPL029vii and SPL028viii, $r^2=0.0445$.

In agreement with hepatocyte results presented above, deuteration of the methyl group in $D_6$-deuterated SPL028vii appeared not to effect intrinsic clearance in human hepatocytes relative to SPL026. Intrinsic clearance of SPL026 (19.4 μL/min/million cells)–Intrinsic clearance of SPL028vii (17.1 μL/min/million cells)=2.3 μL/min/million cells.

Complete deuterium enrichment at both the α-carbon and methyl group of DMT in the $D_8$-deuterated SPL028viii compound also appeared not to significantly change metabolic stability relative to 96.6% α-carbon $D_2$-deuterated SPL028i analogue. Intrinsic clearance of SPL028i (8.3 μL/min/million cells)–Intrinsic clearance of SPL028viii (9.3 μL/min/million cells)=1.0 μL/min/million cells.

In Vitro Mouse Hepatocytic Intrinsic Clearance

The in vitro intrinsic clearance of six different $D_2$-deuterated SPL028 analogues blends relative to SPL026 was performed using mouse (male CD-1) hepatocytes (0.367 million cells/mL; final organic concentration 1% consisting of 84.7% of MeCN and 15.3% DMSO).

Data was compared to in vitro human hepatocyte intrinsic clearance results to assess the suitability of an in vivo mouse model to predict human metabolism of SPL026 and SPL028 compounds. A concentration of 5 μM was used for all test compounds, as well as serotonin, benzylamine, diltiazem and diclofenac internal controls with 2 replicate incubations per compound.

TABLE 8

In vitro half-life and intrinsic clearance of SPL026 and 6 × $D_2$-deuterated SPL028 deuterated compounds in mouse hepatocytes. Compounds ordered by increasing molecular weight.

| Compound Name | w Intrinsic clearance (μL/min/million cells) | Fold change from SPL026 | w Half-life (min) | Fold change from SPL026 |
|---|---|---|---|---|
| SPL026 | 123.5 | 1.00 | 15.3 | 1.00 |
| SPL028v | 117.7 | 1.05 | 16.1 | 1.05 |
| SPL028vi | 114.0 | 1.08 | 16.6 | 1.08 |
| SPL028ii | 102.7 | 1.20 | 18.4 | 1.20 |
| SPL028iii | 106.2 | 1.16 | 17.9 | 1.17 |
| SPL028iv | 106.9 | 1.16 | 17.7 | 1.16 |
| SPL028i | 97.4 | 1.27 | 19.4 | 1.27 |
| Serotonin | 83.0 |  | 22.8 |  |
| Benzylamine | 134.1 |  | 14.3 |  |
| Diltiazem | >460.0 |  | <3.0 |  |
| Diclofenac | 57.7 |  | 34.1 |  |

Use of Liver Mitochondrial Fraction to Model Human Metabolism of Deuterated DMT

Given the predicted 5 minute half-life of DMT in humans, the inventors expect that DMT is largely broken down before reaching the human liver. Therefore, an alternative in vitro assay was selected as a more appropriate system to model human metabolism of DMT. The following assays conducted on Human Liver Mitochondrial (HLMt) fractions predict enhanced fold-change between SPL026 and $D_2$-deuterated SPL028i compared with the fold-change predicted in hepatocyte studies. Moreover, an additional protective effect is observed between $D_2$-deuterated SPL028i and $D_8$-deuterated SPL028viii, supportive of a synergistic effect on mitochondrial metabolism when both the α-carbon and methyl group(s) of DMT and DMT analogues of formula (I) are deuterated.

Contribution of MAO-A and MAO-B In Vitro Human Liver Mitochondrial Fraction Intrinsic Clearance Human Liver Mitochondrial (HLMt) fractions contain high quantities of MAO enzymes and therefore, provide a useful tool to measure the clearance of MAO substrates.

A series of investigations using HLMts were conducted to assess the effect of MAO on the metabolism of DMT and deuterated DMT analogues in vitro.

In Vitro Human Mitochondrial Fraction Intrinsic Clearance of SPL026 (DMT) With/Without MAO-A and MAO-B Inhibitors In vitro determination of the intrinsic clearance of SPL026 with selective and irreversible MAO-A inhibitor (100 nM clorgyline) and MAO-B inhibitor (100 nM Deprenyl/Selegiline) were added separately to 0.5 mg/mL of human liver mitochondrial fraction. The MAO-A substrate, Serotonin and MAO-B substrate, Benzylamine were added as positive controls which confirmed the presence of MAO-A and MAO-B and the action of Clorgyline and Deprenyl inhibitors.

TABLE 9

Intrinsic clearance and half-life of SPL026 in human liver mitochondrial fraction

| Compound Name | Inhibitor | Intrinsic Clearance (µL/min/mg protein) | Half-life (min) |
| --- | --- | --- | --- |
| SPL026 | DMSO Vehicle | 42.9 | 33.7 |
| SPL026 | Clorgyline (MAO-A inhibitor) | <3.9 | >373.7 |
| SPL026 | Deprenyl (MAO-B inhibitor) | 42.7 | 32.5 |
| Serotonin | DMSO Vehicle | 124.6 | 11.1 |
| Serotonin | Clorgyline | <3.3 | >420.2 |
| Benzylamine | DMSO Vehicle | 45.7 | 30.4 |
| Benzylamine | Deprenyl | <3.3 | >420.2 |

SPL026 half-life and intrinsic clearance significantly increased with MAO-A inhibitor (Clorgyline), resulting in a 11-fold increase in intrinsic clearance compared data from SPL026 without MAO inhibitors. Deprenyl (MAO-B inhibitor) showed no difference in human mitochondrial intrinsic clearance relative to fraction without inhibitors. These results suggest that a role of MAO-A but not MAO-B, in the metabolism of SPL026.

In Vitro Human Mitochondrial Fraction Intrinsic Clearance of SPL026 (DMT), SPL028i (96.6% $D_2$-DMT), SPL028iii (36.8% $D_2$-DMT) and SPL028viii ($D_8$-DMT)

In vitro determination of the intrinsic clearance of SPL026, SPL028i, SPL028iii and SPL028viii were added separately to 0.5 mg/mL of human liver mitochondrial fraction. The MAO-A substrate 'Serotonin' and MAO-B substrate 'Benzylamine' were added as positive controls and confirmed the presence of MAO-A and MAO-B.

TABLE 10

Intrinsic clearance and half-life of SPL026, SPL028i, SPL028iii, SPL028viii in human liver mitochondrial fraction

| Compound Name | Intrinsic Clearance (µL/min/mg protein) | Fold change from SPL026 | Half-life (min) | Fold change from SPL026 |
| --- | --- | --- | --- | --- |
| SPL026 | 161.0 | 1.0 | 8.6 | 1.0 |
| SPL028iii | 15.0 | 3.6 | 31.1 | 3.6 |
| SPL028i | 44.6 | 10.7 | 92.8 | 10.8 |
| SPL028viii | 10.9 | 14.8 | 127.7 | 14.8 |
| Serotonin | 151.0 | — | 9.2 | — |
| Benzylamine | 60.0 | — | 23.2 | — |

Half-life and intrinsic clearance increased with increasing level of deuteration for the SPL028 compounds, when compared to SPL026. $D_8$-deuterated SPL028viii saw the greatest change in clearance (14.8 fold increase) relative to SPL026. 96.6% $D_2$-deuterated SPL028i also showed a large change (10.7 fold increase) in clearance compared to SPL026. 36.80% $D_2$-deuterated SPL028iii demonstrated a smaller change (3.6 fold increase) in clearance compared to SPL026.

Cytochrome P450 (CYP) Phenotyping Against 8 Human CYPs

The members of the Cytochrome P450 (CYP) superfamily are considered the most important drug metabolising enzymes. A detailed understanding of the contribution of individual CYPs towards the clearance of a drug candidate is important to 8 in the production and understanding of potential drug-drug interactions.

Some CYP isoforms, e.g. CYP2D6, CYP2C9, CYP2C19, known to be polymorphic leading to significant intra-individual variability in the rate metabolism, which can alter drug exposure significantly and, as a consequence, affect drug efficacy and safety.

The CYPs used in this study are heterologously expressed in E. coli and purchased as individualised forms (CYP bactosomes) from CYPEX. Bactosomes contain recombinant CYP isoenzymes combined with CYP reductase leading to a higher specific activity than liver microsomes. As many as 18 human CYPs plus a variety of CYPs from preclinical species along with other drug-metabolising enzymes are currently commercially available.

Assay Method

Preparation

Phosphate buffer is prepared at 0.1 M, pH 7.4 by combining 0.1 M $Na_2HPO_4$ and 0.1 M $KH_2PO_4$ solutions.

Compound and marker stocks are prepared at 10 mM and DMSO and further diluted to 100× the assay concentration in DMSO.

Nicotinamide adenine dinucleotide 2'-phosphate reduced tetrasodium salt hydrate (NADPH) is prepared at 10 m<in 0.1 M phosphate buffer (pH 7.4).

The individual CYP bactosomes are thawed at room temperature undiluted to 200 pmol/mL and 0.1 M phosphate buffer.

Procedure

Pre-prepared 100× assay compound stocks/markers, and 2× assay CYP bactosomes are added to incubation tubes, mixed and pre-warmed at 37° C. for 5 minutes. Pre-warmed NADPH is then added to the incubation tubes and mixed well. Samples were taken at predetermined time points. At each time point, a sample is removed from incubation and quenched 1:4 with ice-cold methanol or acetonitrile containing internal standard. Incubation tubes are orbitally shaken at 37° C. throughout the experiment.

Standard final incubation conditions are 1-3 μM compound in a buffer containing 100 pmol/mL CYP bactosome, 1% (v/v) DMSO.

Quenched samples are mixed thoroughly and protein precipitated at −20° C. for a minimum of 12 hours. Samples were then centrifuged at −4° C. Supernatants are transferred to a fresh 96-well plate for analysis.

Positive control markers are as specified in Table 11.

TABLE 11

Positive control markers used for the determination of metabolic intrinsic clearance by 8 human CYP isoforms

| CYP450 | Positive controls | |
|---|---|---|
| 1A2 | Carvedilol | Tacrine |
| 2B6 | Bupropion | Ticlopidine |
| 2C8 | Montelukast | Verapamil |
| 2C9 | Carvedilol | Diclofenac |
| 2C19 | Carvedilol | Propranolol |
| 2D6 | Carvedilol | Dextromethorphan |
| 3A4 | Carvedilol | Midazolam |
| 3A5 | Midazolam | Verapamil |

Data Processing

The elimination rate constant (k) is calculated using the slope of a ln (MS peak area or response—if internal standard is used) vs. time plot of the test compounds and markers.

Intrinsic clearance in μL/min/nmol CYP is calculated using the following equation:

Clint=−1000 k/CYP concentration

Projected CYP isoform intrinsic clearance accounting for estimated CYP abundance in human liver microsomes (μL/min/mg microsomal protein)* is calculated using the following equation:

Projected set isoform intrinsic clearance=Estimated CYP abundance*Clint

* Estimated CYP abundance is taken as an average from three literature references 1, 2 3 and the abundances used are as follows (nmol CYP/mg Human Liver Microsomal Protein):

| CYP450 | 1A2 | 2B6 | 2C8 | 2C9 | 2C19 | 2D6 | 3A4 | 3A5 |
|---|---|---|---|---|---|---|---|---|
| Abundance (nmol CYP/mg H mic protein) | 0.032 | 0.023 | 0.024 | 0.060 | 0.009 | 0.012 | 0.075 | 0.009 |

Reference 1: McGinnty et al. (2000) Automated definition of the enzymology of drug oxidation by the major human drug metabolizing cytochrome P450s, *Drug Metabolism and Disposition,* 28, 1327-1334

Reference 2: Ohtsuki et al. (2012), Simultaneous Absolute Protein Quantification of Transporters, Cytochromes P450 and UDP-Glucuronosyltransferases as a Novel Approach for the Characterization of Individual Human Liver: Comparison with mRNA Levels and Activities, *Drug Metabolism and Disposition,* 40, 83-92

Reference 3: Achour et al. (2014) Simultaneous Quantification of the Abundance of Several Cytochrome P450 and Uridine 59-Diphospho-Glucuronosyltransferase Enzymes in Human Liver Microsomes Using Multiplexed Targeted Proteomics, *Drug Metabolism and Disposition,* 42, 500-510 (guidelines and example)

CYP phenotyping was conducted to investigate the contribution of CYP isoforms in the metabolism of SPL026 and 2 different D2-deuterated SPL028 analogues (SPL028i, SPL028ii) and the positive controls mentioned in Table 11 above.

Intrinsic clearance, half-life and projected intrinsic clearance of 8 human CYPs (CYP1A2, CYP2B6, CYP2C8, CYP2C9, CYP2C19, CYP2D6, CYP3A5) in *E. coli* CYPEX membranes with SPL026 and 2× SPL028 $D_2$-deuterated analogue blends are presented in Tables 12-14.

CYP2D6 had the largest effect on intrinsic clearance of SPL026 and 2-$D_2$-deuterated DMT analogues (SPL028i and SPL028ii). CYP2C19 had a small effect on the intrinsic clearance of all three tested compounds. No significant difference in $CYP2C_{19}$ intrinsic clearance or half-life between SPL026, SPL028i and SPL018ii was found as determined by one-way ANOVA (F(2,3)=0.769, p=0.538) and (F(2,3)=0.789, p=0.530), respectively. There was also no significant difference in CYP2D6 intrinsic clearance or half-life between SPL026, SPL028i and SPL028ii as determined by one-way ANOVA (F(2,3)=0.510, p=0.644) and (F(2,3)=0.512, p=0.644) respectively.

No turnover of any other CYP isoform (1A2, 2B6, 2C8, 2C9, 3A4, 3A5) was recorded (half-life>240 minutes and intrinsic clearance<29 μL/min/nmol) indicating no significant effect on SPL026 and deuterated SPL028 analogue metabolism.

TABLE 12

In vitro intrinsic clearance of SPL026 and 2 × $D_2$-deuterated SPL028 deuterated compounds and markers through CYP phenotyping using 8 human CYPs (CYP1A2, CYP2B6, CYP2C8, CYP2C9, CYP2C19, CYP2D6, CYP3A4 and CYP3A5) in *E. coli* CYPEX membranes.

| | CYP isoform and intrinsic clearance (μL/min/nmol CYP) | | | | | | | |
|---|---|---|---|---|---|---|---|---|
| Cpd | 1A2 | 2B6 | 2C8 | 2C9 | 2C19 | 2D6 | 3A4 | 3A5 |
| DMT (SPL026) | <29 | <29 | <29 | <29 | 37 | 801 | <29 | <29 |
| DMT in SPL028i | <29 | <29 | <29 | <29 | 40 | 687 | <29 | <29 |
| DMT in SPL028ii | <29 | <29 | <29 | <29 | 43 | 803 | <29 | <29 |
| SPL028i | <29 | <29 | <29 | <29 | 39 | 793 | <29 | <29 |
| SPL028i in DMT | <29 | <29 | <29 | <29 | 30 | 914 | <29 | <29 |
| SPL028i in SPL028ii | <29 | <29 | <29 | <29 | 39 | 789 | <29 | <29 |
| SPL028ii | <29 | <29 | <29 | <29 | 39 | 801 | <29 | <29 |
| SPL028ii in DMT | <29 | <29 | <29 | <29 | 39 | 806 | <29 | <29 |

TABLE 12-continued

In vitro intrinsic clearance of SPL026 and 2 × $D_2$-deuterated
SPL028 deuterated compounds and markers through CYP phenotyping
using 8 human CYPs (CYP1A2, CYP2B6, CYP2C8, CYP2C9, CYP2C19, CYP2D6,
CYP3A4 and CYP3A5) in *E. coli* CYPEX membranes.

| Cpd | CYP isoform and intrinsic clearance (μL/min/nmol CYP) | | | | | | | |
|---|---|---|---|---|---|---|---|---|
| | 1A2 | 2B6 | 2C8 | 2C9 | 2C19 | 2D6 | 3A4 | 3A5 |
| SPL028ii in SPL028i | <29 | <29 | <29 | <29 | 41 | 790 | <29 | <29 |
| Carvedilol | 231 | | | 52 | 526 | 4483 | 142 | |
| Tacrine | 189 | | | | | | | |
| Bupropion | | 51 | | | | | | |
| Ticlopidine | | 1640 | | | | | | |
| Montelukast | | | 122 | | | | | |
| Verapamil | | | 1244 | | | | | 267 |
| Diclofenac | | | | 4731 | | | | |
| Propranolol | | | | | 566 | | | |
| Dextromethorphan | | | | | | 2686 | | |
| Midazolam | | | | | | | 1369 | 623 |

TABLE 13

In vitro half-life of SPL026 and 2 × $D_2$-deuterated SPL028
deuterated compounds and markers through CYP phenotyping
using 8 human CYPs (CYP1A2, CYP2B6, CYP2C8, CYP2C9, CYP2C19,
CYP2D6, CYP3A4 and CYP3A5) in *E. coli* CYPEX membranes.

| Cpd | CYP isoform and half-life (min) | | | | | | | |
|---|---|---|---|---|---|---|---|---|
| | 1A2 | 2B6 | 2C8 | 2C9 | 2C19 | 2D6 | 3A4 | 3A5 |
| DMT (SPL026) | >240 | >240 | >240 | >240 | 189 | 9 | >240 | >240 |
| DMT in SPL028i | >240 | >240 | >240 | >240 | 176 | 10 | >240 | >240 |
| DMT in SPL028ii | >240 | >240 | >240 | >240 | 162 | 9 | >240 | >240 |
| SPL028i | >240 | >240 | >240 | >240 | 180 | 9 | >240 | >240 |
| SPL028i in DMT | >240 | >240 | >240 | >240 | 237 | 8 | >240 | >240 |
| SPL028i in SPL028ii | >240 | >240 | >240 | >240 | 179 | 9 | >240 | >240 |
| SPL028ii | >240 | >240 | >240 | >240 | 176 | 9 | >240 | >240 |
| SPL028ii in DMT | >240 | >240 | >240 | >240 | 177 | 9 | >240 | >240 |
| SPL028ii in SPL028i | >240 | >240 | >240 | >240 | 172 | 9 | >240 | >240 |
| Carvedilol | 30 | | | 134 | 13 | 2 | 49 | |
| Tacrine | 37 | | | | | | | |
| Bupropion | | 135 | | | | | | |
| Ticlopidine | | 4 | | | | | | |
| Montelukast | | | 62 | | | | | |
| Verapamil | | | 6 | | | | | 26 |
| Diclofenac | | | | 1 | | | | |
| Propranolol | | | | | 12 | | | |
| Dextromethorphan | | | | | | 3 | | |
| Midazolam | | | | | | | 5 | 11 |

TABLE 14

Projected scaled intrinsic clearance of CYP2C19 and CYP2D6 isoforms
for SPL206, SPL028i and SPL028ii. Projected scaled intrinsic
clearance for other CYP isoforms were not calculated as no turnover
was detected (<29 μl/min/nmol) in phenotyping assay.

| Compound | CYP isoform and projected scaled intrinsic clearance (μl/min/mg microsomal protein) | |
|---|---|---|
| | 2C19 | 2D6 |
| DMT (SPL026) | 0.3 | 9.5 |
| DMT in SPL028i | 0.4 | 8.1 |
| DMT in SPL028ii | 0.4 | 9.5 |
| SPL028i | 0.3 | 9.4 |
| SPL028i in DMT | 0.3 | 10.8 |
| SPL028i in SPL028ii | 0.4 | 9.3 |
| SPL028ii | 0.4 | 9.5 |
| SPL028ii in DMT | 0.4 | 9.5 |
| SPL028ii in SPL028i | 0.4 | 9.3 |

Results suggest a role of CYP2D6 and 2C19 in the metabolism of SPL026 and D$_2$-deuterated SPL028 analogues.

CONCLUSION

α-Carbon Deuteration of DMT Increases Metabolic Stability

This series of in vitro investigations on the metabolic stability of SPL026 and eight different deuterated analogue blends indicate that deuteration of the α-carbon increases the metabolic stability of DMT in a progressive manner.

We found different DKIE effects of SPL028 compounds in different human and animal tissues. The largest DKIE, measured via reduced intrinsic clearance and increased half-life, were recorded in human liver mitochondrial fractions. In this fraction the most α-deuterated SPL028 compounds, (96.6% D$_2$) SPL028i and (D$_8$) SPL028viii saw the largest difference in metabolic stability relative to un-deuterated SPL026, each result saw a ~10.8 and ~14.8-fold change from SPL026 respectively.

MAO-A Metabolism is the Predominant Metabolic Pathway of DMT in Human Mitochondrial Fraction Mitochondrial fractions contain a high proportion of MAO enzymes compared to human liver hepatocytes. This was confirmed by the differences in clearance and half-life values of serotonin (MAO-A substrate) and benzylamine (MAO-B substrate) positive controls between human hepatocytes and human liver mitochondrial fraction. Compared to hepatocyte fraction, human liver mitochondria saw a ~3.9 fold and ~3.6-fold increase in intrinsic clearance for MAO-A substrate and MAO-B substrate respectively. Inclusion of MAO-A inhibitors were shown to have a significant effect on the clearance of SPL026, whereas MAO-B inhibitors caused no change to the metabolic stability of SPL026 in mitochondrial fraction. These findings suggest that α-deuteration of DMT inhibits the oxidative deamination metabolic pathway involving MAO-A enzymes.

CYP2D6 and CYP2C19 Provide an Alternative Metabolic Pathway for DMT and α-Deuterated-DMT CYP phenotyping demonstrated a role of CYP2D6 and CYP2C19 enzyme metabolism of SPL026 and 2 different D$_2$-deuterated (SPL028i, SPL028ii) at equivalent levels. This data indicates that in addition to MAO-A, alternative enzymes are responsible for the metabolism of SPL026 and deuterated SPL028 compounds.

The invention claimed is:

1. A method of synthesising a compound of formula (I'):

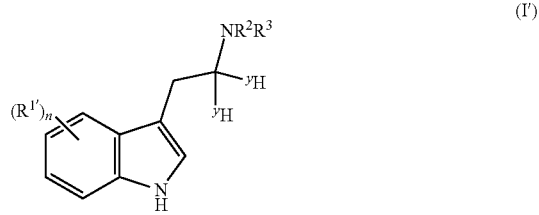

or a pharmaceutically acceptable salt thereof, comprising reacting a compound of formula (II):

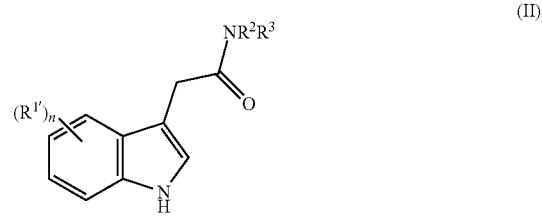

with LiAlH$_4$ and/or LiAlD$_4$, wherein the compound of formula (II) is made by:

reacting a compound of formula (III)

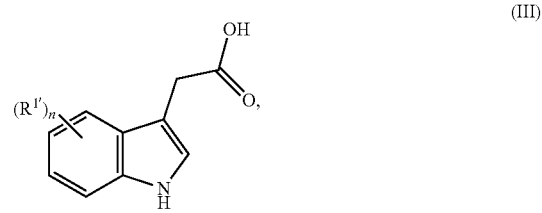

with two or more coupling agents to produce an activated compound; and (ii) reacting the activated compound with an amine having the formula R$^2$R$^3$NH or R$^2$R$^3$ND, wherein:

R$^{1'}$ is independently selected from —R$^4$, —OPR, —OR$^4$, —F, —Cl, —Br and —I;

PR is a protecting group, n is selected from 0, 1, 2, 3 or 4;

R$^2$ is C($^x$H)$_3$;

R$^3$ is C($^x$H)$_3$ or H;

each R$^4$ is independently selected from C$_1$-C$_4$alkyl; and each $^x$H and $^y$H is independently protium or deuterium, wherein a ratio of deuterium:protium in a C($^x$H)$_3$ moiety in the compound of formula (I') is greater than that found naturally in hydrogen, or a pharmaceutically acceptable salt thereof.

2. The method of claim 1 wherein a ratio of LiAlH$_4$ and/or LiAlD$_4$:compound of formula (II) of 0.8:1 to 1:1 is used.

3. The method of claim 1 wherein the two or more coupling agents comprise an additive coupling agent.

4. The method of claim 3, wherein the two or more coupling agents comprise a carbodiimide.

5. The method of claim 3, wherein the additive coupling agent is selected from the group consisting of 1-hydroxybenzotriazole, hydroxy-3,4-dihydro-4-oxo-1,2,3-benzotriazine, N-hydroxysuccinimide, 1-hydroxy-7-aza-1H-benzotriazole, ethyl 2-cyano-2-(hydroximino)acetate and 4-(N,N-Dimethylamino)pyridine.

6. A method of psychedelic-assisted psychotherapy for treating a psychiatric or neurological disorder, comprising:

administering to a patient in need thereof the compound

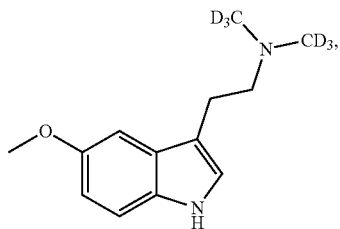 [SMILES: [2H]C([2H])([2H])N(CCc1c[nH]c2ccc(OC)cc12)C([2H])([2H])[2H]]

or a pharmaceutically acceptable salt thereof.

7. A method of psychedelic-assisted psychotherapy for treating a psychiatric or neurological disorder, comprising: administering to a patient in need thereof a compound of formula:

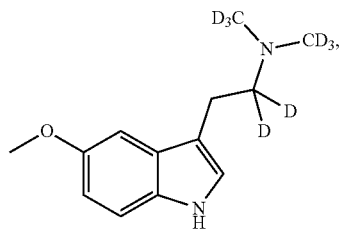 [SMILES: [2H]C([2H])([2H])N(C([2H])([2H])[2H])C([2H])([2H])Cc1c[nH]c2ccc(OC)cc12]

or a pharmaceutically acceptable salt thereof,
wherein the patient in need thereof is subjected to a psychedelic experience induced by administration of the compound, or a pharmaceutically acceptable salt thereof.

* * * * *